(12) United States Patent
Dugi et al.

(10) Patent No.: US 10,092,571 B2
(45) Date of Patent: *Oct. 9, 2018

(54) TREATMENT OF GENOTYPED DIABETIC PATIENTS WITH DPP-IV INHIBITORS SUCH AS LINAGLIPTIN

(71) Applicant: Boehringer Ingelheim International GmbH, Ingelheim am Rhein (DE)

(72) Inventors: Klaus Dugi, London (GB); Eva Ulrike Graefe-Mody, Ingelheim am Rhein (DE); Michael Mark, Biberach an der Riss (DE); Hans-Juergen Woerle, Munich (DE); Heike Zimdahl-Gelling, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/235,575

(22) Filed: Aug. 12, 2016

(65) Prior Publication Data

US 2016/0354380 A1 Dec. 8, 2016

Related U.S. Application Data

(63) Continuation of application No. 13/511,771, filed as application No. PCT/EP2010/068349 on Nov. 26, 2010, now Pat. No. 9,457,029.

(30) Foreign Application Priority Data

Nov. 27, 2009 (EP) ..................................... 09177418
Jun. 21, 2010 (EP) ..................................... 10166714

(51) Int. Cl.
| | | |
|---|---|---|
| *A61K 31/155* | (2006.01) | |
| *A61K 31/44* | (2006.01) | |
| *A61K 31/519* | (2006.01) | |
| *A61K 45/06* | (2006.01) | |
| *A61K 31/522* | (2006.01) | |
| *A61K 31/4439* | (2006.01) | |
| *A61K 31/4985* | (2006.01) | |
| *A61K 31/513* | (2006.01) | |
| *A61K 38/26* | (2006.01) | |
| *A61K 38/28* | (2006.01) | |

(52) U.S. Cl.
CPC .......... *A61K 31/522* (2013.01); *A61K 31/155* (2013.01); *A61K 31/44* (2013.01); *A61K 31/4439* (2013.01); *A61K 31/4985* (2013.01); *A61K 31/513* (2013.01); *A61K 31/519* (2013.01); *A61K 38/26* (2013.01); *A61K 38/28* (2013.01); *A61K 45/06* (2013.01)

(58) Field of Classification Search
None
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,741,898 A | 5/1988 | Mallik et al. |
| 4,743,450 A | 5/1988 | Harris et al. |
| 4,764,466 A | 8/1988 | Suyama et al. |
| 4,816,455 A | 3/1989 | Schickaneder et al. |
| 4,873,330 A | 10/1989 | Lindholm |
| 4,968,672 A | 11/1990 | Jacobson et al. |
| 5,034,225 A | 7/1991 | Bennett et al. |
| 5,041,448 A | 8/1991 | Janssens et al. |
| 5,051,509 A | 9/1991 | Nagano et al. |
| 5,051,517 A | 9/1991 | Findeisen et al. |
| 5,084,460 A | 1/1992 | Munson, Jr. et al. |
| 5,120,712 A | 6/1992 | Habener |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Medline Plus, "Obesity" 2013, Retrieved from internet on Aug. 22, 2013, http://www.nlm.nih.gov/medlineplus/obesity.html.

(Continued)

*Primary Examiner* — Julie Ha
*Assistant Examiner* — Kristina M Hellman
(74) *Attorney, Agent, or Firm* — Paula K. Wittmayer; David L. Kershner

(57) ABSTRACT

The present invention relates to methods for preventing or treating of metabolic disorders and related conditions, such as in certain patient groups.

9 Claims, 2 Drawing Sheets

Specification includes a Sequence Listing.

(56) References Cited

U.S. PATENT DOCUMENTS

| | | |
|---|---|---|
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahmdt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,448,323 B1 | 9/2002 | Jordan et al. |
| 6,548,481 B1 | 4/2003 | Demuth et al. |
| 6,579,868 B1 | 6/2003 | Asano et al. |
| 6,689,353 B1 | 2/2004 | Wang et al. |
| 6,699,845 B2 | 3/2004 | Asahi |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,282,219 B2 | 10/2007 | Nomura et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Boehringer et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,338,450 B2 | 12/2012 | Arora et al. |
| 8,399,414 B2 | 3/2013 | Harada et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 | 3/2014 | Dugi et al. |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 | 11/2015 | Dugi et al. |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 | 2/2016 | Sieger et al. |
| 9,321,791 B2 | 4/2016 | Himmelsbach et al. |
| 9,415,016 B2 | 8/2016 | Friedl et al. |
| 9,486,426 B2 | 8/2016 | Eller |
| 9,457,029 B2 | 10/2016 | Dugi et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0104983 A1 | 6/2003 | DeFelippis et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |

(56) References Cited

U.S. PATENT DOCUMENTS

| | | |
|---|---|---|
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2004/0266806 A1 | 12/2004 | Sanghvi et al. |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0097798 A1 | 5/2005 | Evans et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0059797 A1 | 3/2007 | Low et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0197552 A1 | 8/2007 | Carr |
| 2007/0219178 A1 | 9/2007 | Muramoto |
| 2007/0254944 A1 | 11/2007 | Hughes |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0265349 A1 | 11/2007 | Rapin et al. |
| 2007/0281940 A1 | 12/2007 | Dugi et al. |
| 2007/0299076 A1 | 12/2007 | Piotrowski et al. |
| 2008/0014270 A1 | 1/2008 | Harada |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2010/0330177 A1 | 12/2010 | Pourkavoos |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0212982 A1 | 9/2011 | Christopher et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0232004 A1 | 9/2012 | Bachovchin et al. |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0086076 A1 | 4/2013 | Pandit et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0303554 A1 | 11/2013 | Klein et al. |
| 2013/0310398 A1 | 11/2013 | Mark et al. |

(56) References Cited

U.S. PATENT DOCUMENTS

| | | |
|---|---|---|
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0315832 A1 | 10/2014 | Broedl et al. |
| 2014/0343014 A1 | 11/2014 | Klein et al. |
| 2014/0371243 A1 | 12/2014 | Klein et al. |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0058769 A1 | 3/2016 | Graefe-Mody et al. |
| 2016/0082011 A1 | 3/2016 | Klein et al. |
| 2016/0106677 A1 | 4/2016 | Boeck et al. |
| 2016/0310435 A1 | 10/2016 | Friedl et al. |
| 2017/0020868 A1 | 1/2017 | Dugi et al. |

FOREIGN PATENT DOCUMENTS

| | | |
|---|---|---|
| CA | 1123437 A1 | 5/1982 |
| CA | 2136288 A1 | 5/1995 |
| CA | 2375779 | 5/2000 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CA | 2720450 A1 | 10/2009 |
| CN | 101234105 A | 8/2008 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EA | 201300121 | 10/2009 |
| EP | 0023032 A1 | 1/1981 |
| EP | 0149578 A2 | 7/1985 |
| EP | 0189941 A2 | 8/1986 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 61030567 | 2/1986 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004196824 A | 7/2004 |
| JP | 2004250336 A | 9/2004 |
| JP | 2005511636 A | 4/2005 |
| JP | 2005519059 A | 6/2005 |
| JP | 2006503013 A | 1/2006 |
| JP | 2006045156 A | 2/2006 |
| JP | 2006137678 A | 6/2006 |
| JP | 2007510059 A | 4/2007 |
| JP | 2007522251 A | 8/2007 |
| JP | 2007531780 A | 11/2007 |
| JP | 2008513390 A | 5/2008 |
| JP | 2008536881 A | 9/2008 |
| JP | 2010500326 A | 1/2010 |
| JP | 2010053576 A | 3/2010 |
| JP | 2010070576 A | 4/2010 |
| JP | 2010524580 A | 7/2010 |
| JP | 2010535850 A | 11/2010 |
| JP | 2010536734 A | 12/2010 |
| JP | 2011088838 A | 5/2011 |
| JP | 2011529945 A | 12/2011 |
| JP | 2012502081 A | 1/2012 |
| JP | 2012505859 A | 3/2012 |
| KR | 20070111099 A | 11/2007 |
| WO | 8706941 A1 | 11/1987 |
| WO | 199107945 A1 | 6/1991 |
| WO | 199205175 A1 | 4/1992 |
| WO | 199219227 A2 | 11/1992 |
| WO | 199402150 A1 | 2/1994 |
| WO | 199403456 A1 | 2/1994 |
| WO | 9532178 A1 | 11/1995 |
| WO | 199609045 A1 | 3/1996 |
| WO | 199611917 A1 | 4/1996 |
| WO | 199636638 A1 | 11/1996 |
| WO | 199718814 A1 | 5/1997 |
| WO | 199723447 A1 | 7/1997 |
| WO | 199723473 A1 | 7/1997 |
| WO | 199746526 A1 | 12/1997 |
| WO | 1998007725 | 2/1998 |
| WO | 199811893 | 3/1998 |
| WO | 9818770 A1 | 5/1998 |

(56) References Cited

FOREIGN PATENT DOCUMENTS

| | | |
|---|---|---|
| WO | 199822464 A1 | 5/1998 |
| WO | 199828007 A1 | 7/1998 |
| WO | 199840069 A2 | 9/1998 |
| WO | 1998046082 A1 | 10/1998 |
| WO | 199856406 A1 | 12/1998 |
| WO | 199929695 A1 | 6/1999 |
| WO | 1999038501 A2 | 8/1999 |
| WO | 199950248 A1 | 10/1999 |
| WO | 199956561 A1 | 11/1999 |
| WO | 199967279 A1 | 12/1999 |
| WO | 200012064 A1 | 3/2000 |
| WO | 200072873 | 5/2000 |
| WO | 200034241 A1 | 6/2000 |
| WO | 0069464 A1 | 11/2000 |
| WO | 0072799 A2 | 12/2000 |
| WO | 0078735 A1 | 12/2000 |
| WO | 200072973 A1 | 12/2000 |
| WO | 200073307 A2 | 12/2000 |
| WO | 200107441 A1 | 2/2001 |
| WO | 2001032158 A2 | 5/2001 |
| WO | 2001040180 A2 | 6/2001 |
| WO | 200152825 | 7/2001 |
| WO | 200152852 A1 | 7/2001 |
| WO | 2001047514 A1 | 7/2001 |
| WO | 2001051919 | 7/2001 |
| WO | 2001066548 A1 | 9/2001 |
| WO | 2001068603 | 9/2001 |
| WO | 2001068646 A1 | 9/2001 |
| WO | 200177110 A1 | 10/2001 |
| WO | 2001072290 A2 | 10/2001 |
| WO | 200196301 A1 | 12/2001 |
| WO | 200197808 A1 | 12/2001 |
| WO | 200202560 A2 | 1/2002 |
| WO | 200214271 A1 | 2/2002 |
| WO | 200224698 A1 | 3/2002 |
| WO | 2002053516 A2 | 7/2002 |
| WO | 2002068420 A1 | 9/2002 |
| WO | 2003000241 A2 | 1/2003 |
| WO | 2003000250 | 1/2003 |
| WO | 2003002531 A2 | 1/2003 |
| WO | 2003002553 A2 | 1/2003 |
| WO | 2003004496 A1 | 1/2003 |
| WO | 2003006425 A2 | 1/2003 |
| WO | 2003024965 A2 | 3/2003 |
| WO | 2003033686 A2 | 4/2003 |
| WO | 2003034944 A1 | 5/2003 |
| WO | 2003035177 A2 | 5/2003 |
| WO | 2003037327 A1 | 5/2003 |
| WO | 2003053929 A1 | 7/2003 |
| WO | 2003055881 A1 | 7/2003 |
| WO | 2003057200 A2 | 7/2003 |
| WO | 2003059327 | 7/2003 |
| WO | 2003064454 A1 | 8/2003 |
| WO | 2003074500 A2 | 9/2003 |
| WO | 2003088900 A2 | 10/2003 |
| WO | 2003094909 A2 | 11/2003 |
| WO | 2003099279 A1 | 12/2003 |
| WO | 2003099836 A1 | 12/2003 |
| WO | 2003104229 A1 | 12/2003 |
| WO | 2003106428 A1 | 12/2003 |
| WO | 2004002924 A1 | 1/2004 |
| WO | 2004011416 A1 | 2/2004 |
| WO | 2004016587 A1 | 2/2004 |
| WO | 2000003735 | 3/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |
| WO | 2005007647 A1 | 1/2005 |
| WO | 2005007658 A2 | 1/2005 |
| WO | 2005012288 A1 | 2/2005 |
| WO | 2005016365 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005075410 A1 | 8/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005097798 A1 | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007038979 A1 | 4/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |

(56) References Cited

FOREIGN PATENT DOCUMENTS

| | | |
|---|---|---|
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2003057245 | 1/2008 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008077639 A1 | 7/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008097180 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 | 2/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 201092124 | 2/2010 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092124 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010140111 A1 | 12/2010 |
| WO | 2010147768 A1 | 12/2010 |
| WO | 2011011541 A1 | 1/2011 |
| WO | 2007033266 | 4/2011 |
| WO | 2011039337 A1 | 4/2011 |
| WO | 2011039367 A2 | 4/2011 |
| WO | 2011064352 A1 | 6/2011 |
| WO | 2011109333 | 9/2011 |
| WO | 2011113947 A1 | 9/2011 |
| WO | 2011138380 A1 | 11/2011 |
| WO | 2011138421 A1 | 11/2011 |
| WO | 2011154496 A1 | 12/2011 |
| WO | 2011161161 A1 | 12/2011 |
| WO | 2011163206 A2 | 12/2011 |
| WO | 2012031124 A2 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2003061688 | 4/2013 |
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |
| WO | 2014140284 A1 | 9/2014 |
| WO | 2014170383 A1 | 10/2014 |

OTHER PUBLICATIONS

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck Manual of Diagnosis and Therapy: "Obesity." 1999, 17th Edition, Chapter 5, pp. 58-62.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.

MIMS Jan. 2009, "Sitagliptin." pp. 152-153.

Nabors, Lyn O'Brien "Alternative Sweeteners." Marcel Dekker, Inc., 2001, pp. 235, 339-340.

Naik, R. et al., "Latent Autoimmune Diabetes in Adults." The Journal of Clinical Endocrinology and Metabolism, 2009, vol. 94, No. 12, pp. 4635-4644.

Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

National Program for Care Guidelines, "Type 2 Diabetes mellitus." 2002, First Edition, pp. 1-50.

Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.

Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.

Nielsen, L., "Incretin Mimetics and DPP-IV Inhibitors for the Treatment of Type 2 Diabetes." Drug Discovery Today, 2005, vol. 10, No. 10, pp. 703-710.

Nihon Ijinpo, Japan Medicinal Journal, 2001, No. 4032, p. 137.

Novartis AG, Investor Relations Release, "Galvus, a new oral treatment for type 2 diabetes, receives positive opinion recommending European Union approval." Securities and Exchange Commission, Form 6-K, 2007, pp. 1-4.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Office Action for U.S. Appl. No. 10/695,597 dated May 2, 2008.

Oz, Helieh S., "Methionine Deficiency and Hepatic Injury in a Dietary Steatohepatitis Model." Digestive Diseases and Sciences, 2008, vol. 53, No. 3, pp. 767-776.

Patani George A. et al.: "Bioisoterism : A Rational Approach in Drug Design", Chemical Reviews, 1996, vol. 96, No. 8, pp. 3147-3176.

(56) References Cited

OTHER PUBLICATIONS

Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Pietruck, F. et al., "Rosiglitazone is a safe and effective treatment option of new-onset diabetes mellitus after renal transplantation." Transplant International, 2005, vol. 18, pp. 483-486.
Pilgaard, K. et al., "The T allele of rs7903146 TCF7L2 is associated with impaired insulinotropic action of incretin hormones, reduced 24 h profiles of plasma insulin and glucagon, and increased hepatic glucose production in young healthy men." Diabetologia, 2009, vol. 52, pp. 1298-1307.
Plummer, C.J.G. et al., "The Effect of Melting Point Distributions on DSC Melting Peaks." Polymer Bulletin, 1996, vol. 36, pp. 355-360.
Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.
Prescribing Information, Package insert for Leprinton tablets 100mg, Manufacturer: Tatsumi Kagaku Co., Ltd., Mar. 2003, pp. 1-3.
Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rowe, R. et al., Handbook of Pharmaceutical Excipients, Fifth Edition, Pharmaceutical Press, 2006, pp. 389-395, 449-453, and 731-733.
Rowe, R. et al., Handbook of Pharmaceutical Excipients, Fourth Edition, Pharmaceutical Press and American Pharmaceutical Association, 2003, pp. 323-332.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?" JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schillinger, M. et al., "Restenosis after percutaneous angioplasty: the role of vascular inflammation." Vascular Health and Risk Management, 2005, vol. 1, No. 1, pp. 73-78.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schnapp, G. et al., "Analysis of Binding Kinetics and Thermodynamics of DPP-4 Inhibitors and their Relationship to Structure." 23rd PSDI, Protein Structure Determination in Industry, Tegernsee, Germany, Nov. 8-10, 2015.
Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014.
Schnapp, G. et al., "Comparative Enzyme Kinetic Analysis of the Launched DPP-4 Inhibitors." American Diabetes Association 74th Scientific Sessions, Poster 1048-P, 2014.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Gennaro, Alfonso; Remington: The Science and Practice of Pharmacy, Twentieth Edition, 2000, Chapter 45, pp. 860-869.
Giron, D.; Thermal Analysis and Calorimetric Methods in the Characterisation of Polymorphs and Solvates; Thermochimica Acta (1995) vol. 248 pp. 1-59.
GLUCOPHAGE® Prescribing Information, 2001.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al, "Insulin Therapy:current alternatives", Arch. Med.Res. 36: p. 258-272 (2005).
Goodarzi, M.O. et al., "Metformin revisited: re-evaluation of its properties and role in the pharmacopoeia of modern antidiabetic agents." Diabetes, Obesity and Metabolism, 2005, vol. 7, pp. 654-665.
Graefe-Mody et al., "The novel DPP-4 inhibitor BI 1356 (proposed tradename ONDERO) and Metformin can be Safely Co-administered Without Dose Adjustment." Poster No. 553-P ADA Jun. 6-10, 2008, San Francisco http://professional.diabetes.org/content/posters/2008/p553-p.pdf.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time-and Dpse-Dependent Localization in Kidney, Liver, and Intestine after Intravenous Dosing: Results from High Resolution Autoradiography in Rats", 2010, vol. 38, No. 9, p. 1443-1448.
Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcaf7-1539-42d5-8dda-0a94abb089e8>.

(56) References Cited

OTHER PUBLICATIONS

Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.
Gwaltney, S. "Medicinal Chemistry Approaches to the Inhibition of Dipeptidyl Peptidase IV", Current Topics in Medicinal Chemistry, 2008, 8, p. 1545-1552.
Gwaltney, S.L. II et al., "Inhibitors of Dipeptidyl Peptidase 4." Annual Reports in Medicinal Chemistry, 2005, vol. 40, pp. 149-165.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Halimi, "Combination treatment in the management of type 2 diabetes: focus on vildagliptin and metformin as a single tablet", Vascular Health and Risk Management, 2008 481-92.
Halimi, S. et al., "Combination treatment in the management of type 2 diabetes: focus on vildagliptin and metformin as a single tablet." Vascular Health and Risk Management, 2008, vol. 4, No. 3, pp. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hammouda, Y. et al., "Lactose-induced Discoloration of Amino Drugs in Solid Dosage Form." Die Pharmazie, 1971, vol. 26, p. 181.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
He, Y.L. et al., "The influence of hepatic imparment on the pharmacokinetics f the dipeptidyl peptidase IV (DPP-4) inhibitor vildagliptin" European Journal of Clinical Pharmacology, vol. 63, No. 7, May 8, 2007, p. 677-686.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal of the American Board of Family Medicine, 2006, vol. 19, No. 6, pp. 612-620.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemia/reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Horsford, E. N. "On the source of free hydrochloric acid in the gastric juice." Proceedings of the Royal Society of London, Published in 1868-1869, vol. 17, pp. 391-395.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
Hull, R. et al., "Nephrotic syndrome in adults." British Medical Journal, 2008, vol. 336, pp. 1185-1190.
Hunziker, et al, "Inhibitors of DPP IV-recent advances and structural views", Current Topics in Medicinal Chemistry, 2005, vol. 5 issue 16, pp. 1623-1637.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Canadian Diabetes Association, "Pharmacologic Management of Type 2 Diabetes." Canadian Journal of Diabetes, 2003, vol. 27, Suppl. 2, pp. S37-S42.
Canadian Pharmacists Association, Compendium of Pharmaceuticals and Specialties, "Zestril" 2004, pp. 2289-2293.
Cao, C. et al., "The clinical application of linagliptin in Asians." Therapeutics and Clinical Risk Management, 2015, vol. 11, pp. 1409-1419.

(56) References Cited

OTHER PUBLICATIONS

Castello, R. et al., "Discoloration of Tablets Containing Amines and Lactose." Journal of Pharmaceutical Sciences, 1962, vol. 51, No. 2, pp. 106-108.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn2.vlu/Page/vsc/en/ch/12/oc/substitution/sn_2/abgangsgrupen/abgangsgruppe.vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2 methyl-,S-(2 [[[1-(2-ethylbutyl)cyclohexyl}carbonyl}amino}pheyl}ester". Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 NO3. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Clinical Trial NCT00622284 (published online at clinicaltrials.gov on Feb. 22, 2008).
Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Clinical Trial, NCT00622284, clinicaltrials.gov, updated Feb. 22, 2008.
Clinical Trials NCT00601250, clinicaltrials.gov, Jan. 25, 2008.
Clinical Trials, No. NCT00309608, "Efficacy and Safety of BI 1356 BS in Combination with Metformin in Patients With type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].
Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Colorcon, "Lactose Replacement with Starch 1500 in a Direct Compression Formula." 2005, pp. 1-4.
Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Cotton, M.L. et al., "L-649,923—The selection of an appropriate salt form and preparation of a stable oral formulation." International Journal of Pharmaceutics, 1994, vol. 109, Issue 3, pp. 237-249.

(56) References Cited

OTHER PUBLICATIONS

Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.
Crowe, E. et al., "Early identification and management of chronic kidney disease: summary of NICE guidance." British Medical Journal, 2008, vol. 337, pp. 812-815.
Hansen, European Journal of Pharmacology, "The DPP-IV inhibitor linagliptin and GLP-1 induce synergistic effects on body weight loss and appetite suppression in the diet-induced obese rat", 2014, p. 254-263.
Ferreira, Triple Combination therapy with sitagliptin, metformin and rosiglitazone improves glycaemic control in patiens with type 2 diabetes, Diabetologixa, 2008, Suppl 1.
Byrn, Pharmaceutical Solids, A Strategic Approach to Regulatory Considerations, Pharmaceutical Research, 1995, vol. 12.
Morhenn (2), Keratinocyte proliferation in wound healing and skin diseases, Immunology Today, vol. 9, 1994.
Diabetes, Type 1 Diabetes-Associated Autoantibodies, 2009, vol. 52, Issue 8, p. 675-677.
Merck manual, 18th Edition, published Apr. 25, 2007, p. 594-598, Japanese Edition.
Scientific Discussion on Sifrol, EMEA, 2005, p. 1-9.
Scientific Discussion for Sifrol, European Public Assessment Reports, 2005, p. 1.
The Textbook of Pharmaceutics, Pharmcaeutical Subcomitee Hanrimwon, 2005, p. 1-6.
Mettler Toledo "Interpreting DSC curves Part 1: Dynamic Measurements" Jan. 2000. Available from www.masointechnology.ie.x/Usercom_11.pdf.
Glucophage (metformin hydrocholoride tablets) revised label, 2003.
Stahl, Selected Procedures for the Preparation of Pharmaceutically Acceptable salts, Handbook of Pharmaceutical Salts Properties, Chapter 11, 2015.
Caira, Crystalline Polymorphism of Organic Compounds, Topics in Current Chemistry, vol. 198, 2015.
Brittain, Polymorphism on Pharmaceutical Solids, Chapter 5 Generation of Polymorphs, vol. 95, 1999, p. 183-226.
Luo, Theory and Practice of Modern Physical Pharmacy, Shangai Scientific and Technical Literature Publishing House, 2005, p. 294.
Thomas, (R)-8-Amino-piperidin-1-yl)-7-but-2-ynyl-3-methyl-1-(4-methyl-quinazolin-2-ylmethyl)-3,7-dihydro-purine-2,6-dione(BI1236, a Novel Xanthine based Dipeptidyl Peptidase 4 inhibitor, has a Superior Potency and longer duration of action compared with other dipeptyl Peptidase-4 inhibitors, The Journal of Pharmacology and Experimental Therapeutica, vol. 325, 2008, p. 175-182.
Kim, Comparison of DPP-4 Inhibitors, The Journal of Korean Diabetes, http:dx.doi.org/10.4093/jkd.2013.14.3.111.
Medicine Department of Pharmacy, Pharmaceutical Subcommitte, Book Publishing Harwinton, 1996, p. 283.
Huang, et al. Elimination of metformin-croscarmellose sodium interaction by competition, International Journal of Pharmaceutics, 2006, p. 33-39.
Freeman, Initial Combination therapy for patients with type 2 diabetes mellitus, Drugs in Context, 2013, p. 212256.
Scheen, Efficacy and Safety of Jentadueto, Expert Opinion on Drug and Safety, vol. 12, No. 2, 2013, p. 275-289.
Haak, Initial Combination of linagliptin and metformin improves glycemic control in type 2 diabetes, Diabetes, Obesity and Metabolism, vol. 14, 2012, p. 565-574.
International Search Report and Written Opinion for PCT/EP2017/064007, dated Jun. 8, 2017.
Wikipedia, the free encyclopedia, The carbonyl group, 2017.
Controlling Temperature (Guidelines for the Storage of Essential Medicines and Other Health Commodities, 2003, http://apps.who.int.medicinedocs/en/d/Js4885e/6.5html).
Pharmaceutical Manufacturing and Storage (Concepts and Design, Inc.) 2009.

"Betahistine diHCL CF 16 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,57626>.
"Betahistine diHCL CF 8 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,56227>.
"Sifrol 0,088 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70120>.
"Sifrol 0,18 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70121>.
"Sifrol 0,35 mg, tabletten," Dutch Medicines Evaluation Board, Dated Nov. 16, 1999, Retrieved online from: <http://db.cbg-meb.nl/ords/f?p=111:3:0:SEARCH:NO::P0_DOMAIN,P0_LANG,P3_RVG1:H,EN,70673>.
"Sifrol 0,70 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70122>.
"Sifrol 1,1 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70124>.
Abstract for AU 2003280680, Jun. 18, 2004.
Abstract for AU 2009224546, Sep. 17, 2009.
Abstract in English for DE10109021, 2002.
Abstract in English for DE19705233, Aug. 13, 1998.
Abstract in English for DE2205815, 1972.
Abstract in English for EP0023032, 1981.
Abstract in English for JP 2002/348279, Dec. 4, 2002.
Abstract in English for JP 2003/286287, Oct. 10, 2003.
Abstract in English for KR20070111099, Nov. 11, 2007.
ACTOS Prescribing Information, 1999, pp. 1-26.
Adebowale, K.O. et al., "Modification and properties of African yam bean (Sphenostylis stenocarpa Hochst. Ex A. Rich.) Harms starch I: Heat moisture treatments and annealing." Food Hydrocolloids, 2009, vol. 23, No. 7, pp. 1947-1957.
Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.
Ahren, Bo "Novel combination treatment of type 2 diabetes DPP-4 inhibition + metformin." Vascular Health and Risk Management, 2008, vol. 4, No. 2, pp. 383-394.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
American Association of Clinical Endocrinologists, "Medical Guidelines for Clinical Practice for the Management of Diabetes Mellitus." Endocrine Practice, 2007, col. 13, Suppl. 1, pp. 1-68.
American Diabetes Association, "Standards of Medical Care in Diabetes—2008." Diabetes Care, Jan. 2008, vol. 31, Supplement 1, pp. S12-S54.

(56) References Cited

OTHER PUBLICATIONS

Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Aulton, Michael E., Pharmaceutics: The Science of Dosage Form Design, Second Edition, 2002, pp. 441-448.
Baetta, R. et al., "Pharmacology of Dipeptidyl Peptidase-4 Inhibitors." Drugs, 2011, vol. 71, No. 11, pp. 1441-1467.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates the 100 mg-approach." International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Banker, Gilbert S., "Prodrugs." Modern Pharmaceutics Third Edition, Marcel Dekker, Inc., 1996, p. 596.
Bastin, R.J. et al., "Salt Selection and Optimization Procedures for Pharmaceutical New Chemical Entities". Organic Process Research and Development, 2000, vol. 4, p. 427-435.
Beauglehole, Anthony R., "N3-Substituted Xanthines as Irreversible Adenosine Receptor Antagonists." Ph.D. Thesis, Deakin University, Australia, 2000, pp. 1-168.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.

Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
International Search Report—European Search Report for PCT/EP2003/09127 dated Mar. 1, 2011.
International Search Report and Written Opinion for PCT/EP2006/064657 dated Nov. 2, 2006.
International Search Report and Written Opinion for PCT/EP2007/054201 dated Aug. 29, 2007.
International Search Report and Written Opinion for PCT/EP2007/054270 dated Aug. 14, 2007.
International Search Report and Written Opinion for PCT/EP2008/060740 dated Mar. 30, 2009.
International Search Report and Written Opinion for PCT/EP2009/053978 dated Sep. 29, 2009.
International Search Report and Written Opinion for PCT/EP2009/056722 dated Aug. 13, 2009.
International Search Report and Written Opinion for PCT/EP2009/060521 dated Mar. 9, 2010.
International Search Report and Written Opinion for PCT/EP2009/063511 dated Feb. 26, 2010.
International Search Report and Written Opinion for PCT/EP2009/067772 dated Apr. 14, 2010.
International Search Report and Written Opinion for PCT/EP2010/050103 dated Mar. 22, 2010.
International Search Report and Written Opinion for PCT/EP2010/051093 dated Jul. 14, 2010.
International Search Report and Written Opinion for PCT/EP2010/051817 dated Jun. 8, 2010.
International Search Report and Written Opinion for PCT/EP2010/064691 dated Apr. 6, 2011.
International Search Report and Written Opinion for PCT/EP2010068349 dated Feb. 4, 2011.
International Search Report and Written Opinion for PCT/EP2011/054169 dated Aug. 4, 2011.
International Search Report and Written Opinion for PCT/EP2011/057163 dated Jun. 27, 2011.
International Search Report and Written Opinion for PCT/EP2011/057256 dated Jul. 22, 2011.
International Search Report and Written Opinion for PCT/EP2011/060449 dated Sep. 27, 2011.
International Search Report and Written Opinion for PCT/EP2011/070156 dated Jan. 17, 2012.
International Search Report and Written Opinion for PCT/EP2012/053910 dated May 14, 2012.
International Search Report and Written Opinion for PCT/EP2012/063852 dated Sep. 6, 2012.
International Search Report and Written Opinion for PCT/EP2012/077024 dated Feb. 19, 2013.
International Search Report and Written Opinion for PCT/EP2013/054524 dated Apr. 24, 2013.
International Search Report and Written Opinion for PCT/EP2013/059828 dated Aug. 6, 2013.
International Search Report and Written Opinion for PCT/EP2013/059831 dated Aug. 9, 2013.
International Search Report and Written Opinion for PCT/EP2013/060311 dated Aug. 9, 2013.
International Search Report and Written Opinion for PCT/EP2013/060312 dated Sep. 4, 2013.
International Search Report and Written Opinion for PCT/EP2013/070978 dated Oct. 31, 2013.
International Search Report and Written Opinion for PCT/EP2014/055113 dated May 16, 2014.
International Search Report and Written Opinion for PCT/EP2014/062398 dated Aug. 20, 2014.

(56) References Cited

OTHER PUBLICATIONS

International Search Report and Written Opinion for PCT/EP2015/054114 dated May 12, 2015.
International Search Report and Written Opinion for PCT/EP2015/074030 dated Feb. 4, 2016.
International Search Report and Written Opinon for PCT/EP2007/054204 dated Aug. 3, 2007.
International Search Report for PCT/EP03/12821 dated Mar. 30, 2004.
International Search Report for PCT/EP03/13648 dated Apr. 5, 2004.
International Search Report for PCT/EP2002/01820 dated May 7, 2002.
International Search Report for PCT/EP2003/12821 dated Mar. 30, 2004.
International Search Report for PCT/EP2003/13648 dated Apr. 5, 2004.
International Search Report for PCT/EP2005/001427 dated May 23, 2005.
International Search Report for PCT/EP2005/055711 dated Mar. 29, 2006.
International Search Report for PCT/EP2007/054204 dated Mar. 8, 2007.
International Search Report for PCT/EP2007/058181 dated Nov. 28, 2007.
International Search Report for PCT/EP2008/060738 dated Nov. 5, 2008.
International Search Report for PCT/EP2009/060170 dated Oct. 28, 2009.
International Search Report for PCT/EP2010/064691 dated Jan. 20, 2011.
International Search Report for PCT/EP2013/060309 dated Aug. 9, 2013.
International Search Report for PCT/EP2013/070979 dated Nov. 26, 2013.
International Search Report for PCT/EP2014/060160 dated Nov. 8, 2014.
Schnapp, G. et al., "Comparative Enzyme Kinetic Analysis of the Launched DPP-4 Inhibitors." American Diabetes Association, Abstract 1048-P, 2014.
Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion, EMEA, Pramipexole, 2005, pp. 1-10.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4c36-a142-848ac068c405&mKey=2dbfcaf7-1539-42d5-8dda-0a94abb089e8>.
Sheperd, Todd M. et al., "Efective management of obesity." The Journal of Family Practice, 2003, vol. 52, No. 1, pp. 34-42.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L. et al., "Transcription Factor 7-Like 2 Regulates B-Cell Survival and Function in Human Pancreatic Islets." Diabetes, 2008, vol. 57, pp. 645-653.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.
Singhal, D. et al., "Drug polymorphism and dosage form design: a practical perspective." Advanced Drug Delivery Reviews, 2004, vol. 56, pp. 335-347.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, P.H., "Handbook of Pharmaceutical Salts" C.G. Wermuth, Wiley-VCH, 2002, pp. 1-374.
Standl, E. et al., "Diabetes and the Heart." Diabetes Guidelines (DDG), 2002, pp. 1-25.
Sulkin, T.V. et al., "Contraindications to Metformin Therapy in Patients With NIDDM." Diabetes Care, 1997, vol. 20, No. 6, pp. 925-928.
Sune Negre, J. M. "New Galenic Contributions to Administration Forma". Continued Training for Hospital Pharmacists 3.2., (Publication date unavailable), Retrieved from internet on Feb. 23, 2011, http://www.ub.es/legmh/capitols/sunyenegre.pdf.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Tadayyon, M. et al., "Insulin sensitisation in the treatment of Type 2 diabetes." Expert Opinion Investigative Drugs, 2003, vol. 12, No. 3, pp. 307-324.
Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.
Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S.. et al; "Suppression of Arthritis by the Inhibitors of Dipeptidyl Peptidase IV," In. J. Immunopharmac., vol. 19, No. 1, pp. 15-24, 1997.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.
Third Party Observation for application No. EP20070728655, May 13, 2013.
Thomas, L. et al, "BI 1356, a novel and selective xanthine beased DPP-IV inhibitor, exhibits a superior profile when compared to sitagliptin and vildagliptin." Diabetologia, 2007, vol. 50, No. Suppl. 1, p. S363.

(56) References Cited

OTHER PUBLICATIONS

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors." Journal of Pharmacology and Experimental Therapeutics, 2008, vol. 325, No. 1, pp. 175-182.

Thornber, C.W., "Isosterism and Molecular Modification in Drug Design." Chemical Society Reviews, 1979, pp. 563-580.

Tounyoubyou, "Symposium-19: Future Perspectives on Incretion Therapy in Diabetes." 2008, vol. 51, Suppl. 1, p. S-71, S19-2.

Tradjenta, Highlights of Prescribing Information (revised Sep. 2012).

Tribulova, N. et al. "Chronic Disturbances in NO Production Results in Histochemical and Subcellular Alterations of the Rat Heart." Physiol. Res., 2000, vol. 49, No. 1, pp. 77-88.

Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573-fe45-4c2f-9485-6270854fc10b&cKey=3c387569-04de-4f8c-b025-b358df91ca64&mKey=%7b89918D6D-3018-4EA9-9D4F-711F98A7AE5D%7d>.

Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

United Healthcare, "Diabetes." Retrieved from internet on Aug. 22, 2013, http://www.uhc.com/source4women/health_topics/diabetesirelatedinformation/dOf0417b073bf11OVgnVCM1000002f1Ob1Oa _. htm.

Van Heek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.

Vichayanrat, A. et al., "Efficacy and safety of voglibose in comparison with acarbose in type 2 diabetic patients." Diabetes Research and Clinical Practice, 2002, vol. 55, pp. 99-103.

Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Vincent, S.H. et al., "Metabolism and Excretion of the Dipeptidyl Peptidase 4 Inhibitor [14C]Sitagliptin in Humans." Drug Metabolism and Disposition, 2007, vol. 35, No. 4, pp. 533-538.

Wang, Y. et al., "BI-1356. Dipeptidyl-Peptidase IV Inhibitor, Antidiabetic Agent." Drugs of the Future, 2008, vol. 33, No. 6, pp. 473-477.

Weber, Ann E., "Dipeptidyl Peptidase IV Inhibitors for the Treatment of Diabetes." Journal of Medicinal Chemistry, 2004, vol. 47, pp. 4135-4141.

WebMD, Autoimmune Diseases: What are They? Who Gets Them? "What Are Autoimmune Disorders?" 2015, pp. 1-3. Retrieved online Jul. 9, 2015. http://www.webmd.com/a-to-z-guides/autoimmune-diseases.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.

Dave, Rutesh H. "Overview of pharmaceutical excipients used in tablets and capsules." Drug Topics, Oct. 24, 2008.

Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.

Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.

Definition of "prevent", e-dictionary, Aug. 15, 2013, http://dictionary.reference.com/browse/prevent.

DeMeester, I. et al.; "CD26, let it cut or cut it down", Review: Immunology Today; Aug. 1999, vol. 20, No. 8 pp. 367-375.

Demuth, H-U. et al., "Type 2 diabetes—Therapy with dipeptidyl peptidase IV inhibitors". Biochimica et Biophysica Acta, vol. 1751(1), 2005, p. 33-44.

Diabetes Frontier, 2007, vol. 18, No. 2, p. 145-148.

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.

Diabetesincontrol.com "EASD: Eucreas, a Combination of Galvus and Metformin, Recommended for Approval." Diabetes in Control. com, Sep. 25, 2007, Retrieved from internet on Nov. 30, 2012, http://www.diabetesincontrol.com/articles/53-diabetes-news/5145.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

Dittberner, S. et al., "Determination of the absolute bioavailability of BI 1356, a substance with non-linear pharmacokinetics, using a population pharmacokinetic modeling approach." Abstracts of the Annual Meeting of the Population Approach Group in Europe, 2007.

Drucker, Daniel J., "Dipeptidyl Peptidase-4 Inhibition and the Treatment of Type 2 Diabetes." Diabetes Care, 2007, vol. 30, No. 6, pp. 1335-1343.

Drucker, et al.., The incretin system:glucagon-like peptide-1 receptor agonists and dipeptidyl peptidase-4 inhibitors in type 2 diabetes. Lancet, 2006, 368: 1696-705.

Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.

(56) References Cited

OTHER PUBLICATIONS

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.
Dunitz, J. et al., "Disappearing Polymorphs." Acc. Chem. Res. 1995, vol. 28, No. 4, pp. 193-200.
Eckhardt Matthias et al: 8-(3-(R)-aminopiperidin-1-yl)-7-but-2-yny 1-3-methyl-1-(4-methyl-quinazolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.
Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
Edosada, C.Y. et al "Selective Inhibition of Fibroblast Activation Protein Protease Based on Dipeptide Substrate Specificity." The Journal of Biological Chemistry, 2006, vol. 281, No. 11, pp. 7437-7444.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
EMEA: European Medicines Agency, "Galvus (vildagliptin)" Retrieved online on Jan. 21, 2016.
EMEA: European Medicines Agency, ICH Topic E4, "Dose Response Information to Support Drug Registration." 1994 pp. 1-10.
Eucreas Scientific Discussion, 2007, p. 1-27, www.emea.europa.eu/humandocs/PD/Fs/EPAR/eucreas/H-807-en6.pdf, Anonymous.
European Search Report for EP 08 15 9141 dated Apr. 6, 2009 (European counterpart of U.S. Appl. No. 12/143,128).
Eyjolfsson, Reynir "Lisinopril-Lactose Incompatibility." Drug Development and Industrial Pharmacy, 1998, vol. 24, No. 8, pp. 797-798.
Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Ferry, Robert Jr., "Diabetes Causes." eMedicine Health, MedicineNet.com, 2013, Retrieved from internet on Aug. 22, 2013,<http://www.onhealth.com/diabetes_health/page3.htm#diabetes_causes>.
Flatt, P.R. et al., "Dipeptidyl peptidase IV (DPP IV) and related molecules in type 2 diabetes." Frontiers in Bioscience, 2008, vol. 13, pp. 3648-3660.
Florez, J. et al. "TCF7L2 Polymorphisms and Progression to Diabetes in the Diabetes Prevention Program." The New England Journal of Medicine, 2006, vol. 355, No. 3, pp. 241-250.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Fukushima et al., Drug for Treating Type II Diabetes (6), "action-mechanism of DPP-IV inhibitor and the availability thereof" Mebio, 2009, vol. 26, No. 8, p. 50-58.
Gall, "Prevalence of micro-and macroalbuminuria, arterial hypertension, retinopathy and large vessel disease in European type 2 (non-insulin dependent) diabetic patients", Diabetologia (1991) 655-661.

Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". IDRUGS, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Galvus (Vildagliptin) Scientific Discussion, EMEA, 2007, pp. 1-34.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Wertheimer, et al., "Drug Delivery Systems improve pharmaceutical profile and faciliate medication adherence", Adv. Therapy 22: p. 559-577 (2005).
White, John R. Jr., "Dipeptidyl Peptidase-IV Inhibitors: Phamacological Profile and Clinical Use". Clinical Diabetes, Apr. 2008, vol. 26, No. 2, pp. 53-57.
Wikipedia, "Linagliptin" Sep. 12, 2015. <https://en.wikipedia.org/w/index.php?title=Linagliptin&oldid=333469979>.
Wikipedia, Annulation. Jun. 23, 2008, http://en.wikipedia.org/wiki/Annelation.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Wirth, D. et al., "Maillard Reaction of Lactose and Fluoxetine Hydrochloride, a Secondary Amine." Journal of Pharmaceutical Sciences, 1998, vol. 87, No. 1, pp. 31-39.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.

(56) References Cited

OTHER PUBLICATIONS

Yap, W.S. et al., "Review of management of type 2 diabetes mellitus." Journal of Clinical Pharmacy and Therapeutics, 1998, vol. 23, pp. 457-465.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Yoshioka, S. et al., "Stability of Drugs and Dosage Forms." Kluwer Academic Publishers, 2002, pp. 30-33.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zander, M. et al., "Additive Glucose-Lowering Effects of Glucagon-Like Peptide-1 and Metformin in Type 2 Diabetes." Diabetes Care, 2001, vol. 24, No. 4, pp. 720-725.
Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.
Zejc, Alfred, et al; "Badania Nad Piperazynowymi Pochodnymi Dwumetyloksantyn" Acta Polon Pharm, XXXV (1976) Nr. 4 pp. 417-421.
Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.
Zhimei, Xiao et al., "Study progression of oral drugs for treatment of type II diabetes." Drug Evaluation, 2004, vol. 1, No. 2, pp. 138-143.
Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Rosenstock, J. et al., "Triple Therapy in Type 2 Diabetes." Diabetes Care, 2006, vol. 29, No. 3, pp. 554-559.
Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.
EMEA Guidelines on Galvus®, 2007, pp. 1-34.
EMEA Guidelines on Eucreas®, 2007, pp. 1-27.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.
U.S. Appl. No. 15/235,575, filed Aug. 12, 2016, Inventor: Klaus Dugi.
Kishore, Preeti MD., "Complications of Diabetes Mellitus." Merck Manual Consumer Version, 2016, pp. 1-7.
Fantus, George, "Metformin's contraindications: needed for now." Canadian Medical Association Journal, 2005, vol. 173, No. 5, pp. 505-507.
EU Clinical Trial Register, "A multicenter, international, rendomized, parallel group, double-blind, placebo-controlled, cardiovascular safety and renal microvascular outcome study with linagliptin, 5 mg once daily in patients with type 2 diabetes mellitus at high vascular risk." Aug. 19, 2015.
Fiorucci, et al. Trends in Molecular Medicine, Targeting farnesoid X receptor for liver and metabolic disorders, 13(7), 2007, p. 298-309.
Morhenn, "Keratinacyte proliferation n wound healing and skin diseases", Immunology Today, vol. 9, Issue 4, 1988, p. 104.
Karaliede et al, Diabetes Care, Endothelial Factors and Diabetic Nephropathy, 2011, 34, Suppl 2, p. 291-296.
Inukai, T., "Treatment of Diabetes in Patients for Whom Metformin Treatment is Not Appropriate." Modem Physician, 2008, vol. 28, No. 2, pp. 163-165.
Inzucchi, Silvio E., "Oral Antihyperglycemic Therapy for Type 2 Diabetes." The Journal of the American Medical Association, 2002, vol. 287, No. 3, pp. 360-372.
Isomaa, B. et al., "Cardiovascular Morbidity and Mortality Associated With the Metabolic Syndrome." Diabetes Care, 2001, vol. 24, No. 4, pp. 683-689.
Iwamoto, Yasuhiko, "Insulin Glargine." Nippon Rinsho, 2002, vol. 60, Suppl. 9, pp. 503-515.
Janumet Prescribing Information, revised Jan. 2008.
Januvia Medication Guide, 2010.
Januvia Prescribing Information and Product Label, 2006.
Januvia, 25mg, 50mg, 100 mg, Summary of Product Characteristics, 2015, www.medicines.org.uk/EMC <http://www.medicines.org.uk/EMC>.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
John Hopkins Children's Center, "Liver Disorders and Diseases." Retrieved online May 26, 2014 <http://www.hopkinschildrens.org/non-alcoholic-fatty-liver-disease.aspx>.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
Kelly. T., "Fibroblast activation protein-cx and dipeptidyl peptidase IV (CD26)P: Cell-surface proteases that activate cell signaling and are potential targets for cancern therapy". Drug Resistence Update 8, 2005, vol. 8. No. 1-2, pp. 51-58.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Kharkevich, D. A., "Educational Literature" Pharmacology (1987) Third Edition, Meditsina Press, Moscow pp. 47-48.
Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.

(56) References Cited

OTHER PUBLICATIONS

Kim, D. et al., "(2R)-4-Oxo-4-(3-(Trifluoromethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Kim, Kwang-Rok et al., "KR-62436, 6-{2-{2-(5-cyano4,5-dihydropyrazol-1-yl)-2-oxoethylamino}ethylamino}nicotinonitrile, is a novel dipeptidyl peptidase-IV (DDP-IV) inhibitor with antihyperglycemic activity" European Journal of Pharmacology 518, 2005, p. 63-70.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Klein, T. et al., "Linagliptin alleviates hepatic steatosis and inflammation in a mouse model of non-alcoholic steatohepatitis." Medical Molecular Morphology, 2014, vol. 47, pp. 137-149.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Komori, Kiyoshi., "Treatment of Diabetes in Patients for Whom Metforming Treatment is not Appropriate" Modern Physician (2008) vol. 28, No. 2 pp. 163-165.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
Kumar, V. et al., "Maillard Reaction and Drug Stability." Maillard Reactions in Chemistry, Food, and Health, 1994, No. 151, pp. 20-27.
Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.
Lachman, L. et al., "The Theory and Practice of Industrial Pharmacy." Varghese Publishing House, Third Edition, 1987, pp. 190-194.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.
Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
Lee Jones, K. et al., "Effect of Metformin in Pediatric Patients With Type 2 Diabetes." Diabetes Care, 2002, vol. 25, No. 1, pp. 89-94.
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Levien,T.L. et al, "New drugs in development for the treatment of diabetes", Diabetes Spectrum, American Diabetes Association, US, vol. 22, No. 2, Jan. 1, 2009, pp. 92-106.
Lieberman, H. et al., "Pharmaceutical Dosage Forms." Marcel Dekker, Inc., 1980, vol. 1, p. 38.
Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
Linagliptin Monograph, Published by VACO PBM-SHG US Veteran's Administration, 2011, pp. 1-17.
Lindsay, J.R. et al., "Inhibition of dipeptidyl peptidase IV activity by oral metformin in Type 2 diabetes." Diabetic Medicine, 2005, vol. 22, pp. 654-657.
Lovshin, J.A. et al., "Incretin-based therapies for type 2 diabetes mellitus." Nature Reviews Endocrinology, 2009, vol. 5, pp. 262-269.
Lu, "High prevlaence of albuminuria in population based patients diagnosed with type 2 diabetes in the Shanghai downtown", Diabestes Research and Clinical Practice (2007) 184-192.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
March, J. "Advanced Organic Chemistry: Reactions, Mechanisms, and Structure". Fourth Edition, 1992, pp. 652-653.
Mathieu, C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.
Matsumiya, Teruhiko, et al., "Therapeutic Drugs for Clinicians" Diagnosis and Treatment (2008) vol. 96, No. 2 pp. 389-390.
Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.
McNay, David E.G. et al., "High fat diet causes rebound weight gain." Molecular Metabolism, 2013, vol. 2, pp. 103-108.
Methocel Cellulose Ethers in Aqueous Systems for tablet coating: retrieved from Internet: http;//msdssearch.dow.com/PublishedLiteratureDOWCOM/dh_004a/0901b8038004ab56.pdf?filepath=198-00755.pd?fromPage=GetDoc, published2002. Retrieved Dec. 8, 2017.
Wu, Reactive Impurities in Excipients-Profiling, American Association of Pharmaceutical Scientists, 2011, vol. 12, No. 4, p. 1248-1263.
Waterman, Accelerating aging-Prediction of Chemical Stability of Pharmaceuticals, International Journal of Pharmaceutics, 2005, vol. 293, p. 101-125.
Herman, The DP-IV inhibitor MK-0431 enhances active GLP-1 and reduces Glucose following an OGTT in Type 2 Diabetics, American Diabetes Asociation, 2004.
Kaur, Development of new incretin drugs: Promising Therapies, Indian Journal Pharmacology, 2006, vol. 38, Issue 2, p. 100-106.
Hu, Diabetes Mellitus and Cardiovascular Disease, Peoples Military Medical Press, 2005, p. 211.
Susman,Ada: Linagliptin Works in Diabetic Kidney Disease, Med Page Today, 2011.
Announcement of the approval of Novel oral Diabetes Drug JANUVIA, Press Release, 2006.
Okano, Renal Clearance, New General Pharmaceutics, Revised 3rd Edition, 1987p. 213-215.
Clinical trials, A Randomized, Double Blind, Active Controlled parallel Group Efficacy and Safety Study of BI 1356 Compared to Glimepiride over 2 years in Type 2 Diabetic Patients with insufficient glycemic control despite metformin therapy, https://clinicaltrials.gov/archive/NCT00622284/20120606, 2008.
Eckhardt, "-(3-(R)-Aminopiperidin-1-yl)7-but-2-ynyl-3-methyl-1-(4-methyl-quinazolin-2-ylmethyl-3,7-dihydropurine-2,6-dione (BI 1356), a highly potent, selective, long-acting, and orally bioavailable DPP-4 inhibitor for the treatment of type 2 diabetes", J. med. Chem, vol. 50, 2007.
Shigai, "How to use medicines in case of kidney injury caused by medicine" Journal of the Japanese Association of Rural Medicine, vol. 51, 2002, p. 63-67.

(56) References Cited

OTHER PUBLICATIONS

Zeng, "Efficacy and Safety of linagliptin added to metformin and sulphonylurea in Chinese patients with type 2 diabetes: a sub-analysis of data from a randomised clinicial trial", Current Medical Research and Opinion, 2013.

Seino, Alogliptin plus voglibose in Japanese patients witrh type 2 diabetes: a randomized, double blind, placebo-controlled trial with an open label, long term extension, Current Medical Research and Opinion, 2011, vol. 27, p. 21-29.

Kurozumi, Efficacy of a-glucosidase inhibitors combined with dipeptyl-peptidase-4 inhibitor for glucose fluctuation in patients with type 2 diabetes mellitus by continuous glucose monitoring, Journal of Diabetes Investigation, 2013, vol. 4, p. 393-398.

Horikawa, Synergistic Efffect of a-glucosidase inhibitors and dipeptidyl peptidase 4 inhibitor treatment, Journal of Diabetes Investigation, 2011, vol. 2, p. 200-203.

Yamazaki, Comparison of Efficacies of a Dipeptidyl Peptidase IV Inhibitor and a-Glucosodase Inhibitors in Oral Carbohydrate and Meal Tolerance Tests and their Effects of their tolerance in mice, J. Pharmacol Science, 2007, p. 29-38.

Kawamori, Linagliptin monotherapy provides superior glycaemic control v. placebo or voglibose with comparable safety in Japanese patients with type 2 diabetes, a randomized, placebo and active comparator-controlled doiuble blind study, 2011, Diabetes, Obesity and Metabolism, p. 348-357.

Inagaki, Linagliptin provides effective, well-tolerated add-on therapy to pre-existing oral antidiabetic therapy over 1 year in Japanese patients with type 2 diabetes, Diabetes, Obesity and Metabolis, 2013, p. 833-843.

TREATMENT OF GENOTYPED DIABETIC PATIENTS WITH DPP-IV INHIBITORS SUCH AS LINAGLIPTIN

FIELD OF THE INVENTION

The invention describes DPP-4 inhibitors, pharmaceutical compositions or combinations comprising a DPP-4 inhibitor as defined herein and optionally one or more other active substances, for use in methods of treatment or prevention as described herein, such as e.g. of one or more conditions selected from type 1 diabetes mellitus, type 2 diabetes mellitus, impaired glucose tolerance, impaired fasting blood glucose and hyperglycemia inter alia. In a particular embodiment, the therapeutic and/or preventive methods of this invention comprise the step of identifying a patient being susceptible to the treatment and/or prevention, said identifying comprising testing whether the patient has variation(s) in one or more genes associated with metabolic diseases (e.g. whether the patient is of a TCF7L2 risk genotype as described herein) or whether the patient is of respective wild-type genotype (e.g. whether the patient is of TCF7L2 wild genotype as described herein), and the further step of administering such DPP-4 inhibitor, pharmaceutical composition or combination to the patient determined as being susceptible.

BACKGROUND OF THE INVENTION

Type 2 diabetes is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a two to five fold increase in cardiovascular disease risk.

After long duration of disease, most patients with type 2 diabetes will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c ~0.9%). In addition, even in patients within the intensive treatment arm glycemic control deteriorated significantly over time and this was attributed to deterioration of β-cell function. Importantly, intensive treatment was not associated with a significant reduction in macrovascular complications, i.e. cardiovascular events. Therefore many patients with type 2 diabetes remain inadequately treated, partly because of limitations in long term efficacy, tolerability and dosing inconvenience of existing antihyperglycemic therapies.

Oral and non-oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides, α-glucosidase inhibitors, GLP-1 or GLP-1 analogues, and insulin or insulin analogues.

The high incidence of therapeutic failure is a major contributor to the high rate of long-term hyperglycemia-associated complications or chronic damages (including micro- and makrovascular complications such as e.g. diabetic nephrophathy, retinopathy or neuropathy, or cardiovascular complications) in patients with type 2 diabetes.

Genetic association studies have identified genetic variations in several genes which are associated with increased risk of type 2 diabetes mellitus. E.g. variations in the genes TCF7L2, KCNJ11 and PPARG independently and interactively increase the risk of progression from impaired fasting glucose and impaired glucose tolerance to overt diabetes. While variation in KCNJ11 may alter insulin secretion and variation in PPARG may alter insulin action, TCF7L2 (transcription factor 7-like 2) is the major susceptibility gene identified to date for type 2 diabetes in various ethnic groups (e.g. Europeans, Indian and Japanese people, Mexican Americans and West Africans). Polymorphisms (single nucleotid polymorphisms, so called SNPs) in TCF7L2, such as e.g. rs12255372 and, particularly, rs7903146, are strongly associated with diabetes. The risk of developing type 2 diabetes is increased by roughly 45% (Odds ratio 1.45) among carriers of one risk T-allele of TCF7L2 rs7903146 (CT heterozygotes), and is at least doubled (Odds ratio of 2.41) among TT homozygotes compared to CC homozygotes wild genotypes (Grant et al, Nature Genetics, Vol. 38, 2006, p 320-323). TCF7L2 risk genotypes are associated with increased TCF7L2 expression in pancreatic beta cells, impaired (glucose-stimulated) insulin secretion, incretin effects and enhanced rate of hepatic glucose production as well as predisposition to and prediction of future type 2 diabetes (cf. Lyssenko et al., The Journal of Clinical Investigation, Vol. 117, No 8, 2007, p. 2155-2163). There is evidence that the TCF7L2 rs7903146 risk variants are associated with lower incretin effect on insulin secretion, which may be based, at least in parts, on an impaired sensitivity of the beta cells to incretins.

Thus, diabetes patients harboring TCF7L2 risk variants, particularly carriers of the at risk T-allele of TCF7L2 rs7903146, such as patients harboring the TCF7L2 rs7903146 CT genotype or, particularly, patients harboring the TCF7L2 rs7903146 TT genotype, are expected to be difficult to treat in antidiabetic therapy.

Therefore, there is an unmet medical need for methods, medicaments and pharmaceutical compositions or combinations with a good efficacy with regard to glycemic control, with regard to disease-modifying properties and with regard to reduction of cardiovascular morbidity and mortality while at the same time showing an improved safety profile.

DPP-4 inhibitors represent another novel class of agents that are being developed for the treatment or improvement in glycemic control in patients with type 2 diabetes.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/128721, WO 2007/128724, WO 2007/128761, or WO 2009/121945.

The aim of the present invention is to provide a medication and/or method for preventing, slowing progression of, delaying or treating a metabolic disorder, in particular of type 2 diabetes mellitus.

A further aim of the present invention is to provide a medication and/or method for improving glycemic control in a patient in need thereof, in particular in patients with type 2 diabetes mellitus, for example in those patients who have variation(s) in one or more genes associated with metabolic diseases (such as e.g. a TCF7L2 risk genotype patient as described herein) or in those patients who are of respective wild-type genotype.

Another aim of the present invention is to provide a medication and/or method for improving glycemic control in a patient with insufficient glycemic control despite monotherapy with an antidiabetic drug, for example metformin, or despite combination therapy with two or three antidiabetic drugs, for example in such a patient who has variation(s) in one or more genes associated with metabolic diseases (such as e.g. a TCF7L2 risk genotype patient as described herein) or in such a patient who is of respective wild-type genotype.

Another aim of the present invention is to provide a medication and/or method for preventing, slowing or delaying progression from impaired glucose tolerance (IGT), impaired fasting blood glucose (IFG), insulin resistance and/or metabolic syndrome to type 2 diabetes mellitus.

Yet another aim of the present invention is to provide a medication and/or method for preventing, slowing progression of, delaying or treating of a condition or disorder from the group consisting of complications of diabetes mellitus.

A further aim of the present invention is to provide a medication and/or method for reducing the weight or preventing an increase of the weight in a patient in need thereof, for example in such a patient who has variation(s) in one or more genes associated with metabolic diseases (such as e.g. a TCF7L2 risk genotype patient as described herein) or in such a patient who is of respective wild-type genotype.

Another aim of the present invention is to provide a medication with a high efficacy for the treatment of metabolic disorders, in particular of diabetes mellitus, impaired glucose tolerance (IGT), impaired fasting blood glucose (IFG), and/or hyperglycemia, which has good to very good pharmacological and/or pharmacokinetic and/or physicochemical properties.

Further aims of the present invention become apparent to the one skilled in the art by description hereinbefore and in the following and by the examples.

SUMMARY OF THE INVENTION

Within the scope of the present invention it has now been found that a DPP-4 inhibitor, preferably linagliptin, as well as a pharmaceutical composition or combination comprising the DPP-4 inhibitor and optionally one or more other active substances (e.g. antidiabetics), is therapeutically effective for improving glycemic control and treating type 2 diabetes mellitus in TCF7L2 rs7903146 CT or TT risk genotype patients and in TCF7L2 rs7903146 CC wild genotype patients.

In particular, it has been found that all investigated TCF7L2 genotype patients (patients with TCF7L2 rs7903146 CT or TT risk genotype or with TCF7L2 rs7903146 CC wild genotype) have a clinically meaningful response to the administered DPP-4 inhibitor, preferably linagliptin.

Thus, within the scope of the present invention, certain subgroups of diabetes patients amenable to antidiabetic therapy according to this invention (comprising using preferably linagliptin, optionally in combination with one or more other active substances such as e.g. other antidiabetics as described herein), include for example, without being limited to, those patients harboring TCF7L2 rs7903146 CC or CT or TT genotype, respectively.

Within the scope of the present invention it has further been found that DPP-4 inhibitors as defined herein as well as pharmaceutical compositions or combinations comprising a DPP-4 inhibitor as defined herein and optionally one or more other active substances can be used in a method of preventing, slowing progression of, delaying (e.g. delaying the onset of) or treating a metabolic disorder (particularly diabetes, especially type 2 diabetes mellitus and conditions related thereto, e.g. diabetic complications), in particular a method for improving glycemic control in a patient, such as in a patient who has variation(s) in one or more genes associated with metabolic diseases (such as e.g. in TCF7L2 risk genotype patients as described herein).

Within the scope of the present invention it has further been found that DPP-4 inhibitors as defined herein as well as pharmaceutical compositions or combinations comprising a DPP-4 inhibitor as defined herein and optionally one or more other active substances can be used in a method of preventing, slowing progression of, delaying (e.g. delaying the onset of) or treating a metabolic disorder (particularly diabetes, especially type 2 diabetes mellitus and conditions related thereto), in particular a method for improving glycemic control in a patient, such as in a patient who is of TCF7L2 wild genotype, particularly of TCF7L2 rs7903146 CC wild genotype.

Further, in one embodiment, the usability of a DPP-4 inhibitor, a pharmaceutical composition, combination or medicament each as described herein for a therapeutic and/or preventive method or use according this invention in a patient who has variation(s) in one or more genes associated with metabolic diseases (such as e.g. a TCF7L2 risk genotype patient as described herein) is contemplated.

TCF7L2 risk genotype patients according to this invention include, without being limited, patients (particularly type 2 diabetes patients) harboring genetic risk variants in the gene TCF7L2 and suffering often from the pathological influences thereof, particularly associated with the risk T-allele of TCF7L2 rs7903146, such as patients harboring the TCF7L2 rs7903146 CT heterozygous risk genotype or patients harboring the TCF7L2 rs7903146 TT homozygous high risk genotype.

Further, in another embodiment, the usability of a DPP-4 inhibitor, a pharmaceutical composition, combination or medicament each as described herein for a therapeutic and/or preventive method or use according this invention in a patient who carries the TCF7L2 wild genotype, particularly the TCF7L2 rs7903146 CC wild genotype, is contemplated.

Moreover, the present invention provides a diagnostic method for identifying a subject (particularly a type 2 diabetes patient) statistically more likely to have a favorable response (e.g. in achieving glycemic control, such as change in HbA1c) to the administration of a therapeutically effective amount of a DPP-4 inhibitor, optionally in combination with one or more other active substances (e.g. antidiabetics), said method comprising determining whether the subject is either of TCF7L2 risk genotype (particularly TCF7L2 rs7903146 CT or TT risk genotype) or of TCF7L2 wild genotype (particularly TCF7L2 rs7903146 CC wild genotype), wherein the subject being of TCF7L2 rs7903146 CC homozygous wild genotype (and, to a lesser extent, the subject being of TCF7L2 rs7903146 CT heterozygous risk genotype) has an increased likelihood of favorable response to the administered DPP-4 inhibitor relative to a subject of TCF7L2 rs7903146 TT homozygous risk genotype.

Furthermore the invention describes a method
   for preventing, slowing progression of, delaying, or treating a metabolic disorder;

for improving glycemic control and/or for reducing of fasting plasma glucose, of postprandial plasma glucose and/or of glycosylated hemoglobin HbA1c;

for preventing, slowing, delaying or reversing progression from impaired glucose tolerance, impaired fasting blood glucose, insulin resistance and/or from metabolic syndrome to type 2 diabetes mellitus;

for preventing, slowing progression of, delaying or treating of a condition or disorder selected from the group consisting of complications of diabetes mellitus;

for reducing body weight and/or body fat or preventing an increase in body weight and/or body fat or facilitating a reduction in body weight and/or body fat;

for preventing or treating the degeneration of pancreatic beta cells and/or for improving and/or restoring or protecting the functionality of pancreatic beta cells and/or restoring the functionality of pancreatic insulin secretion;

for preventing, slowing, delaying or treating diseases or conditions attributed to an abnormal accumulation of liver or ectopic fat; or for maintaining and/or improving the insulin sensitivity and/or for treating or preventing hyperinsulinemia and/or insulin resistance;

for preventing, slowing progression of, delaying, or treating new onset diabetes after transplantation (NODAT) and/or post-transplant metabolic syndrome (PTMS);

for preventing, delaying, or reducing NODAT and/or PTMS associated complications including micro- and macrovascular diseases and events, graft rejection, infection, and death;

for treating hyperuricemia and hyperuricemia associated conditions;

in patients in need thereof, for example in those patients (particularly type 2 diabetes mellitus patients) who have variation(s) in one or more genes associated with metabolic diseases (such as e.g. in a TCF7L2 risk genotype patient as described herein) or in those patients which are of respective wild-type genotype (such as e.g. in a TCF7L2 wild genotype as described herein), wherein said method comprises testing the patient whether he/she has variation(s) in one or more genes associated with metabolic diseases (e.g. whether he/she is of a TCF7L2 risk genotype as described herein) or whether the patient is of respective wild-type genotype (e.g. whether the patient is of TCF7L2 wild genotype as described herein), and administering a DPP-4 inhibitor as defined hereinafter (preferably linagliptin), optionally in combination with one or more other active substances.

In addition, the present invention describes the use of a DPP-4 inhibitor for the manufacture of a medicament for use in a method as described hereinbefore and hereinafter.

In addition, the present invention describes a DPP-4 inhibitor for use in a therapy of a patient (particularly human type 2 diabetes patient) as described hereinbefore and hereinafter.

In addition, the present invention describes a DPP-4 inhibitor for use in a treatment or prevention of a (particularly metabolic) disease, disorder or condition (particularly diabetes, especially type 2 diabetes, and conditions related thereto, such as e.g. diabetic complications) as described hereinbefore and hereinafter.

The invention also describes a use of a pharmaceutical composition or combination according to this invention for the manufacture of a medicament for use in a method as described hereinbefore and hereinafter.

The invention also relates to the DPP-4 inhibitors as defined herein for use in a method as described hereinbefore and hereinafter, said method comprising administering the DPP-4 inhibitor, optionally in combination with one or more other active substances (e.g. which may selected from those mentioned herein), to the patient.

In an embodiment the method comprises the step of of identifying a patient being susceptible to the method being used, e.g. comprising testing whether the patient has variation(s) in one or more genes associated with metabolic diseases (e.g. whether the patient is of a TCF7L2 risk genotype as described herein) or whether the patient is of TCF7L2 wild genotype as described herein, and the step of administering such a DPP-4 inhibitor, pharmaceutical composition or combination to the patient determined as being susceptible.

This opens up new therapeutic possibilities in the treatment and prevention of type 2 diabetes mellitus, overweight, obesity, complications of diabetes mellitus and of neighboring disease states, including such patients who have variation(s) in one or more genes associated with metabolic diseases (such as e.g. in TCF7L2 risk genotype patients as described herein) and such patients who are of respective wild-type genotype (such as e.g. TCF7L2 wild genotype patients as described herein).

Moreover, the present invention provides a method for determining of a probability of the likelihood of a favorable response (e.g. in providing glycemic control) or the magnitude of a favorable change in HbA1c of an individual resulting from treating the individual with a DPP-4 inhibitor, preferably linagliptin, or the DPP-4 inhibitor in combination with one or more other active substances (e.g. antidiabetics), said method comprising determining whether the subject is either of TCF7L2 risk genotype (particularly TCF7L2 rs7903146 TT risk genotype) or of TCF7L2 wild genotype (particularly TCF7L2 rs7903146 CC wild genotype), wherein the probability of likelihood of a favorable response or the significantly high magnitude of a favorable change in HbA1c response to administration of the DPP-4 inhibitor, preferably linagliptin, or the DPP-4 inhibitor in combination with one or more other active substances (e.g. antidiabetics) is greater in an individual being of TCF7L2 rs7903146 CC homozygous wild genotype, and lower in an individual of TCF7L2 rs7903146 TT homozygous risk genotype (e.g. but still clinically significant or meaningful).

Therefore, in a one aspect there is provided a pharmaceutical composition or combination comprising (a) a DPP-4 inhibitor, and, optionally, (b) a second antidiabetic agent selected from the group G3 consisting of biguanides (particularly metformin), thiazolidindiones, sulfonylureas, glinides, inhibitors of alpha-glucosidase, GLP-1 or GLP-1 analogues and insulin or insulin analogues, and, optionally, (c) a third antidiabetic agent being different from (b) selected from the group G3 consisting of biguanides (particularly metformin), thiazolidindiones, sulfonylureas, glinides, inhibitors of alpha-glucosidase, GLP-1 or GLP-1 analogues and insulin or insulin analogues, or a pharmaceutically acceptable salt thereof.

In a subaspect there is provided a pharmaceutical composition or combination comprising (a) a DPP-4 inhibitor, and, optionally, (b) a second antidiabetic agent selected from the group G3 consisting of biguanides (particularly metformin), thiazolidindiones, sulfonylureas, glinides, inhibitors of alpha-glucosidase, GLP-1 or GLP-1 analogues and insulin or insulin analogues, and, optionally,
(c) a third antidiabetic agent being different from (b) selected from the group consisting of metformin, a sulfonylurea, pioglitazone, rosiglitazone, repaglinide, nateglinide, acarbose, voglibose, miglitol, GLP-1 or a GLP-1 analogue and insulin or an insulin analogue,
or a pharmaceutically acceptable salt thereof.

In another subaspect there is provided a pharmaceutical composition or combination comprising
(a) a DPP-4 inhibitor, and, optionally,
(b) a second antidiabetic agent selected from the group consisting of metformin, a sulfonylurea, pioglitazone, rosiglitazone, repaglinide, nateglinide, acarbose, voglibose, miglitol, GLP-1 or a GLP-1 analogue and insulin or an insulin analogue, and, optionally,
(c) a third antidiabetic agent being different from (b) selected from the group G3 consisting of biguanides (particularly metformin), thiazolidindiones, sulfonylureas, glinides, inhibitors of alpha-glucosidase, GLP-1 or GLP-1 analogues and insulin or insulin analogues,
or a pharmaceutically acceptable salt thereof.

In a further subaspect there is provided a pharmaceutical composition or combination comprising
(a) a DPP-4 inhibitor, and, optionally,
(b) a second antidiabetic agent selected from the group consisting of metformin, a sulfonylurea and pioglitazone, and, optionally,
(c) a third antidiabetic agent being different from (b) selected from the group consisting of metformin, a sulfonylurea, pioglitazone, rosiglitazone, repaglinide, nateglinide, acarbose, voglibose, miglitol, GLP-1 or GLP-1 analogue and insulin or insulin analogue,
or a pharmaceutically acceptable salt thereof.

In a further subaspect there is provided a pharmaceutical composition or combination comprising
(a) a DPP-4 inhibitor, and, optionally,
(b) a second antidiabetic agent selected from the group consisting of metformin, a sulfonylurea, pioglitazone, rosiglitazone, repaglinide, nateglinide, acarbose, voglibose, miglitol, GLP-1 or GLP-1 analogue and insulin or insulin analogue, and, optionally,
(c) a third antidiabetic agent being different from (b) selected from the group consisting of metformin, a sulfonylurea and pioglitazone,
or a pharmaceutically acceptable salt thereof.

In a yet further subaspect there is provided a pharmaceutical composition or combination comprising
(a) a DPP-4 inhibitor, and, optionally,
(b) a second antidiabetic agent selected from the group consisting of metformin and pioglitazone, and, optionally,
(c) a third antidiabetic agent being different from (b) selected from the group consisting of metformin, a sulfonylurea and pioglitazone,
or a pharmaceutically acceptable salt thereof.

In a yet further subaspect there is provided a pharmaceutical composition or combination comprising
(a) a DPP-4 inhibitor, and, optionally,
(b) a second antidiabetic agent selected from the group consisting of metformin, a sulfonylurea and pioglitazone, and, optionally,
(c) a third antidiabetic agent being different from (b) selected from the group consisting of metformin and pioglitazone,
or a pharmaceutically acceptable salt thereof.

When—besides the second antidiabetic agent—a third antidiabetic agent is chosen, said third antidiabetic agent is preferably chosen from another class than the second antidiabetic agent. Thus, it is to be understood that the second and the third antidiabetic agent are different, and preferably they are from different classes (e.g. when the second antidiabetic agent is chosen from the biguanide class, the third antidiabetic agent is preferably chosen from another class). Classes of antidiabetic agents are mentioned above, e.g. biguanide class, thiazolidindione class, sulfonylurea class, glinide class, alpha-glucosidase inhibitor class, GLP-1 analogue class, insulin class, etc.

A particular embodiment of this invention refers to monotherapy with a DPP-4 inhibitor as defined herein and/or to pharmaceutical compositions comprising a DPP-4 inhibitor as sole active ingredient.

Within combinations and/or combination therapy of this invention, a particular embodiment refers to dual combinations and/or dual therapy; another embodiment refers to triple combinations and/or triple therapy.

According to another aspect there is provided a method for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome in a patient in need thereof characterized in that a DPP-4 inhibitor and, optionally, a second and, optionally, a third antidiabetic agent as defined hereinbefore and hereinafter are administered, for example in combination, to the patient.

According to another aspect there is provided a method for preventing, slowing the progression of, delaying or treating a metabolic disorder selected from the group consisting of insulin resistance, hyperlipidemia, hypercholesterolemia, dyslipidemia, hypertension, chronic systemic inflammation, retinopathy, neuropathy, nephropathy, atherosclerosis, endothelial dysfunction, non-alcoholic fatty liver disease (NAFLD) and osteoporosis in a patient in need thereof characterized in that a DPP-4 inhibitor and, optionally, a second and, optionally, a third antidiabetic agent as defined hereinbefore and hereinafter are administered, for example in combination, to the patient.

According to another aspect there is provided a method for improving glycemic control and/or for reducing of fasting plasma glucose, of postprandial plasma glucose and/or of glycosylated hemoglobin HbA1c in a patient in need thereof characterized in that a DPP-4 inhibitor and, optionally, a second and, optionally, a third antidiabetic agent as defined hereinbefore and hereinafter are administered, for example in combination, to the patient.

The pharmaceutical composition of this invention may also have valuable disease-modifying properties with respect to diseases or conditions related to impaired glucose tolerance (IGT), impaired fasting blood glucose (IFG), insulin resistance and/or metabolic syndrome.

According to another aspect there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that a DPP-4 inhibitor and, optionally, a second and, optionally, a third antidiabetic agent as defined hereinbefore and hereinafter are administered, for example in combination, to the patient.

As by the use of a pharmaceutical composition or combination of this invention, an improvement of the glycemic control in patients in need thereof is obtainable, also those conditions and/or diseases related to or caused by an increased blood glucose level may be treated.

According to another aspect there is provided a method for preventing, slowing the progression of, delaying or treating of a condition or disorder selected from the group consisting of complications of diabetes mellitus such as cataracts and micro- and macrovascular diseases, such as nephropathy, retinopathy, neuropathy, learning and memory impairment, neurodegenerative or cognitive disorders, cardio- or cerebrovascular diseases, arteriosclerosis, hypertension, endothelial dysfunction, myocardial infarction, acute coronary syndrome, unstable angina pectoris, stable angina pectoris, cardiomyopathy, heart failure, heart rhythm disorders, vascular restenosis, peripheral arterial occlusive disease, stroke, tissue ischaemia or diabetic foot or ulcus, in a patient in need thereof characterized in that a DPP-4 inhibitor and, optionally, a second and, optionally, a third antidiabetic agent as defined hereinbefore and hereinafter are administered, for example in combination, to the patient. In particular one or more aspects of diabetic nephropathy such as hyperperfusion, proteinuria and albuminuria (including micro- or macroalbuminuria) may be treated, their progression slowed or their onset delayed or prevented. The term "tissue ischaemia" particularly comprises diabetic macroangiopathy, diabetic microangiopathy, impaired wound healing and diabetic ulcer. The terms "micro- and macrovascular diseases" and "micro- and macrovascular complications" are used interchangeably in this application.

In an embodiment, by the administration of a pharmaceutical composition or combination of this invention no gain in weight or even a reduction in body weight is the result.

According to another aspect there is provided a method for reducing body weight and/or body fat or preventing an increase in body weight and/or body fat or facilitating a reduction in body weight and/or body fat in a patient in need thereof characterized in that a DPP-4 inhibitor and, optionally, a second and, optionally, a third antidiabetic agent as defined hereinbefore and hereinafter are administered, for example in combination, to the patient.

In an embodiment, by an administration of a pharmaceutical composition or combination according to this invention a beta-cell degeneration and a decline of beta-cell functionality such as for example apoptosis or necrosis of pancreatic beta cells can be delayed or prevented. Furthermore, the functionality of pancreatic cells can be improved or restored, and the number and size of pancreatic beta cells increased. It may be shown that the differentiation status and hyperplasia of pancreatic beta-cells disturbed by hyperglycemia can be normalized by treatment with a pharmaceutical composition or combination of this invention.

According to another aspect there is provided a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof characterized in that a DPP-4 inhibitor and, optionally, a second and, optionally, a third antidiabetic agent as defined hereinbefore and hereinafter are administered, for example in combination, to the patient.

In an embodiment, by the administration of a pharmaceutical composition or combination of the present invention, an abnormal accumulation of (ectopic) fat, in particular in the liver, may be reduced or inhibited.

According to another aspect there is provided a method for preventing, slowing, delaying or treating diseases or conditions attributed to an abnormal accumulation of liver or ectopic fat in a patient in need thereof characterized in that a DPP-4 inhibitor and, optionally, a second and, optionally, a third antidiabetic agent as defined hereinbefore and hereinafter are administered, for example in combination, to the patient. Diseases or conditions which are attributed to an abnormal accumulation of liver or ectopic fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver, particularly non-alcoholic fatty liver disease (NAFLD), including hepatic steatosis, non-alcoholic steatohepatitis (NASH) and/or liver fibrosis.

According to a further aspect of the present invention, there is provided a method for preventing, slowing the progression, delaying, attenuating, treating or reversing hepatic steatosis, (hepatic) inflammation and/or an abnormal accumulation of liver fat in a patient in need thereof characterized in that a DPP-4 inhibitor and, optionally, a second and, optionally, a third antidiabetic agent as defined hereinbefore and hereinafter are administered, for example in combination, to the patient.

According to another aspect there is provided a method for maintaining and/or improving the insulin sensitivity and/or for treating or preventing hyperinsulinemia and/or insulin resistance in a patient in need thereof characterized in that a DPP-4 inhibitor and, optionally, a second and, optionally, a third antidiabetic agent as defined hereinbefore and hereinafter are administered, for example in combination, to the patient.

According to another aspect of the invention, there is provided a method for preventing, slowing progression of, delaying, or treating new onset diabetes after transplantation (NODAT) and/or post-transplant metabolic syndrome (PTMS) in a patient in need thereof characterized in that a DPP-4 inhibitor and, optionally, a second and, optionally, a third antidiabetic agent as defined hereinbefore and hereinafter are administered, for example in combination, to the patient.

According to a further aspect of the invention, there is provided a method for preventing, delaying, or reducing NODAT and/or PTMS associated complications including micro- and macrovascular diseases and events, graft rejection, infection, and death in a patient in need thereof characterized in that a DPP-4 inhibitor and, optionally, a second and, optionally, a third antidiabetic agent as defined hereinbefore and hereinafter are administered, for example in combination, to the patient.

According to another aspect of the invention, there is provided a method for treating hyperuricemia and hyperuricemia-associated conditions, such as for example gout, hypertension and renal failure, in a patient in need thereof characterized in that a DPP-4 inhibitor and, optionally, a second and, optionally, a third antidiabetic agent as defined hereinbefore and hereinafter are administered, for example in combination, to the patient.

According to another aspect there is provided the use of a DPP-4 inhibitor for the manufacture of a medicament for use in a method of preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing body weight and/or body fat or preventing an increase in body weight and/or body fat or facilitating a reduction in body weight and/or body fat; or preventing, slowing, delaying or treating the degeneration of pancreatic beta cells and/or the decline of the functionality of pancreatic beta cells and/or for improving and/or restoring or protecting the functionality of pancreatic beta cells and/or restoring the functionality of pancreatic insulin secretion; or preventing, slowing, delaying or treating diseases or conditions attributed to an abnormal accumulation of liver or ectopic fat; or maintaining and/or improving the insulin sensitivity and/or for treating or preventing hyperinsulinemia and/or insulin resistance; or preventing, slowing progression of, delaying, or treating new onset diabetes after transplantation (NODAT) and/or post-transplant metabolic syndrome (PTMS); or preventing, delaying, or reducing NODAT and/or PTMS associated complications including micro- and macrovascular diseases and events, graft rejection, infection, and death; or treating hyperuricemia and hyperuricemia associated conditions;

in a patient in need thereof, comprising administering the DPP-4 inhibitor alone or, optionally, in combination with a second and, optionally, with a third antidiabetic agent as defined hereinbefore and hereinafter to the patient.

According to another aspect there is provided the use of a second antidiabetic agent as defined hereinbefore and hereinafter for the manufacture of a medicament for use in a method of preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing body weight and/or body fat or preventing an increase in body weight and/or body fat or facilitating a reduction in body weight and/or body fat; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver or ectopic fat; or maintaining and/or improving the insulin sensitivity and/or for treating or preventing hyperinsulinemia and/or insulin resistance;

in a patient in need thereof, comprising administering the second antidiabetic agent in combination with a DPP-4 inhibitor and, optionally, with a third antidiabetic agent as defined hereinbefore and hereinafter to the patient.

According to another aspect there is provided the use of a pharmaceutical composition according to the present invention for the manufacture of a medicament for a therapeutic and preventive method as described hereinbefore and hereinafter.

Patients of a TCF7L2 risk genotype (also referred to herein as TCF7L2 risk genotype patients) within the meaning of this invention refer to those patients who have one or more single nucleotide polymorphisms (SNPs) in the gene coding for TCF7L2, especially a SNP selected from rs7903146, rs12255372 and rs10885406, especially rs7903146; in more particular, those patients who carry at least one T allele of SNP rs7903146 of TCF7L2, i.e. the CT genotype or TT genotype; especially those who carry two T alleles of SNP rs7903146 of TCF7L2, i.e. the TT genotype, are at high-risk and are expected to be difficult to treat (e.g. to achieve adequate glycemic control).

The present invention provides a DPP-4 inhibitor (preferably linagliptin), pharmaceutical composition, combination or medicament according to the present invention for use in a therapeutic and/or preventive method as described hereinbefore and hereinafter (e.g. treating type 2 diabetes) in one or more of the following patient groups:

TCF7L2 high risk genotype patients carrying two T alleles of SNP rs7903146 of TCF7L2, i.e. TT genotype (where clinically meaningful response e.g. in glycemic control is provided), TCF7L2 risk genotype patients carrying one T allele of SNP rs7903146 of TCF7L2, i.e. CT genotype (where clinically favorable response e.g. in glycemic control is provided), TCF7L2 wild genotype patients carrying two CC alleles of SNP rs7903146 of TCF7L2, i.e. CC genotype (where clinically more favorable response e.g. in glycemic control is provided).

Within a particular aspect of the invention, the invention relates to a DPP-4 inhibitor, a pharmaceutical composition or combination of the present invention for a therapeutic and/or preventive method or use as described hereinbefore and hereinafter (e.g. treating type 2 diabetes), said method or use comprising (i) identifying a patient being susceptible to said therapeutic and/or preventive method or use comprising testing whether the patient is of any TCF7L2 risk genotype, particularly whether the patient has one or more single nucleotide polymorphisms (SNPs) in the gene coding for TCF7L2, especially a SNP selected from rs7903146, rs12255372 and rs10885406, for example whether the patient carries at least one T allele of SNP rs7903146 of TCF7L2, e.g. whether the patient is of CT genotype (i.e. whether the patient carries one T allele of SNP rs7903146 of TCF7L2) or, particularly, whether the patient is of TT genotype (i.e. whether the patient carries two T alleles of SNP rs7903146 of TCF7L2), or testing whether the patient is of TCF7L2 wild genotype, particularly whether the patient carries two C alleles of SNP rs7903146 of TCF7L2 (i.e. whether the patient is of CC wild genotype), and (ii) administering an effective amount of the DPP-4 inhibitor, pharmaceutical composition or combination to the patient identified in step (i).

Within another particular aspect of the invention, the invention relates to a DPP-4 inhibitor, a pharmaceutical composition, combination or medicament of the present invention for a therapeutic and/or preventive method or use as described hereinbefore and hereinafter (e.g. treating type 2 diabetes) in TCF7L2 risk genotype patients, e.g. in those patients who have one or more single nucleotide polymorphisms (SNPs) in the gene coding for TCF7L2, especially a SNP selected from rs7903146, rs12255372 and rs10885406, especially rs7903146; in more particular, in those patients who carry at least one T allele of SNP rs7903146 of TCF7L2, i.e. the CT genotype or TT genotype.

Within another particular aspect of the invention, the invention relates to a DPP-4 inhibitor, a pharmaceutical composition, combination or medicament of the present invention for a therapeutic and/or preventive method or use as described hereinbefore and hereinafter (e.g. treating type 2 diabetes) in TCF7L2 wild genotype patients, e.g. in those patients who carry two C alleles of SNP rs7903146 of TCF7L2, i.e. the CC genotype.

In this context, a particular sub-population of the patients described hereinbefore and hereinafter (e.g. of the patients in need of a therapeutic or preventive method as described herein), refers to those patients who have one or more single nucleotide polymorphisms (SNPs) in the gene coding for TCF7L2, especially at least one SNP selected from rs7903146, rs12255372 and rs10885406, especially rs7903146, in more particular, those patients who carry at least one T allele of SNP rs7903146 of TCF7L2, i.e. the CT genotype or TT genotype.

In more particular, those patients who carry at least one T allele of SNP rs7903146 of TCF7L2, i.e. the CT genotype or TT genotype, especially who carry two T alleles of SNP rs7903146 of TCF7L2, i.e. the TT genotype, are strongly susceptible to increased TCF7L2 expression in pancreatic beta cells, impaired insulin secretion, incretine effects, enhanced rate of hepatic glucose production and/or diabetes. The T allele of rs7903146 TCF7L2 is associated with impaired insulinotropic action of incretin hormones, reduced 24 h profiles of plasma insulin and glucagon, and increased hepatic glucose production.

Another particular sub-population of the patients described hereinbefore and hereinafter (e.g. of the patients in need of a therapeutic or preventive method as described herein), refers to those patients who are of TCF7L2 wild genotype, particularly those who are of the TCF7L2 rs7903146 CC wild genotype.

According to one embodiment of this aspect of the invention, there is provided a DPP-4 inhibitor, a pharmaceutical composition, combination or medicament according to the present invention for a therapeutic and/or preventive method or use as described hereinbefore and hereinafter (particularly for treating and/or preventing type 2 diabetes and/or obesity), in patients with reduced (glucose-stimulated) insulin secretion, increased hepatic gluconeogenesis and/or reduced insulinotropic effect or action of incretin hormones (e.g. GLP-1 and/or GIP), e.g. impaired incretin sensitivity, associated with a TCF7L2 risk genotype, particularly with such a TCF7L2 risk genotype as mentioned above.

According to another embodiment of this aspect of the invention, there is provided a method of determining patient's treatment response to a DPP-4 inhibitor, a pharmaceutical composition, combination or medicament according to the present invention, said method comprising the step of determining whether the patient is of TCF7L2 risk genotype as described herein, e.g. testing whether the patient belongs to the particular subpopulation of TCF7L2 risk genotype carriers, or determining whether the patient is of TCF7L2 wild genotype, e.g. testing whether the patient carries the wild-type CC allele at rs7903146 in TCF7L2.

According to another embodiment of this aspect of the invention, there is provided a DPP-4 inhibitor, a pharmaceutical composition, combination or medicament according to the present invention for use in a therapeutic and/or preventive method as described hereinbefore and hereinafter (particularly for treating and/or preventing type 2 diabetes and/or obesity) in a patient in need thereof, said method comprising testing whether the patient is of any TCF7L2 risk genotype as described herein.

According to another embodiment of this aspect of the invention, there is provided a DPP-4 inhibitor, a pharmaceutical composition, combination or medicament according to the present invention for use in a therapeutic and/or preventive method as described hereinbefore and hereinafter (particularly for treating and/or preventing type 2 diabetes and/or obesity) in a patient in need thereof, said method comprising testing whether the patient is of TCF7L2 wild genotype as described herein.

According to another aspect of the invention, the testing for TCF7L2 risk genotypes may be used for patient stratification, e.g. to enrich patient population in clinical trials to test the efficacy of the DPP-4 inhibitor.

According to another aspect of the invention, the method of determining the treatment susceptibility of an individual (e.g. comprising the testing for TCF7L2 risk or wild genotypes as described herein) may be used for determination whether the patient may respond to a lower level or may require a higher level of administered DPP-4 inhibitor, optionally in combination with one or more other active substances.

According to another aspect of the invention, determining the treatment susceptibility of an individual comprising the testing for TCF7L2 risk or wild genotypes as described herein may be used for determination whether the patient may be treated in monotherapy or in combination therapy with one or more additional antidiabetics according to this invention, e.g. to provide adequate glycemic control. For example, those patients with decreased likelihood of favorable response may require combination treatment, e.g. to achieve adequate glycemic control.

DEFINITIONS

Figure 1:
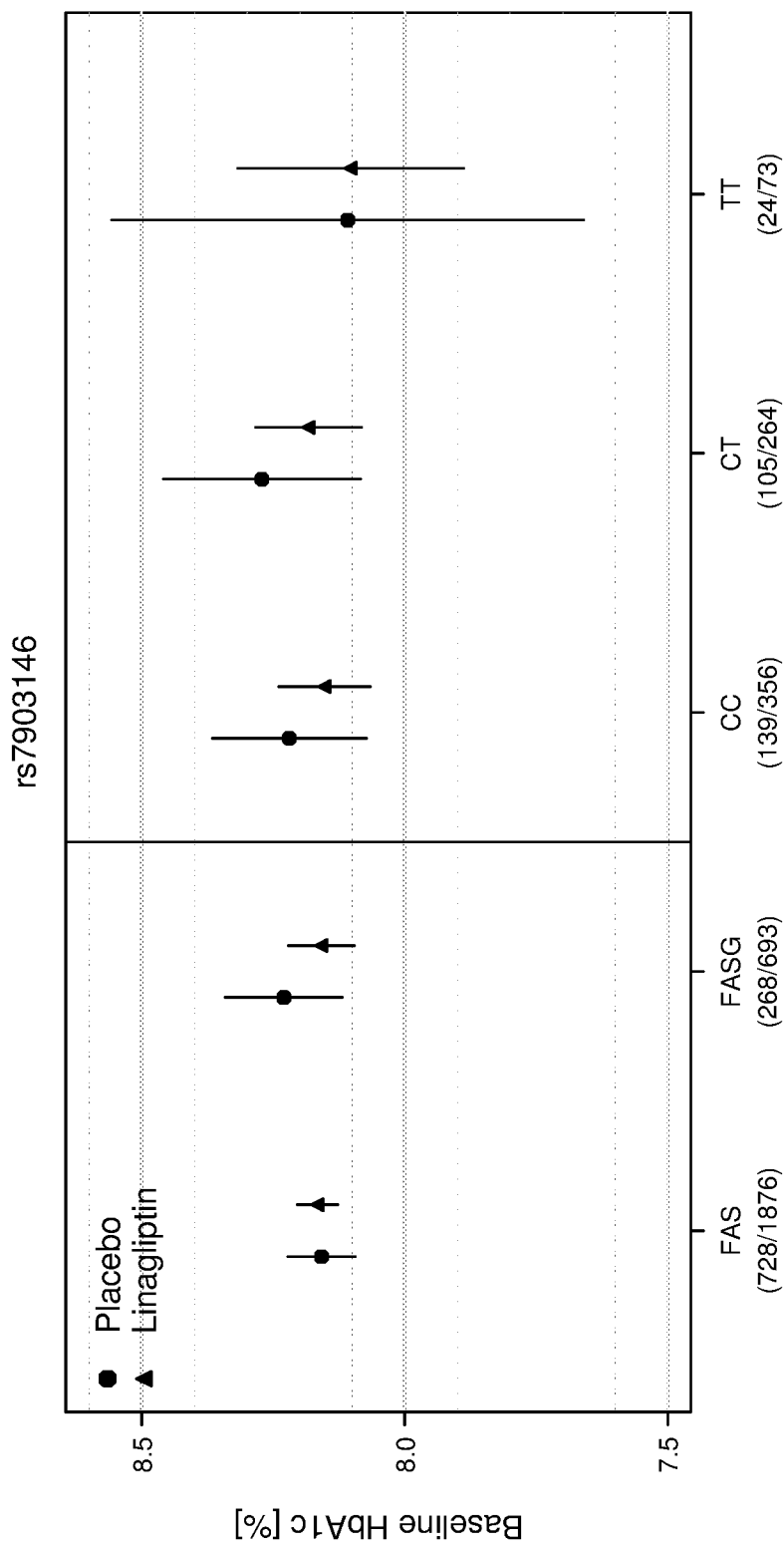
FIG. 1 shows the baseline HbA1c values for the whole patient population of the studies (full analysis set, FAS), for the subpopulation for which genetic analyses are performed (full analysis set for pharmacogenetic analyses, FASG), as well as for the subgroups defined by SNP rs7903146 in TCF7L2 genotypes (CC, CT, TT) of this subpopulation.

The term "active ingredient" of a pharmaceutical composition or combination of the present invention means the DPP-4 inhibitor and/or, if present, the second antidiabetic agent and/or, if present, the third antidiabetic agent of the present invention.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference 85 cm in men and 90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 110 mg/dL (6.11 mmol/L) or 100 mg mg/dL (5.6 mmol/L). The word "fasting" has the usual meaning as a medical term.

The term "hyperglycemia" is defined as the condition in which a subject has a fasting blood glucose concentration above the normal range, greater than 110 mg/dL (6.11 mmol/L) or 100 mg mg/dL (5.6 mmol/L). The word "fasting" has the usual meaning as a medical term.

The term "hypoglycemia" is defined as the condition in which a subject has a blood glucose concentration below the normal range of 60 to 115 mg/dL (3.3 to 6.3 mmol/L), in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28: 412-19), of the ratio of intact proinsulin to insulin (Forst et al., *Diabetes* 2003, 52 (Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR}=[\text{fasting serum insulin }(\mu U/mL)]\times[\text{fasting plasma glucose(mmol/L)/22.5}]$$

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28: 412-19), the ratio of intact proinsulin to insulin (Forst et al., *Diabetes* 2003, 52 (Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes type 2 diabetes patients with a secondary antidiabetic drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference 85 cm in men and 90 cm in women;
2. Triglycerides: ≥150 mg/dL
3. HDL-cholesterol <40 mg/dL in men
4. Blood pressure ≥130/85 mm Hg (SBP ≥130 or DBP ≥85)
5. Fasting blood glucose ≥110 mg/dL or ≥100 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The definitions of NODAT (new onset diabetes after transplantation) and PTMS (post-transplant metabolic syndrome) follow closely that of the American Diabetes Association diagnostic criteria for type 2 diabetes, and that of the International Diabetes Federation (IDF) and the American Heart Association/National Heart, Lung, and Blood Institute, for the metabolic syndrome. NODAT and/or PTMS are associated with an increased risk of micro- and macrovascular disease and events, graft rejection, infection, and death. A number of predictors have been identified as potential risk factors related to NODAT and/or PTMS including a higher age at transplant, male gender, the pre-transplant body mass index, pre-transplant diabetes, and immunosuppression.

The term "hyperuricemia" denotes a condition of high serum total urate levels. In human blood, uric acid concentrations between 3.6 mg/dL (ca. 214 μmol/L) and 8.3 mg/dL (ca. 494 μmol/L) are considered normal by the American Medical Association. High serum total urate levels, or hyperuricemia, are often associated with several maladies. For example, high serum total urate levels can lead to a type of arthritis in the joints known as gout. Gout is a condition created by a build up of monosodium urate or uric acid crystals on the articular cartilage of joints, tendons and surrounding tissues due to elevated concentrations of total urate levels in the blood stream. The build up of urate or uric acid on these tissues provokes an inflammatory reaction of these tissues. Saturation levels of uric acid in urine may result in kidney stone formation when the uric acid or urate crystallizes in the kidney. Additionally, high serum total urate levels are often associated with the so-called metabolic syndrome, including cardiovascular disease and hypertension.

The term "DPP-4 inhibitor" in the scope of the present invention relates to a compound that exhibits inhibitory activity on the enzyme dipeptidyl peptidase IV (DPP-4). Such inhibitory activity can be characterised by the IC50 value. A DPP-4 inhibitor preferably exhibits an IC50 value below 10000 nM, preferably below 1000 nM. Certain DPP-4 inhibitors exhibit an IC50 value below 100 nM, or even ≤50 nM. IC50 values of DPP-4 inhibitors are usually above 0.01 nM, or even above 0.1 nM. DPP-IV inhibitors may include biologic and non-biologic, in particular non-peptidic compounds. The inhibitory effect on DPP-4 can be determined by methods known in the literature, in particular as described in the application WO 02/068420 or WO 2004/018468 (page 34), which are incorporated herein by reference in its entirety. The term "DPP-4 inhibitor" also comprises any pharmaceutically acceptable salts thereof, hydrates and solvates thereof, including the respective crystalline forms.

The terms "treatment" and "treating" or analogous terms comprise particularly therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventive treating" and "preventing" or ananlogous terms are used interchangeably and comprise a treatment of patients at risk to develop a condition mentioned hereinbefore, thus reducing said risk.

DETAILED DESCRIPTION

The aspects of the present invention, in particular the pharmaceutical compounds, compositions, combinations, methods and uses, refer to DPP-4 inhibitors, second and/or third antidiabetic agents as defined hereinbefore and hereinafter.

In a first embodiment (embodiment A), a DPP-4 inhibitor in the context of the present invention is any DPP-4 inhibitor of formula (I)

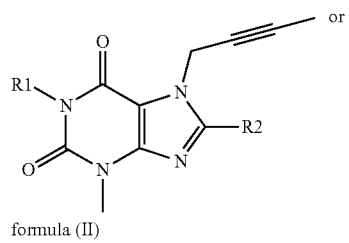

formula (II)

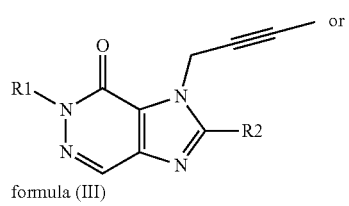

formula (III)

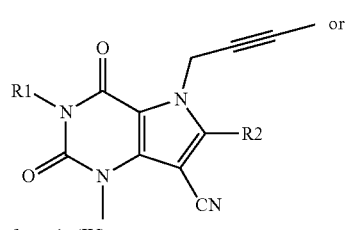

formula (IV)

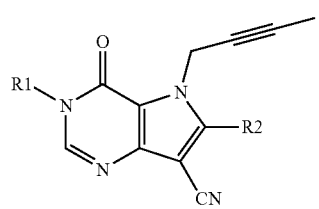

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino,
or its pharmaceutically acceptable salt.

In a second embodiment (embodiment B), a DPP-4 inhibitor in the context of the present invention is a DPP-4 inhibitor selected from the group consisting of sitagliptin, vildagliptin, saxagliptin, alogliptin, gemigliptin,
(2S)-1-{[2-(5-Methyl-2-phenyl-oxazol-4-yl)-ethylamino]-acetyl}-pyrrolidine-2-carbonitrile,
(2S)-1-{[1,1,-Dimethyl-3-(4-pyridin-3-yl-imidazol-1-yl)-propylamino]-acetyl}-pyrrolidine-2-carbonitrile,
(S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one,
(3,3-Difluoropyrrolidin-1-yl)-((2S,4S)-4-(4-(pyrimidin-2-yl)piperazin-1-yl)pyrrolidin-2-yl)methanone,
(1((3S,4S)-4-amino-1-(4-(3,3-difluoropyrrolidin-1-yl)-1,3,5-triazin-2-yl)pyrrolidin-3-yl)-5,5-difluoropiperidin-2-one, (2S,4S)-1-{2-[(3S,1R)-3-(1H-1,2,4-Triazol-1-ylmethyl)cyclopentylamino]-acetyl}-4-fluoropyrrolidine-2-carbonitrile, (R)-2-[6-(3-Amino-piperidin-1-yl)-3-methyl-2,4-dioxo-3,4-dihydro-2H-pyrimidin-1-ylmethyl]-4-fluoro-benzonitrile, 5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide, 3-{(2S,4S)-4-[4-(3-Methyl-1-phenyl-1H-pyrazol-5-yl)piperazin-1-yl]pyrrolidin-2-ylcarbonyl}thiazolidine,

[(2R)-1-{[(3R)-pyrrolidin-3-ylamino]acetyl}pyrrolidin-2-yl]boronic acid, (2S,4S)-1-[2-[(4-ethoxycarbonylbicyclo[2.2.2]oct-1-yl)amino]acetyl]-4-fluoropyrrolidine-2-carbonitrile, 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile, 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione, and (S)-2-methylpyrazolo[1,5-a]primidine-6-carboxylic acid {2-[(2-cyanopyrrolidin-1-yl)-2-oxoethylamino]-2-methylpropyl}amide, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142):

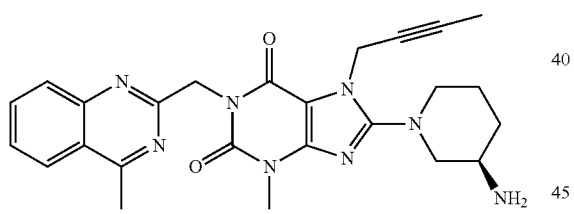

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252):

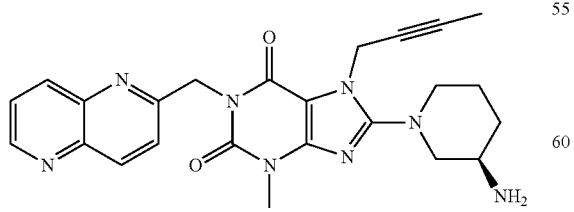

1-[(Quinazolin-2-yl)methyl]-3-methyl-7-(2-butyn-1-yl)-8-((R)-3-amino-piperidin-1-yl)-xanthine (Compare WO 2004/018468, Example 2(80):

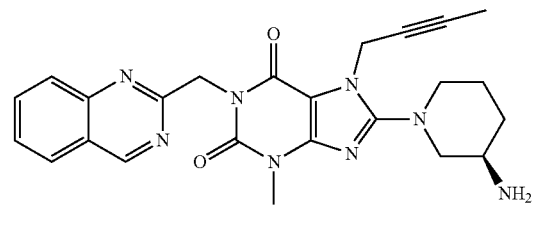 [SMILES: CC#CCn1c(N2CCC[C@@H](N)C2)nc2c1c(=O)n(Cc1ncc3ccccc3n1)c(=O)n2C]

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136):

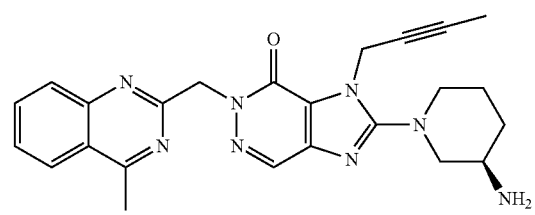 [SMILES: CC#CCn1c(N2CCC[C@@H](N)C2)nc2cnn(Cc3nc(C)c4ccccc4n3)c(=O)c21]

1-[(4-Methyl-quinazolin-2-yl)methyl]-3-methyl-7-(2-butyin-1-yl)-8-[(2-amino-2-methyl-propyl)-methylamino]-xanthine (compare WO 2006/029769, example 2(1):

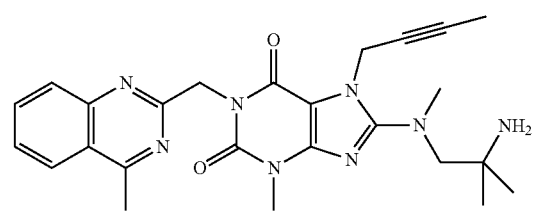 [SMILES: CC#CCn1c(N(C)CC(C)(C)N)nc2c1c(=O)n(Cc1nc(C)c3ccccc3n1)c(=O)n2C]

1-[(3-Cyano-quinolin-2-yl)methyl]-3-methyl-7-(2-butyn-1-yl)-8-((R)-3-amino-piperidin-1-yl)-xanthine (compare WO 2005/085246, example 1(30):

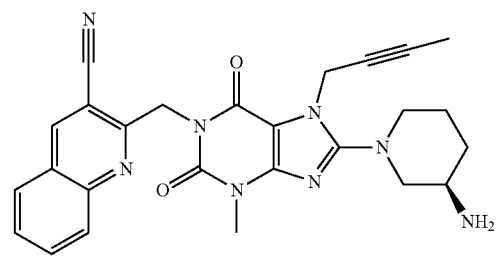 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39):

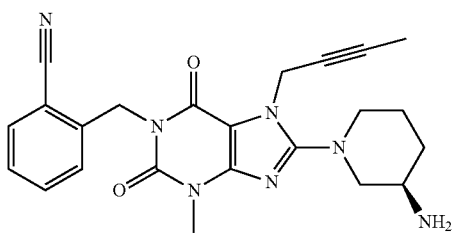 [SMILES: CC#CCn1c(N2CCC[C@@H](N)C2)nc2c1c(=O)n(Cc1ccccc1C#N)c(=O)n2C]

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4):

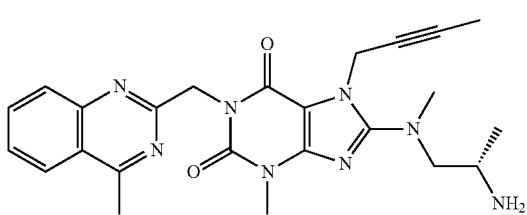 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52):

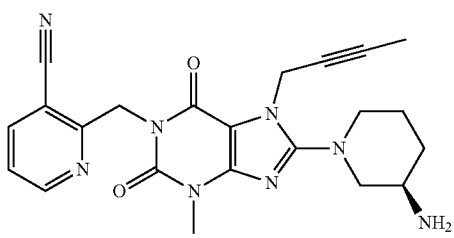 [SMILES: CC#CCn1c(N2CCC[C@@H](N)C2)nc2c1c(=O)n(Cc1ncccc1C#N)c(=O)n2C]

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81):

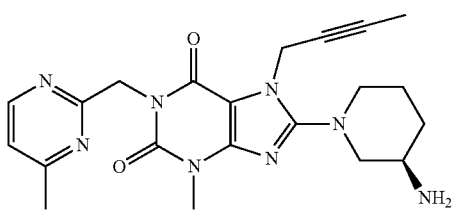 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82):

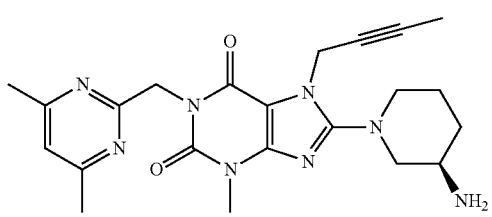 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(83):

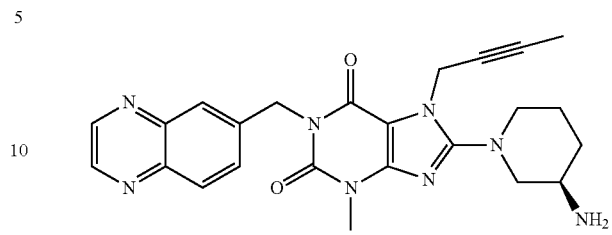

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as linagliptin or BI 1356).

As further DPP-4 inhibitors the following compounds can be mentioned:

Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, (A)

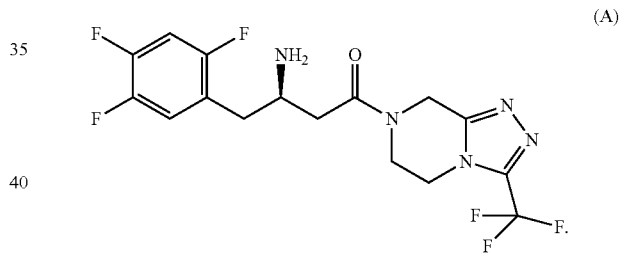

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485.

For details, e.g. on a process to manufacture, to formulate or to use this compound or a salt thereof, reference is thus made to these documents.

A tablet formulation for sitagliptin is commercially available under the trade name Januvia®. A tablet formulation for sitagliptin/metformin combination is commercially available under the trade name Janumet®.

Vildagliptin (LAF-237) having the structural formula B below is (2S)-{[(3-hydroxyadamantan-1-yl)amino]acetyl}pyrrolidine-2-carbonitrile, also named (S)-1-[(3-hydroxy-1-adamantyl)amino]acetyl-2-cyano-pyrrolidine, (B)

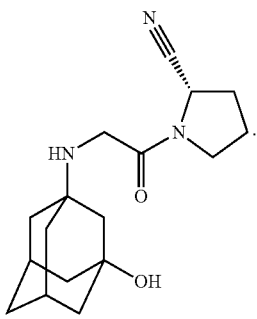

(E)

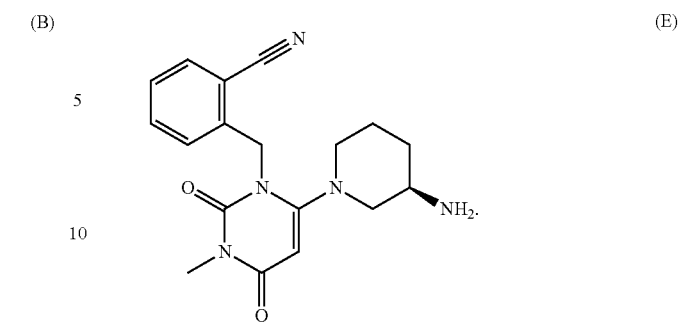

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723.

For details, e.g. on a process to manufacture, to formulate or to use this compound or a salt thereof, reference is thus made to these documents.

A tablet formulation for vildagliptin is commercially available under the trade name Galvus®. A tablet formulation for vildagliptin/metformin combination is commercially available under the trade name Eucreas®.

Saxagliptin (BMS-477118) having the structural formula C below is (1S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile, (C)

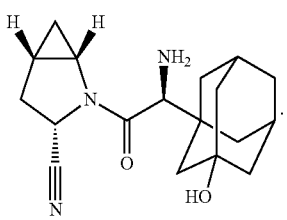

Saxagliptin is specifically disclosed in U.S. Pat. No. 6,395,767 and in Example 60 of WO 01/68603.

In one embodiment, saxagliptin is in the form of its HCl salt or its mono-benzoate salt as disclosed in WO 2004/052850. In a further embodiment, saxagliptin is in the form of the free base. In a yet further embodiment, saxagliptin is in the form of the monohydrate of the free base as disclosed in WO 2004/052850. Crystalline forms of the HCl salt and of the free base of saxagliptin are disclosed in WO 2008/131149. A process for preparing saxagliptin is also disclosed in WO 2005/106011 and WO 2005/115982. Saxagliptin can be formulated in a tablet as described in WO 2005/117841.

For details, e.g. on a process to manufacture, to formulate or to use this compound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl)benzonitrile Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629. Alogliptin (namely its benzoate salt) can be formulated in a tablet and administered as described in WO 2007/033266. A solid preparation of alogliptin/pioglitazone and its preparation and use is described in WO 2008/093882. A solid preparation of alogliptin/metformin and its preparation and use is described in WO 2009/011451. For details, e.g. on a process to manufacture, to formulate or to use this compound or a salt thereof, reference is thus made to these documents.

(2S)-1-{[2-(5-Methyl-2-phenyl-oxazol-4-yl)-ethylamino]-acetyl}-pyrrolidine-2-carbonitrile or a pharmaceutically acceptable salt thereof, preferably the mesylate, or (2S)-1-{[1,1,-Dimethyl-3-(4-pyridin-3-yl-imidazol-1-yl)-propylamino]-acetyl}-pyrrolidine-2-carbonitrile or a pharmaceutically acceptable salt thereof:

These compounds and methods for their preparation are disclosed in WO 03/037327. The mesylate salt of the former compound as well as crystalline polymorphs thereof are disclosed in WO 2006/100181. The fumarate salt of the latter compound as well as crystalline polymorphs thereof are disclosed in WO 2007/071576. These compounds can be formulated in a pharmaceutical composition as described in WO 2007/017423.

For details, e.g. on a process to manufacture, to formulate or to use these compounds or salts thereof, reference is thus made to these documents.

(S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one (also named carmegliptin) or a pharmaceutically acceptable salt thereof:

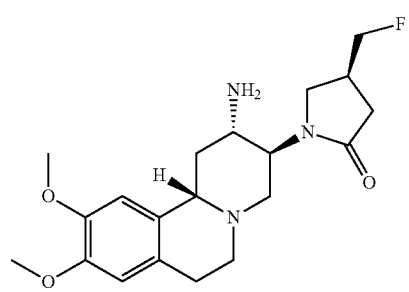 [SMILES: COc1cc2c(cc1OC)[C@@H]1C[C@H](N)[C@@H](N3C[C@@H](CF)CC3=O)CN1CC2]

This compound and methods for its preparation are disclosed in WO 2005/000848. A process for preparing this compound (specifically its dihydrochloride salt) is also disclosed in WO 2008/031749, WO 2008/031750 and WO 2008/055814. This compound can be formulated in a pharmaceutical composition as described in WO 2007/017423.

For details, e.g. on a process to manufacture, to formulate or to use this compound or a salt thereof, reference is thus made to these documents.

(3,3-Difluoropyrrolidin-1-yl)-((2S,4S)-4-(4-(pyrimidin-2-yl)piperazin-1-yl)pyrrolidin-2-yl)methanone (also named gosogliptin) or a pharmaceutically acceptable salt thereof:

This compound and methods for its preparation are disclosed in WO 2005/116014 and U.S. Pat. No. 7,291,618.

For details, e.g. on a process to manufacture, to formulate or to use this compound or a salt thereof, reference is thus made to these documents.

(1((3S,4S)-4-amino-1-(4-(3,3-difluoropyrrolidin-1-yl)-1,3,5-triazin-2-yl)pyrrolidin-3-yl)-5,5-difluoropiperidin-2-one or a pharmaceutically acceptable salt thereof:

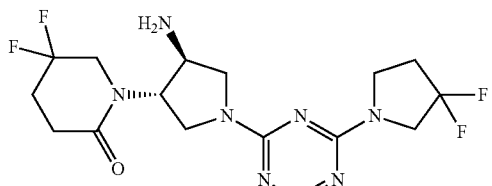

This compound and methods for its preparation are disclosed in WO 2007/148185 and US 20070299076. For details, e.g. on a process to manufacture, to formulate or to use this compound or a salt thereof, reference is thus made to these documents.

(2S,4S)-1-{2-[(3S,1R)-3-(1H-1,2,4-Triazol-1-ylmethyl)cyclopentylamino]-acetyl}-4-fluoropyrrolidine-2-carbonitrile (also named melogliptin) or a pharmaceutically acceptable salt thereof:

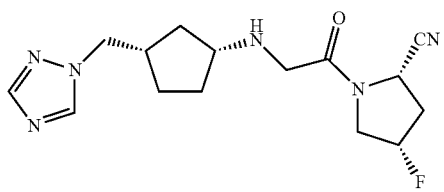 [SMILES: N#C[C@@H]1C[C@H](F)CN1C(=O)CN[C@@H]1CC[C@H](Cn2cncn2)C1]

This compound and methods for its preparation are disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-benzonitrile or a pharmaceutically acceptable salt thereof:

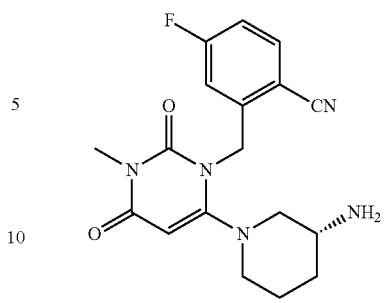

This compound and methods for its preparation and use are disclosed in WO 2005/095381, US 2007060530, WO 2007/033350, WO 2007/035629, WO 2007/074884, WO 2007/112368, WO 2008/033851, WO 2008/114800 and WO 2008/114807. Specifically claimed salts include the succinate (WO 2008/067465), benzoate, benzenesulfonate, p-toluenesulfonate, (R)-mandelate and hydrochloride. For details, e.g. on a process to manufacture, to formulate or to use this compound or a salt thereof, reference is thus made to these documents.

5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide or a pharmaceutically acceptable salt thereof:

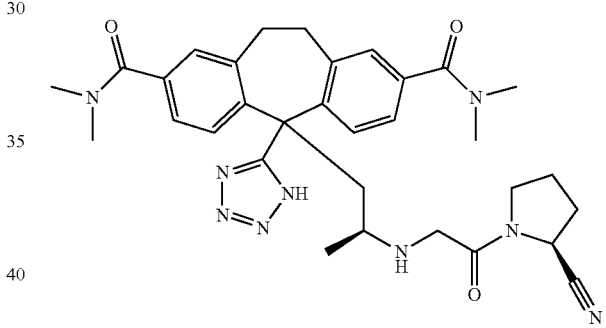

This compound and methods for its preparation are disclosed in WO 2006/116157 and US 2006/270701. For details, e.g. on a process to manufacture, to formulate or to use this compound or a salt thereof, reference is thus made to these documents.

3-{(2S,4S)-4-[4-(3-Methyl-1-phenyl-1H-pyrazol-5-yl)piperazin-1-yl]pyrrolidin-2-ylcarbonyl}thiazolidine (also named teneligliptin) or a pharmaceutically acceptable salt thereof:

This compound and methods for its preparation are disclosed in WO 02/14271. Specific salts are disclosed in WO 2006/088129 and WO 2006/118127 (including hydrochloride, hydrobromide, inter alia). Combination therapy using this compound is described in WO 2006/129785. For details, e.g. on a process to manufacture, to formulate or to use this compound or a salt thereof, reference is thus made to these documents.

[(2R)-1-{[(3R)-pyrrolidin-3-ylamino]acetyl}pyrrolidin-2-yl]boronic acid (also named dutogliptin) or a pharmaceutically acceptable salt thereof:

This compound and methods for its preparation are disclosed in WO 2005/047297, WO 2008/109681 and WO 2009/009751. Specific salts are disclosed in WO 2008/027273 (including citrate, tartrate). A formulation of this compound is described in WO 2008/144730. A formulation of dutogliptin (as its tartrate salt) with metformin is described in WO 2009/091663. For details, e.g. on a process to manufacture, to formulate or to use this compound or a salt thereof, reference is thus made to these documents.

(2S,4S)-1-[2-[(4-ethoxycarbonylbicyclo[2.2.2]oct-1-yl) amino]acetyl]-4-fluoropyrrolidine-2-carbonitrile or a pharmaceutically acceptable salt thereof:

This compound and methods for its preparation are disclosed in WO 2005/075421, US 2008/146818 and WO 2008/114857. For details, e.g. on a process to manufacture, to formulate or to use this compound or a salt thereof, reference is thus made to these documents.

2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile or a pharmaceutically acceptable salt thereof, or 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione or a pharmaceutically acceptable salt thereof:

These compounds and methods for their preparation are disclosed in WO 2009/084497 and WO 2006/068163, respectively. Combination therapy using the latter of these two compounds is described in WO 2009/128360. For details, e.g. on a process to manufacture, to formulate or to use these compounds or salts thereof, reference is thus made to these documents.

(S)-2-methylpyrazolo[1,5-a]primidine-6-carboxylic acid {2-[(2-cyanopyrrolidin-1-yl)-2-oxoethylamino]-2-methylpropyl}amide (also named anagliptin) or a pharmaceutically acceptable salt:

This compound and methods for its preparation are disclosed in WO 2004/067509. Combination therapy using this compound is described in WO 2009/139362. For details, e.g. on a process to manufacture, to formulate or to use this compound or a salt thereof, reference is thus made to these documents.

Preferably the DPP-4 inhibitor is selected from the group G2 consisting of linagliptin, sitagliptin, vildagliptin, alogliptin, saxagliptin, carmegliptin, gosogliptin, teneligliptin, melogliptin and dutogliptin, or a pharmaceutically acceptable salt of one of the hereinmentioned DPP-4 inhibitors, or a prodrug thereof.

More preferably the DPP-4 inhibitor is selected from the group G2 consisting of linagliptin, sitagliptin, vildagliptin, alogliptin, saxagliptin, teneligliptin and dutogliptin, or a pharmaceutically acceptable salt of one of the hereinmentioned DPP-4 inhibitors, or a prodrug thereof.

A particularly preferred DPP-4 inhibitor within the present invention is linagliptin. The term "linagliptin" as employed herein refers to linagliptin and pharmaceutically acceptable salts thereof, including hydrates and solvates thereof, and crystalline forms thereof. Crystalline forms are described in WO 2007/128721. Methods for the manufacture of linagliptin are described in the patent applications WO 2004/018468 and WO 2006/048427 for example. Linagliptin is distinguished from structurally comparable DPP-4 inhibitors, as it combines exceptional potency and a long-lasting effect with favourable pharmacological properties, receptor selectivity and a favourable side-effect profile or bring about unexpected therapeutic advantages or improvements in monotherapy and/or when used in combination with a second and, optionally, a third antidiabetic agent according to this invention.

For avoidance of any doubt, the disclosure of each of the foregoing documents cited above in connection with the specified DPP-4 inhibitors is specifically incorporated herein by reference in its entirety.

In one aspect of the present invention, the pharmaceutical compositions, methods and uses according to this invention relate to those compositions which comprise the DPP-4 inhibitor as sole active ingredient (i.e. the second and third antidiabetic agent are both absent) and/or, respectively, to monotherapy using the DPP-4 inhibitor alone.

In another aspect of the present invention, the pharmaceutical compositions, combinations, methods and uses according to this invention relate to those compositions or combinations which comprise the DPP-4 inhibitor and the second antidiabetic agent as sole active ingredients (i.e. the third antidiabetic agent is absent) and/or, respectively, to dual combination therapy using the DPP-4 inhibitor and the second antidiabetic agent.

In another aspect of the present invention, the pharmaceutical compositions, combinations, methods and uses according to this invention relate to those compositions or combinations which comprise the DPP-4 inhibitor, the second and the third antidiabetic agent and/or, respectively, to triple combination therapy using the DPP-4 inhibitor, the second and the third antidiabetic agent.

Further, a DPP-4 inhibitor according to this invention may be further characterized in that said DPP-4 inhibitor does not significantly impair glomerular and/or tubular function of a type 2 diabetes patient with chronic renal insufficiency (e.g. mild, moderate or severe renal impairment or end stage renal disease), and/or said DPP-4 inhibitor does not require to be dose-adjusted in a type 2 diabetes patient with impaired renal function (e.g. mild, moderate or severe renal impairment or end stage renal disease).

The second antidiabetic agent and, if present, the third antidiabetic agent is selected from the group G3 consisting of biguanides, thiazolidindiones, sulfonylureas, glinides, inhibitors of alpha-glucosidase, GLP-1 or GLP-1 analogues, and insulin or insulin analogues, or a pharmaceutically acceptable salt thereof. In the following preferred embodiments regarding the second and/or the third antidiabetic agent are described.

The group G3 comprises biguanides. Examples of biguanides are metformin, phenformin and buformin. A preferred biguanide is metformin. A DPP-4 inhibitor in combination with a biguanide, in particular metformin, can provide more efficacious glycemic control and/or may act together with the biguanide, for example to reduce weight, that has e.g. overall beneficial effects on the metabolic syndrome which is commonly associated with type 2 diabetes mellitus.

The term "metformin" as employed herein refers to metformin or a pharmaceutically acceptable salt thereof such as the hydrochloride salt, the metformin (2:1) fumarate salt, and the metformin (2:1) succinate salt, the hydrobromide salt, the p-chlorophenoxy acetate or the embonate, and other known metformin salts of mono and dibasic carboxylic acids. It is preferred that the metformin employed herein is the metformin hydrochloride salt.

The group G3 comprises thiazolidindiones. Examples of thiazolidindiones (TZD) are pioglitazone and rosiglitazone. TZD therapy is associated with weight gain and fat redistribution. In addition, TZD cause fluid retention and are not indicated in patients with congestive heart failure. Long term treatment with TZD are further associated with an increased risk of bone fractures. A DPP-4 inhibitor in combination with a thiazolidindione, in particular pioglitazone, can provide more efficacious glycemic control and/or can minimize side effects of the treatment with TZD.

The term "pioglitazone" as employed herein refers to pioglitazone, including its enantiomers, mixtures thereof and its racemate, or a pharmaceutically acceptable salt thereof such as the hydrochloride salt.

The term "rosiglitazone" as employed herein refers to rosiglitazone, including its enantiomers, mixtures thereof and its racemate, or a pharmaceutically acceptable salt thereof such as the maleate salt.

The group G3 comprises sulfonylureas. Examples of sulfonylureas are glibenclamide, tolbutamide, glimepiride, glipizide, gliquidone, glibornuride, glyburide, glisoxepide and gliclazide. Preferred sulfonylureas are tolbutamide, gliquidone, glibenclamide and glimepiride, in particular glibenclamide and glimepiride. As the efficacy of sulfonylureas wears off over the course of treatment, a combination of a DPP-4 inhibitor with a sulfonylurea may offer additional benefit to the patient in terms of better glycemic control. Also, treatment with sulfonylureas is normally associated with gradual weight gain over the course of treatment and a DPP-4 inhibitor may minimize this side effect of the treatment with an sulfonylurea and/or improve the metabolic syndrome. Also, a DPP-4 inhibitor in combination with a sulfonylurea may minimize hypoglycemia which is another undesirable side effect of sulfonylureas. This combination may also allow a reduction in the dose of sulfonylureas, which may also translate into less hypoglycemia.

Each term of the group "glibenclamide", "glimepiride", "gliquidone", "glibornuride", "gliclazide", "glisoxepide", "tolbutamide" and "glipizide" as employed herein refers to the respective active drug or a pharmaceutically acceptable salt thereof.

The group G3 comprises glinides. Examples of glinides are nateglinide, repaglinide and mitiglinide. As their efficacy wears off over the course of treatment, a combination of a DPP-4 inhibitor with a meglitinide may offer additional benefit to the patient in terms of better glycemic control. Also, treatment with meglitinides is normally associated with gradual weight gain over the course of treatment and a DPP-4 inhibitor may minimize this side effect of the treatment with an meglitinide and/or improve the metabolic syndrome. Also, a DPP-4 inhibitor in combination with a meglitinide may minimize hypoglycemia which is another undesirable side effect of meglitinides. This combination may also allow a reduction in the dose of meglitinides, which may also translate into less hypoglycemia.

The term "nateglinide" as employed herein refers to nateglinide, including its enantiomers, mixtures thereof and its racemate, or a pharmaceutically acceptable salts and esters thereof.

The term "repaglinide" as employed herein refers to repaglinide, including its enantiomers, mixtures thereof and its racemate, or a pharmaceutically acceptable salts and esters thereof.

The group G3 comprises inhibitors of alpha-glucosidase. Examples of inhibitors of alpha-glucosidase are acarbose, voglibose and miglitol. Additional benefits from the combination of a DPP-4 inhibitor and an alpha-glucosidase inhibitor may relate to more efficacious glycemic control, e.g. at lower doses of the individual drugs, and/or reducement of undesirable gastrointestinal side effects of alpha-glucosidase inhibitors.

Each term of the group "acarbose", "voglibose" and "miglitol" as employed herein refers to the respective active drug or a pharmaceutically acceptable salt thereof.

The group G3 comprises inhibitors of GLP-1 analogues. Examples of GLP-1 analogues are exenatide, liraglutide, taspoglutide, semaglutide, albiglutide, and lixisenatide. The combination of a DPP-4 inhibitor and a GLP-1 analogue may achieve a superior glycemic control, e.g. at lower doses of the individual drugs. In addition, e.g. the body weight reducing capability of the GLP-1 analogue may be positively act together with the properties of the DPP-4 inhibitor. On the other hand, a reduction of side effects (e.g. nausea, gastrointestinal side effects like vomiting) may be obtained, e.g. when a reduced dose of the GLP-1 analogue is applied in the combination with a DPP-4 inhibitor.

Each term of the group "exenatide", "liraglutide", "taspoglutide", "semaglutide", "albiglutide", and "lixisenatide" as employed herein refers to the respective active drug or a pharmaceutically acceptable salt thereof.

In an embodiment (embodiment E1) the pharmaceutical compositions, combinations, methods and uses according to this invention relate to those combinations wherein the DPP-4 inhibitor and the second antidiabetic agent are preferably selected according to the entries in the Table 1.

TABLE 1

| DPP-4 Inhibitor | Second Antidiabetic Agent |
| --- | --- |
| selected from embodiment B | selected from the group G3 |
| selected from embodiment B | Metformin |
| selected from embodiment B | Pioglitazone |
| selected from embodiment B | Rosiglitazone |
| selected from embodiment B | Glibenclamide |
| selected from embodiment B | Glimepiride |
| selected from embodiment B | Gliquidone |
| selected from embodiment B | Nateglinide |
| selected from embodiment B | Repaglinide |
| selected from embodiment B | Acarbose |
| selected from embodiment B | Voglibose |
| selected from embodiment B | Miglitol |
| selected from embodiment B | Exenatide |
| selected from embodiment B | Liraglutide |
| selected from embodiment B | Taspoglutide |
| selected from embodiment B | Semaglutide |
| selected from embodiment B | Albiglutide |
| selected from embodiment B | Lixisenatide |
| Linagliptin | selected from the group G3 |
| Linagliptin | Metformin |
| Linagliptin | Pioglitazone |
| Linagliptin | Rosiglitazone |
| Linagliptin | Glibenclamide |
| Linagliptin | Glimepiride |
| Linagliptin | Gliquidone |
| Linagliptin | Nateglinide |
| Linagliptin | Repaglinide |
| Linagliptin | Acarbose |
| Linagliptin | Voglibose |
| Linagliptin | Miglitol |
| Linagliptin | Exenatide |
| Linagliptin | Liraglutide |
| Linagliptin | Taspoglutide |
| Linagliptin | Semaglutide |
| Linagliptin | Albiglutide |
| Linagliptin | Lixisenatide |
| Sitagliptin | selected from the group G3 |
| Sitagliptin | Metformin |
| Sitagliptin | Pioglitazone |
| Sitagliptin | Rosiglitazone |
| Sitagliptin | Glibenclamide |
| Sitagliptin | Glimepiride |
| Sitagliptin | Gliquidone |
| Sitagliptin | Nateglinide |
| Sitagliptin | Repaglinide |
| Sitagliptin | Acarbose |
| Sitagliptin | Voglibose |
| Sitagliptin | Miglitol |
| Sitagliptin | Exenatide |
| Sitagliptin | Liraglutide |
| Sitagliptin | Taspoglutide |
| Sitagliptin | Semaglutide |
| Sitagliptin | Albiglutide |
| Sitagliptin | Lixisenatide |

TABLE 1-continued

| DPP-4 Inhibitor | Second Antidiabetic Agent |
|---|---|
| Vildagliptin | selected from the group G3 |
| Vildagliptin | Metformin |
| Vildagliptin | Pioglitazone |
| Vildagliptin | Rosiglitazone |
| Vildagliptin | Glibenclamide |
| Vildagliptin | Glimepiride |
| Vildagliptin | Gliquidone |
| Vildagliptin | Nateglinide |
| Vildagliptin | Repaglinide |
| Vildagliptin | Acarbose |
| Vildagliptin | Voglibose |
| Vildagliptin | Miglitol |
| Vildagliptin | Exenatide |
| Vildagliptin | Liraglutide |
| Vildagliptin | Taspoglutide |
| Vildagliptin | Semaglutide |
| Vildagliptin | Albiglutide |
| Vildagliptin | Lixisenatide |
| Alogliptin | selected from the group G3 |
| Alogliptin | Metformin |
| Alogliptin | Pioglitazone |
| Alogliptin | Rosiglitazone |
| Alogliptin | Glibenclamide |
| Alogliptin | Glimepiride |
| Alogliptin | Gliquidone |
| Alogliptin | Nateglinide |
| Alogliptin | Repaglinide |
| Alogliptin | Acarbose |
| Alogliptin | Voglibose |
| Alogliptin | Miglitol |
| Alogliptin | Exenatide |
| Alogliptin | Liraglutide |
| Alogliptin | Taspoglutide |
| Alogliptin | Semaglutide |
| Alogliptin | Albiglutide |
| Alogliptin | Lixisenatide |
| Saxagliptin | selected from the group G3 |
| Saxagliptin | Metformin |
| Saxagliptin | Pioglitazone |
| Saxagliptin | Rosiglitazone |
| Saxagliptin | Glibenclamide |
| Saxagliptin | Glimepiride |
| Saxagliptin | Gliquidone |
| Saxagliptin | Nateglinide |
| Saxagliptin | Repaglinide |
| Saxagliptin | Acarbose |
| Saxagliptin | Voglibose |
| Saxagliptin | Miglitol |
| Saxagliptin | Exenatide |
| Saxagliptin | Liraglutide |
| Saxagliptin | Taspoglutide |
| Saxagliptin | Semaglutide |
| Saxagliptin | Albiglutide |
| Saxagliptin | Lixisenatide |
| Carmegliptin | selected from the group G3 |
| Carmegliptin | Metformin |
| Carmegliptin | Pioglitazone |
| Carmegliptin | Rosiglitazone |
| Carmegliptin | Glibenclamide |
| Carmegliptin | Glimepiride |
| Carmegliptin | Gliquidone |
| Carmegliptin | Nateglinide |
| Carmegliptin | Repaglinide |
| Carmegliptin | Acarbose |
| Carmegliptin | Voglibose |
| Carmegliptin | Miglitol |
| Carmegliptin | Exenatide |
| Carmegliptin | Liraglutide |
| Carmegliptin | Taspoglutide |
| Carmegliptin | Semaglutide |
| Carmegliptin | Albiglutide |
| Carmegliptin | Lixisenatide |
| Melogliptin | selected from the group G3 |
| Melogliptin | Metformin |
| Melogliptin | Pioglitazone |
| Melogliptin | Rosiglitazone |
| Melogliptin | Glibenclamide |
| Melogliptin | Glimepiride |
| Melogliptin | Gliquidone |
| Melogliptin | Nateglinide |
| Melogliptin | Repaglinide |
| Melogliptin | Acarbose |
| Melogliptin | Voglibose |
| Melogliptin | Miglitol |
| Melogliptin | Exenatide |
| Melogliptin | Liraglutide |
| Melogliptin | Taspoglutide |
| Melogliptin | Semaglutide |
| Melogliptin | Albiglutide |
| Melogliptin | Lixisenatide |
| Dutogliptin | selected from the group G3 |
| Dutogliptin | Metformin |
| Dutogliptin | Pioglitazone |
| Dutogliptin | Rosiglitazone |
| Dutogliptin | Glibenclamide |
| Dutogliptin | Glimepiride |
| Dutogliptin | Gliquidone |
| Dutogliptin | Nateglinide |
| Dutogliptin | Repaglinide |
| Dutogliptin | Acarbose |
| Dutogliptin | Voglibose |
| Dutogliptin | Miglitol |
| Dutogliptin | Exenatide |
| Dutogliptin | Liraglutide |
| Dutogliptin | Taspoglutide |
| Dutogliptin | Semaglutide |
| Dutogliptin | Albiglutide |
| Dutogliptin | Lixisenatide |
| Gosogliptin | selected from the group G3 |
| Gosogliptin | Metformin |
| Gosogliptin | Pioglitazone |
| Gosogliptin | Rosiglitazone |
| Gosogliptin | Glibenclamide |
| Gosogliptin | Glimepiride |
| Gosogliptin | Gliquidone |
| Gosogliptin | Nateglinide |
| Gosogliptin | Repaglinide |
| Gosogliptin | Acarbose |
| Gosogliptin | Voglibose |
| Gosogliptin | Miglitol |
| Gosogliptin | Exenatide |
| Gosogliptin | Liraglutide |
| Gosogliptin | Taspoglutide |
| Gosogliptin | Semaglutide |
| Gosogliptin | Albiglutide |
| Gosogliptin | Lixisenatide |
| Teneligliptin | selected from the group G3 |
| Teneligliptin | Metformin |
| Teneligliptin | Pioglitazone |
| Teneligliptin | Rosiglitazone |
| Teneligliptin | Glibenclamide |
| Teneligliptin | Glimepiride |
| Teneligliptin | Gliquidone |
| Teneligliptin | Nateglinide |
| Teneligliptin | Repaglinide |
| Teneligliptin | Acarbose |
| Teneligliptin | Voglibose |
| Teneligliptin | Miglitol |
| Teneligliptin | Exenatide |
| Teneligliptin | Liraglutide |
| Teneligliptin | Taspoglutide |
| Teneligliptin | Semaglutide |
| Teneligliptin | Albiglutide |
| Teneligliptin | Lixisenatide |

In a particular embodiment (embodiment E2) the pharmaceutical compositions, combinations, methods and uses according to this invention relate to those combinations wherein the DPP-4 inhibitor is linagliptin. According to embodiment E2 the second antidiabetic agent is preferably selected according to the entries in the Table 2.

TABLE 2

| Embodiment | Second Antidiabetic Agent |
| --- | --- |
| E2.1 | selected from the group G3 |
| E2.2 | Metformin |
| E2.3 | Pioglitazone |
| E2.4 | Rosiglitazone |
| E2.5 | Glibenclamide |
| E2.6 | Glimepiride |
| E2.7 | Gliquidone |
| E2.8 | Nateglinide |
| E2.9 | Repaglinide |
| E2.10 | Acarbose |
| E2.11 | Voglibose |
| E2.12 | Miglitol |
| E2.13 | Exenatide |
| E2.14 | Liraglutide |
| E2.15 | Taspoglutide |
| E2.16 | Semaglutide |
| E2.17 | Albiglutide |
| E2.18 | Lixisenatide |
| E2.19 | insulin or insulin analogue |
| E2.20 | GLP-1 or GLP-1 analogue |

The combination of a DPP-4 inhibitor and a second and, optionally, a third antidiabetic agent according to this invention can be found to improve the glycemic control, in particular in patients as described herein, compared with a monotherapy using either a DPP-4 inhibitor or the second or third antidiabetic agent alone, for example with a monotherapy of metformin, or with a dual therapy using the second and third antidiabetic agent. Further, the triple combination of a DPP-4 inhibitor and a second and a third antidiabetic agent according to this invention can be found to improve the glycemic control, in particular in patients as described herein, compared with a combination therapy using a DPP-4 inhibitor and either the second or third antidiabetic agent, or using the second and the third antidiabetic agent. The improved glycemic control is determined as an increased lowering of blood glucose and an increased reduction of HbA1c. With monotherapy in a patient, in particular in patients as described herein, the glycemic control may not be further improved significantly by an administration of the drug above a certain highest dose. In addition, a long term treatment using a highest dose may be unwanted in view of potential side effects. Therefore, a satisfying glycemic control may not be achievable in all patients via a monotherapy using either the DPP-4 inhibitor or the second or the third antidiabetic agent alone. In the case that monotherapy do not yield in full glycemic control, dual therapy may become necessary. Even with combination therapy using two agents selected from the DPP-4 inhibitors and second and third antidiabetic agents may not yield in a full glycemic control in all patients and/or over a long time. In the case that dual therapy do not yield in full glycemic control, triple therapy may become necessary. In such patients with inadequate glycemic control a progression of the diabetes mellitus may continue and complications associated with diabetes mellitus may occur, such as macrovascular complications. The pharmaceutical composition or combination as well as the methods according to the present invention allow a reduction of the HbA1c value to a desired target range, for example <7% and preferably <6.5%, for a higher number of patients and for a longer time of therapeutic treatment, e.g. in the case of dual or triple combination therapy compared with a monotherapy using one of or, respectively, a dual therapy using two of the combination partners.

In addition, the combination of a DPP-4 inhibitor and the second and, optionally, the third therapeutic agent according to this invention can be found to allow a reduction in the dose of either the DPP-4 inhibitor or the second or third antidiabetic agent or even of two or three of the active ingredients. A dose reduction is beneficial for patients which otherwise would potentially suffer from side effects in a therapy using a higher dose of one or more of the active ingredients, in particular with regard to side effect caused by the second and/or third antidiabetic agent. Therefore, the pharmaceutical combination as well as the methods according to the present invention, may show less side effects, thereby making the therapy more tolerable and improving the patients compliance with the treatment.

A DPP-4 inhibitor according to the present invention is able—via the increases in active GLP-1 levels—to reduce the glucagon secretion in a patient. This will therefore limit the hepatic glucose production. Furthermore, the elevated active GLP-1 levels produced by the DPP-4 inhibitor will have beneficial effects on beta-cell regeneration and neogenesis. All these features of DPP-4 inhibitors may render a pharmaceutical composition or combination or method of this invention quite useful and therapeutically relevant.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older. Also in the scope of this invention, patients are adolescent humans, i.e. humans of age 10 to less than 18 years, preferably of age 13 to less than 18 years.

In one embodiment, patients in need of treatment or prevention as described herein can be identified by determining whether they have variation(s) (e.g. polymorphisms) in one or more genes associated with metabolic diseases and/or whether they have variation(s) (e.g. polymorphisms) in one or more of the genes selected from TCF7L2, KCNJ11, PPARG and GLP1R, in particular whether they are of TCF7L2 risk genotype as described herein.

In another embodiment, patients in need of treatment or prevention as described herein can be identified by determining whether they are of respective wild-type genotype, in particular whether they are of TCF7L2 wild genotype as described herein.

A particular sub-population of the patients in need of treatment or prevention as described herein, refers to those patients who have one or more single nucleotide polymorphisms (SNPs) in the gene coding for TCF7L2, especially a SNP selected from rs7903146, rs12255372 and rs10885406, especially rs7903146, in more particular, those patients who carry at least one T allele of SNP rs7903146 of TCF7L2, i.e. the CT genotype or TT genotype.

Another particular sub-population of the patients in need of treatment or prevention as described herein, refers to those patients who carry TCF7L2 rs7903146 CC wild genotype.

Thus, in an aspect of this invention, a treatment or prophylaxis according to this invention is suitable in those patients in need of such treatment or prophylaxis who are diagnosed of having variation(s) (e.g. polymorphisms) in one or more genes associated with metabolic diseases and/or variation(s) (e.g. SNPs) in one or more of the genes selected from TCF7L2, KCNJ11, PPARG and GLP1R, in particular of TCF7L2 risk genotype as described herein.

In another aspect of this invention, a treatment or prophylaxis according to this invention is particular suitable in those patients in need of such treatment or prophylaxis who are diagnosed of having TCF7L2 wild genotype as described herein.

In an sub-aspect of this invention, a treatment or prophylaxis according to this invention is suitable in those patients in need of such treatment or prophylaxis who are diagnosed of having one or more single nucleotide polymorphisms (SNPs) in the gene coding for TCF7L2, e.g. at least one SNP selected from rs7903146, rs12255372 and rs10885406, for example rs7903146, in particular, carrying at least one T allele of rs7903146, (i.e. of CT or TT genotype), among them, in more particular, those carrying one T allele of rs7903146 (i.e. of CT risk genotype) or, in less particular, those carrying two T alleles of rs7903146 (i.e. of TT high risk genotype).

In another sub-aspect of this invention, a treatment or prophylaxis according to this invention is particular favorable in those patients in need of such treatment or prophylaxis who are diagnosed of carrying wild-type two C alleles of rs7903146 in TCF7L2 (i.e. of CC genotype).

In an embodiment of this invention, a treatment or prophylaxis according to this invention is suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. Any weight increasing effect in the therapy, for example due to the administration of the second and/or third antidiabetic agent, may be attenuated or even avoided thereby.

In a further embodiment of this invention, the pharmaceutical composition or combination of this invention exhibits a very good efficacy with regard to glycemic control, in particular in view of a reduction of fasting plasma glucose, postprandial plasma glucose and/or glycosylated hemoglobin (HbA1c). By administering a pharmaceutical composition or combination according to this invention, a reduction of HbA1c equal to or greater than preferably 1.0%, more preferably equal to or greater than 2.0%, even more preferably equal to or greater than 3.0% can be achieved and the reduction is particularly in the range from 1.0% to 3.0%.

Furthermore, the method and/or use according to this invention is applicable in those patients who show one, two or more of the following conditions:
(a) a fasting blood glucose or serum glucose concentration greater than 110 mg/dL or greater than 100 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition or combination for improving glycemic control in patients having type 2 diabetes or showing first signs of pre-diabetes. Thus, the invention also includes diabetes prevention. If therefore a pharmaceutical composition or combination of this invention is used to improve the glycemic control as soon as one of the above-mentioned signs of pre-diabetes is present, the onset of manifest type 2 diabetes mellitus can be delayed or prevented.

Furthermore, the pharmaceutical composition or combination of this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to an embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that a DPP-4 inhibitor and, optionally, a second and, optionally, a third antidiabetic agent as defined hereinbefore and hereinafter are administered, for example in combination, to the patient.

According to another embodiment of the present invention, there is provided a method for improving glycemic control in patients, in particular in adult patients, with type 2 diabetes mellitus as an adjunct to diet and exercise.

Moreover, in a particular embodiment of this invention, a therapeutic or preventive method and/or use according to this invention is suitable in those patients who have variation(s) (e.g. polymorphisms) in one or more genes associated with metabolic diseases and/or who have variation(s) (e.g. polymorphisms) in one or more of the genes selected from TCF7L2, KCNJ11, PPARG and GLP1R.

In this context, a sub-population of the patients described hereinbefore and hereinafter refers to TCF7L2 risk genotype patients, such as e.g. to those patients who have one or more single nucleotide polymorphisms (SNPs) in the gene coding for TCF7L2, especially at least one SNP selected from rs7903146, rs12255372 and rs10885406, especially rs7903146. In more particular, those patients who carry at least one T allele of SNP rs7903146 of TCF7L2, i.e. the CT genotype or TT genotype, especially who carry two T alleles of SNP rs7903146 of TCF7L2, i.e. the TT genotype, are strongly susceptible to increased TCF7L2 expression in pancreatic beta cells, impaired insulin secretion, incretine effects, enhanced rate of hepatic glucose production and/or diabetes. The T allele of rs7903146 TCF7L2 is associated with impaired insulinotropic action of incretin hormones, reduced 24 h profiles of plasma insulin and glucagon, and increased hepatic glucose production.

Therefore, the present invention also includes the compounds, pharmaceutical compositions or combinations according to this invention for use in the treatment and/or prevention of those diseases, disorders or conditions mentioned herein in those patients who have one or more single nucleotide polymorphisms (SNPs) in the gene coding for TCF7L2, especially at least one SNP selected from rs7903146, rs12255372 and rs10885406, especially rs7903146; in more particular, in those patients who carry at least one T allele of SNP rs7903146 of TCF7L2, i.e. the CT genotype or TT genotype, particularly in those patients who carry one T allele of SNP rs7903146 of TCF7L2, i.e. the CT genotype, or who carry two T alleles of SNP rs7903146 of TCF7L2, i.e. the TT genotype.

TCF7L2 risk genotype patients as described herein include, without being limited, patients of Caucasian, North European, East Asian, Indian and/or African descent.

The present invention further includes a therapeutic and/or preventive method or use according to this invention for application in a patient in need thereof, said method or use comprising the step of determining whether the patient has variation(s) (e.g. polymorphisms) in one or more of the genes selected from TCF7L2, KCNJ11, PPARG and GLP1R, particularly whether the patient is of a TCF7L2 risk genotype as described herein.

The determination or diagnosis whether the patient has variation(s) (e.g. polymorphisms) in one or more of the genes selected from TCF7L2, KCNJ11, PPARG and GLP1R, particularly whether the patient is of a TCF7L2 risk genotype as described herein, or whether the patient is of wild genotype, particularly whether the patient is of TCF7L2 wild genotype as described herein, may be used for determining the likelihood (e.g., increased, decreased, or no likelihood) of a favourable therapeutic and/or preventive response of the patient to the treatment with a DPP-4 inhibitor (or with a combination of a DPP-4 inhibitor with the second and/or third antidiabetic agent as defined herein) in a therapeutic and/or preventive method or use as described hereinabove or hereinbelow (e.g. in treating diabetes or in improving glycemic control), and thus for identifying a subject being susceptible to such treatment.

Thus, further on, in another embodiment of this invention, there is provided a method of determining the probability of likelihood (e.g., increased, decreased, or no likelihood) of a favourable response to the administration of a pharmaceutically acceptable amount of a DPP-4 inhibitor (or of a combination of a DPP-4 inhibitor with the second and/or third antidiabetic agent as described herein) in a subject (particularly diabetes patient), said method comprising the step of determining whether the subject has variation(s) (e.g. polymorphisms) in one or more of the genes selected from TCF7L2, KCNJ11, PPARG and GLP1R, particularly whether the subject is of a TCF7L2 risk genotype as described herein, or determining whether the subject is of TCF7L2 wild genotype, particularly testing whether the subject is of the TCF7L2 rs7903146 CC wild genotype.

According to another particular embodiment this invention, the present invention provides a DPP-4 inhibitor, a pharmaceutical composition or combination according to the present invention for use in a therapeutic or preventive method as described hereinbefore or hereinafter (particularly for treating or preventing type 2 diabetes and/or obesity), said method comprising
(i) identifying a subject being susceptible to the therapeutic or preventive method, said identifying comprising testing whether the subject has variation(s) (e.g. polymorphisms) in one or more of the genes selected from TCF7L2, KCNJ11, PPARG and GLP1R, in particular whether the subject is of any TCF7L2 risk genotype as described herein, in more particular whether he/she has one or more single nucleotide polymorphisms (SNPs) in the gene coding for TCF7L2, especially at least one SNP selected from rs7903146, rs12255372 and rs10885406, especially rs7903146, for example whether the subject carries at least one T allele of SNP rs7903146 of TCF7L2, e.g. whether the subject is of CT genotype (i.e. whether the patient carries one T allele of SNP rs7903146 of TCF7L2) or whether the subject is of TT genotype (i.e. whether the patient carries two T alleles of SNP rs7903146 of TCF7L2), or testing whether the subject is of TCF7L2 wild genotype, in particular whether the subject is of the TCF7L2 rs7903146 CC wild genotype; and thus determining the probability of likelihood of a favourable response (e.g. favorable change in HbA1c) resulting from therapeutic or preventive treatment of the subject with the DPP-4 inhibitor, pharmaceutical composition or combination;
and
(ii) administering an effective amount of the DPP-4 inhibitor, pharmaceutical composition or combination to the subject, where said subject is determined to have a high probability of likelihood of a favorable response (e.g. favorable change in HbA1c) resulting from therapeutic or preventive treatment with the DPP-4 inhibitor, pharmaceutical composition or combination.

The present invention further provides a therapeutic and/or preventive method or use of this invention for application in a patient in need thereof, said method or use comprising the steps of
obtaining and assaying a nucleic acid sample from an individual with type 2 diabetes mellitus,
determining the efficacy and/or, optionally, the probability of the likelihood of a favorable response (e.g. in providing glycemic control, such as favorable change in HbA1c) to a treatment with a DPP-4 inhibitor, preferably linagliptin, or the DPP-4 inhibitor in combination with one or more other active substances (e.g. antidiabetics), comprising detecting either TT or CT or CC allele genotype at rs7903146 of TCF7L2 gene in patient's sample,
wherein the presence of the TT, CT or CC genotype is indicative of the efficacy to the treatment, and/or, optionally,
wherein the presence of the TT genotype is indicative of a decreased likelihood of favorable response and/or presence of the CC genotype is indicative of an increased likelihood of favorable response to the treatment, and
administering a therapeutically effective amount of the DPP-4 inhibitor, preferably linagliptin, or the DPP-4 inhibitor in combination with one or more other active substances (e.g. antidiabetics) to the individual.

It can be further found that by using a pharmaceutical composition or combination according to this invention, an improvement of the glycemic control can be achieved even in those patients who have insufficient glycemic control in particular despite treatment with the second or third antidiabetic agent or a combination of the second with the third antidiabetic agent, for example despite maximal tolerated dose of oral monotherapy with metformin, a thiazolidinedione (e.g. pioglitazone) or a sulfonylurea, or a combination of metformin with a thiazolidinedione (e.g. pioglitazone), of metformin with a sulfonylurea, or of a thiazolidinedione (e.g. pioglitazone) with a sulfonylurea.

It can be also found that by using a combination according to this invention, an improvement of the glycemic control can be achieved even in those patients who have insufficient glycemic control in particular despite treatment with a DPP-4 inhibitor or a combination of a DPP-4 inhibitor with the second or third antidiabetic agent, for example despite maximal tolerated dose of oral monotherapy with a DPP-4 inhibitor or a dual combination of a DPP-4 inhibitor with the second or third antidiabetic agent.

A maximal tolerated dose with regard to metformin is for example 2000 mg per day, 1500 mg per day (for example in asian countries) or 850 mg three times a day or any equivalent thereof.

Therefore, the method and/or use according to this invention is applicable in those patients who show one, two or more of the following conditions:
(a) insufficient glycemic control with diet and exercise alone;
(b) insufficient glycemic control despite monotherapy with metformin, a thiazolidinedione (e.g. pioglitazone), a sulfonylurea, GLP-1 or GLP-1 analogue, or insulin or insulin analogue, in particular despite oral monotherapy at a maximal tolerated dose of metformin, a thiazolidinedione (e.g. pioglitazone) or a sulfonylurea;
(c) insufficient glycemic control despite combination therapy with two agents selected from the group consisting of metformin, a thiazolidinedione (e.g. pioglitazone), a sulfonylurea, GLP-1 or GLP-1 analogue, and insulin or insulin analogue, for example despite combination therapy with a dual combination selected from metformin/pioglitazone, metformin/sulphonylurea, metformin/insulin, sulphonylurea/pioglitazone, sulphonylurea/insulin and pioglitazone/insulin;

The dual or triple combination method and/or use according to this invention is further applicable in those patients who show the following conditions (e) or (f), respectively:
(d) insufficient glycemic control despite oral monotherapy with the DPP-4 inhibitor, in particular despite oral monotherapy at a maximal tolerated dose of the DPP-4 inhibitor;
(e) insufficient glycemic control despite (oral) combination therapy with the DPP-4 inhibitor and the second or third antidiabetic agent, in particular despite oral dual therapy at a maximal tolerated dose of at least one of the combination partners.

In an embodiment of this invention, a pharmaceutical composition or combination is suitable in the treatment of patients who are diagnosed having one or more of the following conditions
   insulin resistance,
   hyperinsulinemia,
   pre-diabetes,
   type 2 diabetes mellitus, particular having a late stage type 2 diabetes mellitus,
   type 1 diabetes mellitus.

Furthermore, a pharmaceutical composition or combination according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL or ≥100 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

Furthermore, the pharmaceutical composition and the methods according to this invention are particularly suitable in the treatment of patients after organ transplantation, in particular those patients who are diagnosed having one or more of the following conditions
(a) a higher age, in particular above 50 years,
(b) male gender;
(c) overweight, obesity (including class I, II and/or III obesity), visceral obesity and/or abdominal obesity,
(d) pre-transplant diabetes,
(e) immunosuppression therapy.

A pharmaceutical composition or combination according to this invention, in particular due to the DPP-4 inhibitor therein, exhibits a good safety profile. Therefore, a treatment or prophylaxis according to this invention is possible in those patients for which the mono-therapy with another antidiabetic drug, such as for example metformin, is contraindicated and/or who have an intolerance against such drugs at therapeutic doses. In particular, a treatment or prophylaxis according to this invention may be advantageously possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore, it can be found that the administration of a pharmaceutical composition or combination according to this invention results in no risk or in a low risk of hypoglycemia. Therefore, a treatment or prophylaxis according to this invention is also advantageously possible in those patients showing or having an increased risk for hypoglycemia.

A pharmaceutical composition or combination according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particular embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

The effects mentioned above are observed both, when the DPP-4 inhibitor and the second and, optionally, third antidiabetic agent are administered together, for example simultaneously in one single or two or three separate formulations, and/or when they are administered in alternation, for example successively in two or three separate formulations.

Within this invention it is to be understood that combinations or combined uses envisage the separate, sequential, simultaneous, concurrent, chronologically staggered or alternating administration of the components. It will be appreciated that the DPP-4 inhibitor and the other active substance(s) can be administered in a single dosage form or each in separate dosage forms.

In this context, "combination" or "combined" within the meaning of this invention also includes, without being limited, fixed and non-fixed forms and uses.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the DPP-4 inhibitor and, optionally, the second and/or third antidiabetic agent according to this invention are included in the pharmaceutical composition, combination or dosage form in an amount sufficient that by their administration the glycemic control in the patient to be treated is improved.

In the following preferred ranges of the amount of the DPP-4 inhibitor, the second and/or third antidiabetic agent to be employed in the pharmaceutical composition and the methods and uses according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient. The ranges of the dosage and amounts are calculated for the individual active moiety. Advantageously, the combination therapy of the present invention utilizes lower dosages of the individual DPP-4 inhibitor and/or of the individual second and/or third antidiabetic agent used in monotherapy or used in conventional therapeutics, thus avoiding possible toxicity and adverse side effects incurred when those agents are used as monotherapies.

Within the scope of the present invention, the pharmaceutical composition or combination is preferably administered orally. Other forms of administration are possible and described hereinafter. Preferably the one or more dosage forms comprising the DPP-4 inhibitor and/or the second and/or the third antidiabetic agent is oral or usually well known.

In general, the amount of the DPP-4 inhibitor in the combinations, combination methods or combined uses of this invention is preferably in the range from 1/5 to 1/1 of the amount usually recommended for a monotherapy using said DPP-4 inhibitor.

A preferred dosage range of linagliptin when administered orally is 0.5 mg to 10 mg per day, preferably 2.5 mg to 10 mg, most preferably 1 mg to 5 mg per day. The preferred range of amounts in the pharmaceutical composition is 0.5 to 10 mg, in particular 1 to 5 mg. Examples of particular dosage strengths are are 1, 2.5, 5 or 10 mg. The application of the active ingredient may occur up to three times a day, preferably one or two times a day. Suitable formulations for linagliptin may be those formulations disclosed in the application WO 2007/128724, the disclosure of which is incorporated herein in its entirety.

Typical dosage strengths of the dual fixed dose combination (tablet) of linagliptin/metformin IR (immediate release) are 2.5/500 mg, 2.5/850 mg and 2.5/1000 mg, which may be administered 1-3 times a day, particularly twice a day.

Typical dosage strengths of the dual fixed dose combination (tablet) of linagliptin/metformin XR (extended release) are 5/500 mg, 5/1000 mg and 5/1500 mg, which may be administered 1-2 times a day, particularly once a day, preferably to be taken in the evening with meal, or 2.5/500 mg, 2.5/750 mg and 2.5/1000 mg, which may be administered 1-2 times a day, particularly once a day two tablets, preferably to be taken in the evening with meal.

A preferred dosage range of sitagliptin when administered orally is from 10 to 200 mg, in particular 25 to 150 mg per day. A recommended dose of sitagliptin is 100 mg calculated for the active moiety (free base anhydrate) once daily or 50 mg twice daily. The preferred range of amounts in the pharmaceutical composition is 10 to 150 mg, in particular 25 to 100 mg. Examples are 25, 50, 75 or 100 mg. The application of the active ingredient may occur up to three times a day, preferably one or two times a day. Equivalent amounts of salts of sitagliptin, in particular of the phosphate monohydrate can be calculated accordingly. Adjusted dosages of sitagliptin, for example 25 and 50 mg, are preferably used for patients with renal failure.

A preferred dosage range of vildagliptin when administered orally is from 10 to 150 mg daily, in particular from 25 to 150 mg, 25 and 100 mg or 25 and 50 mg or 50 and 100 mg daily. For example the daily administration of vildagliptin is 50 or 100 mg. The preferred range of amounts in the pharmaceutical composition is 10 to 150 mg, in particular 25 to 100 mg. Examples are 25, 50, 75 or 100 mg. The application of the active ingredient may occur up to three times a day, preferably one or two times a day.

A preferred dosage range of alogliptin when administered orally is from 5 to 250 mg daily, in particular from 10 to 150 mg daily. The preferred range of amounts in the pharmaceutical composition is 5 to 150 mg, in particular 10 to 100 mg. Examples are 10, 12.5, 20, 25, 50, 75 and 100 mg. The application of the active ingredient may occur up to three times a day, preferably one or two times a day.

A preferred dosage range of saxagliptin when administered orally is from 2.5 to 100 mg daily, in particular from 2.5 to 50 mg daily. The preferred range of amounts in the pharmaceutical composition is from 2.5 to 100 mg, in particular from 2.5 and 50 mg. Examples are 2.5, 5, 10, 15, 20, 30, 40, 50 and 100 mg. The application of the active ingredient may occur up to three times a day, preferably one or two times a day.

A preferred dosage range of dutogliptin when administered orally is from 50 to 400 mg daily, in particular from 100 to 400 mg daily. The preferred range of amounts in the pharmaceutical composition is from 50 to 400 mg. Examples are 50, 100, 200, 300 and 400 mg. The application of the active ingredient may occur up to three times a day, preferably one or two times a day.

A special embodiment of the DPP-4 inhibitors of this invention refers to those orally administered DPP-4 inhibitors which are therapeutically efficacious at low dose levels, e.g. at dose levels <100 mg or <70 mg per patient per day, preferably <50 mg, more preferably <30 mg or <20 mg, even more preferably from 1 mg to 10 mg (if required, divided into 1 to 4 single doses, particularly 1 or 2 single doses, which may be of the same size), particularly from 1 mg to 5 mg (more particularly 5 mg), per patient per day, preferentially, administered orally once-daily, more preferentially, at any time of day, administered with or without food. Thus, for example, the daily oral amount 5 mg BI 1356 can be given in a once daily dosing regimen (i.e. 5 mg BI 1356 once daily) or in a twice daily dosing regimen (i.e. 2.5 mg BI 1356 twice daily), at any time of day, with or without food.

In general, the amount of the the second and/or third antidiabetic agent in the combinations, combination methods and/or combined uses of this invention is preferably in the range from 1/5 to 1/1 of the amount usually recommended for a monotherapy using said antidiabetic agent. Using lower dosages of the individual second and/or third antidiabetic agent compared with monotherapy could avoid or minimize possible toxicity and adverse side effects incurred when those agents are used as monotherapies.

A preferred dosage range of metformin when administered orally is 250 to 3000 mg, in particular 500 to 2000 mg per day. The preferred range of amounts in the pharmaceutical composition is 250 to 1000, in particular 500 to 1000 mg or 250 to 850 mg respectively. Examples are 500, 750, 850 or 1000 mg. Preferably the administration of said amounts is once, twice or three times daily. For example the amounts of 500, 750 and 850 mg preferably require once-daily, twice-daily or three-times daily dosing and the amount of 1000 mg preferably requires once-daily or twice-daily dosing. Certain controlled or sustained release formulations allow a once-daily dosing. Metformin can be administered for example in the form as marketed under the trademarks GLUCOPHAGE™, GLUCOPHAGE-D™ or GLUCOPHAGE-XR™.

A preferred dosage range of pioglitazone when administered orally is 5 to 50 mg per day. The preferred range of amounts in the pharmaceutical composition is 5 to 50 mg, 10 to 45 mg and 15 to 45 mg respectively. Examples are 15, 30 or 45 mg. Preferably the administration of said amounts is once or twice daily, in particular once daily. Pioglitazone can be administered in the form as it is marketed for example under the trademark ACTOS™.

A preferred dosage range of rosiglitazone when administered orally is 1 mg to 10 mg per day. The preferred range of amounts in the pharmaceutical composition is 1 to 10 mg, 2 to 8 mg, 4 to 8 mg and 1 to 4 mg. Examples are 1, 2, 4 or 8 mg. Preferably the administration of said amounts is once or twice daily. Preferably the dose should not exceed 8 mg daily. Rosiglitazone can be administered in the form as it is marketed for example under the trademark AVANDIA™.

A preferred dosage range of a thiazolidindione (other than pioglitazone or rosiglitazone as described above) when administered orally is 2 to 100 mg per day. The preferred range of amounts in the pharmaceutical composition for an administration once, twice or three times daily is 2 to 100, 1 to 50 and 1 to 33 mg respectively.

A preferred dosage range of glibenclamide when administered orally is 0.5 to 15 mg, in particular 1 to 10 mg per day. The preferred range of amounts in the pharmaceutical composition is 0.5 to 5 mg, in particular 1 to 4 mg. Examples are 1.0, 1.75 and 3.5 mg. Preferably the administration of said amounts is once, twice or three-times daily. Glibenclamide can be administered in the form as it is marketed for example under the trademark EUGLUCON™.

A preferred dosage range of glimepiride when administered orally is 0.5 to 10 mg, in particular 1 to 6 mg per day. The preferred range of amounts in the pharmaceutical composition is 0.5 to 10 mg, in particular 1 to 6 mg. Examples are 1, 2, 3, 4, and 6 mg. Preferably the administration of said amounts is once, twice or three-times daily, preferably once daily. Glimepiride can be administered in the form as it is marketed for example under the trademark AMARYL™.

A preferred dosage range of gliquidone when administered orally is 5 to 150 mg, in particular 15 to 120 mg per day. The preferred range of amounts in the pharmaceutical composition is 5 to 120 mg, in particular 5 to 30 mg. Examples are 10, 20, 30 mg. Preferably the administration of said amounts is once, twice, three-times or four-times daily. Gliquidone can be administered in the form as it is marketed for example under the trademark GLURENORM™.

A preferred dosage range of glibornuride when administered orally is 5 to 75 mg per day. The preferred range of amounts in the pharmaceutical composition is 5 to 75 mg, in particular 10 to 50 mg. Preferably the administration of said amounts is once, twice or three-times daily.

A preferred dosage range of gliclazide when administered orally is 20 to 300 mg, in particular 40 to 240 mg per day. The preferred range of amounts in the pharmaceutical composition is 20 to 240 mg, in particular 20 to 80 mg. Examples are 20, 30, 40 and 50 mg. Preferably the administration of said amounts is once, twice or three-times daily.

A preferred dosage range of glisoxepide when administered orally is 1 to 20 mg, in particular 1 to 16 mg per day. The preferred range of amounts in the pharmaceutical composition is 1 to 8 mg, in particular 1 to 4 mg. Preferably the administration of said amounts is once, twice, three-times or four-times daily.

A preferred dosage range of tolbutamide when administered orally is 100 to 3000 mg, preferably 500 to 2000 mg per day. The preferred range of amounts in the pharmaceutical composition is 100 to 1000 mg. Preferably the administration of said amounts is once or twice daily.

A preferred dosage range of glipizide when administered orally is 1 to 50 mg, in particular 2.5 to 40 mg per day. The preferred range of amounts in the pharmaceutical composition for an administration once, twice or three times daily is 1 to 50, 0.5 to 25 and 0.3 to 17 mg respectively.

A preferred dosage range of nateglinide when administered orally is 30 to 500 mg, in particular 60 to 360 mg per day. The preferred range of amounts in the pharmaceutical composition is 30 to 120 mg. Examples are 30, 60 and 120 mg. Preferably the administration of said amounts is once, twice or three-times daily. Nateglinide can be administered in the form as it is marketed for example under the trademark STARLIX™.

A preferred dosage range of repaglinide when administered orally is 0.1 to 16 mg, in particular 0.5 to 6 mg per day. The preferred range of amounts in the pharmaceutical composition is 0.5 to 4 mg. Examples are 0.5, 1, 2 or 4 mg. Preferably the administration of said amounts is once, twice, three-times or four-times daily. Repaglinide can be administered in the form as it is marketed for example under the trademark NOVONORM™.

A preferred dosage range of acarbose when administered orally is 50 to 1000 mg, in particular 50 to 600 mg per day. The preferred range of amounts in the pharmaceutical composition is 50 to 150 mg. Examples are 50 and 100 mg. Preferably the administration of said amounts is once, twice, three-times or four-times daily. Acarbose can be administered in the form as it is marketed for example under the trademark Glucobay™.

A preferred dosage range of voglibose when administered orally is 100 to 1000 mg, in particular 200 to 600 mg per day. The preferred range of amounts in the pharmaceutical composition is 50 to 300 mg. Examples are 50, 100, 150, 200 and 300 mg. Preferably the administration of said amounts is once, twice, three-times or four-times daily. Voglibose can be administered in the form as it is marketed for example under the trademark Basen™ or Voglisan™.

A preferred dosage range of miglitol when administered orally is 25 to 500 mg, in particular 25 to 300 mg per day. The preferred range of amounts in the pharmaceutical composition is 25 to 100 mg. Examples are 25, 50 and 100 mg. Preferably the administration of said amounts is once, twice, three-times or four-times daily. Miglitol can be administered in the form as it is marketed for example under the trademark Glyset™.

A preferred dosage range of GLP-1 analogues, in particular of exenatide is 5 to 30 µg, in particular 5 to 20 µg per day. The preferred range of amounts in the pharmaceutical composition is 5 to 10 µg. Examples are 5 and 10 µg. Preferably the administration of said amounts is once, twice, three-times or four-times daily by subcutaneous injection. Exenatide can be administered in the form as it is marketed for example under the trademark Byetta™. A long acting formulation, preferably for a once weekly subcutaneous injection, comprises an amount from 0.1 to 3.0 mg, preferably 0.5 to 2.0 mg exenatide. Examples are 0.8 mg and 2.0 mg. An example of a long acting formulation of exenatide is Byetta LAR™.

A preferred dosage range of liraglutide is 0.5 to 3 mg, in particular 0.5 to 2 mg per day. The preferred range of amounts in the pharmaceutical composition is 0.5 to 2 mg. Examples are 0.6, 1.2 and 1.8 mg. Preferably the administration of said amounts is once or twice daily by subcutaneous injection.

The amount of the DPP-4 inhibitor and the second and/or third therapeutic agent in the pharmaceutical composition and in the methods and uses of this invention correspond to the respective dosage ranges as provided hereinbefore. For example, preferred dosage ranges in a pharmaceutical composition, combination, method and use according to this invention are an amount of 0.5 to 10 mg (in particular 1 to 5 mg, especially 2.5 mg or 5 mg) of linagliptin and/or, optionally, an amount of 250 to 1000 mg (especially 500 mg, 850 mg or 1000 mg) of metformin. An oral administration once or twice daily is preferred.

In the combination methods and combined uses according to the present invention the DPP-4 inhibitor and the second and/or third therapeutic agent are administered in combination including, without being limited, the active ingredients are administered at the same time, i.e. simultaneously, or essentially at the same time, or the active ingredients are administered in alternation, i.e. that at first one or two active ingredients are administered and after a period of time the other two or one active ingredients are administered, i.e. at least two of the three active ingredients are administered sequentially. The period of time may be in the range from 30 min to 12 hours. The administration which is in combination or in alternation may be once, twice, three times or four times daily, preferably once or twice daily.

With regard to combined administration of the DPP-4 inhibitor and the second and/or third antidiabetic agent, all three active ingredients may be present in one single dosage form, for example in one tablet or capsule, or one or two of the active ingredients may be present in a separate dosage form, for example in two different or identical dosage forms.

With regard to their administration in alternation, one or two of the active ingredients are present in a separate dosage form, for example in two different or identical dosage forms.

Therefore, a pharmaceutical combination of this invention may be present as single dosage forms which comprise the DPP-4 inhibitor and the second and, optionally, the third antidiabetic agent. Alternatively a pharmaceutical combination of this invention may be present as two separate dosage forms wherein one dosage form comprises the DPP-4 inhibitor and the other dosage form comprises the second plus, optionally, the third antidiabetic agent, or, in case of a triple combination, one dosage form comprises the DPP-4 inhibitor inhibitor plus either the second or the third antidiabetic agent and the other dosage form comprises the third or the second antidiabetic agent, respectively. Alternatively, in case of a triple combination, a pharmaceutical combination of this invention may be present as three separate dosage forms wherein one dosage form comprises the DPP-4 inhibitor and a second dosage form comprises the second antidiabetic agent and the third dosage form comprises the third antidiabetic agent. Alternatively, in case of a dual combination, a pharmaceutical combination of this invention may be present as two separate dosage forms wherein one dosage form comprises the DPP-4 inhibitor and the second dosage form comprises the second antidiabetic agent.

The case may arise in which an active ingredient has to be administered more often, for example twice per day, than the other active ingredient(s), which for example needs administration once daily. Therefore "administration in combination" also includes an administration scheme in which first all active ingredients are administered in combination and after a period of time an active ingredient is administered again or vice versa.

Therefore, the present invention also includes pharmaceutical combinations which are present in separate dosage forms wherein one dosage form comprises the DPP-4 inhibitor and the second and, optionally, the third, therapeutic agent and the other dosage form comprises the second and/or the third therapeutic agent only.

Thus, the present invention also includes pharmaceutical compositions or combinations for separate, sequential, simultaneous, concurrent, alternate or chronologically staggered use of the active ingredients or components.

A pharmaceutical composition which is present as a separate or multiple dosage form, preferably as a kit of parts, is useful in combination therapy to flexibly suit the individual therapeutic needs of the patient.

According to a first embodiment a kit of parts comprises
(a) a first containment containing a dosage form comprising the DPP-4 inhibitor and at least one pharmaceutically acceptable carrier, and
(b) a second containment containing a dosage form comprising the second antidiabetic agent and at least one pharmaceutically acceptable carrier, and, optionally,
(c) a third containment containing a dosage form comprising the third antidiabetic agent and at least one pharmaceutically acceptable carrier.

According to a second embodiment a kit of parts comprises
(a) a first containment containing a dosage form comprising the DPP-4 inhibitor and the second or third antidiabetic agent and at least one pharmaceutically acceptable carrier, and
(b) a second containment containing a dosage form comprising the third or second antidiabetic agent, respectively, and at least one pharmaceutically acceptable carrier.

According to a third embodiment a kit of parts comprises
(a) a first containment containing a dosage form comprising the DPP-4 inhibitor and at least one pharmaceutically acceptable carrier, and
(b) a second containment containing a dosage form comprising the second and third antidiabetic agent and at least one pharmaceutically acceptable carrier.

A further aspect of the present invention is a manufacture comprising the pharmaceutical combination being present as separate dosage forms according to the present invention and a label or package insert comprising instructions that the separate dosage forms are to be administered in combination.

According to a first embodiment a manufacture comprises (a) a pharmaceutical composition comprising a DPP-4 inhibitor according to the present invention and (b) a label or package insert which comprises instructions that the medicament may or is to be administered, for example in combination, with a medicament comprising a second antidiabetic agent according to the present invention or with a fixed or free combination (e.g. a medicament) comprising a second antidiabetic agent and a third antidiabetic agent according to the present invention.

According to a second embodiment a manufacture comprises (a) a second antidiabetic agent according to the present invention and (b) a label or package insert which comprises instructions that the medicament may or is to be administered, for example in combination, with a medicament comprising a DPP-4 inhibitor according to the present invention or with a a fixed or free-combination (e.g. a medicament) comprising a DPP-4 inhibitor and a third antidiabetic agent according to the present invention.

According to a third embodiment a manufacture comprises (a) a pharmaceutical composition comprising a DPP-4 inhibitor and a second antidiabetic agent according to the present invention and (b) a label or package insert which comprises instructions that the medicament may or is to be administered, for example in combination, with a medicament comprising a third antidiabetic agent according to the present invention.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, subcutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers. Preferred carriers must be "acceptable" in the sense of being compatible with the other ingredients of the formulation and not deleterious to the recipient thereof. Examples of pharmaceutically acceptable carriers are known to the one skilled in the art.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

For pharmaceutical application in warm-blooded vertebrates, particularly humans, the compounds of this invention are usually used in dosages from 0.001 to 100 mg/kg body weight, preferably at 0.1-15 mg/kg, in each case 1 to 4 times a day. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The pharmaceutical compositions according to this invention comprising the DPP-4 inhibitors as defined herein are thus prepared by the skilled person using pharmaceutically acceptable formulation excipients as described in the art. Examples of such excipients include, without being restricted to diluents, binders, carriers, fillers, lubricants, flow promoters, crystallisation retardants, disintegrants, solubilizers, colorants, pH regulators, surfactants and emulsifiers.

Examples of suitable diluents for compounds according to embodiment A include cellulose powder, calcium hydrogen phosphate, erythritol, low substituted hydroxypropyl cellulose, mannitol, pregelatinized starch or xylitol. Among those diluents mannitol, low substituted hydroxypropyl cellulose and pregelatinized starch are to be emphasized.

Examples of suitable lubricants for compounds according to embodiment A include talc, polyethyleneglycol, calcium behenate, calcium stearate, hydrogenated castor oil or magnesium stearate. Among those lubricants magnesium stearate is to be emphasized.

Examples of suitable binders for compounds according to embodiment A include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC). Among those binders copovidone and pregelatinized starch are to be emphasized.

Examples of suitable disintegrants for compounds according to embodiment A include corn starch or crospovidone. Among those disintegrants corn starch is to be emphasized.

Suitable methods of preparing pharmaceutical formulations of the DPP-4 inhibitors according to embodiment A of the invention are direct tabletting of the active substance in powder mixtures with suitable tabletting excipients;

granulation with suitable excipients and subsequent mixing with suitable excipients and subsequent tabletting as well as film coating; or packing of powder mixtures or granules into capsules.

Suitable granulation methods are wet granulation in the intensive mixer followed by fluidised bed drying;

one-pot granulation;

fluidised bed granulation; or dry granulation (e.g. by roller compaction) with suitable excipients and subsequent tabletting or packing into capsules.

An exemplary composition of a DPP-4 inhibitor according to embodiment A of the invention comprises the first diluent mannitol, pregelatinized starch as a second diluent with additional binder properties, the binder copovidone, the disintegrant corn starch, and magnesium stearate as lubricant; wherein copovidone and/or corn starch may be optional.

For details on dosage forms, formulations and administration of DPP-4 inhibitors of this invention, reference is made to scientific literature and/or published patent documents, particularly to those cited herein.

The pharmaceutical compositions (or formulations) may be packaged in a variety of ways. Generally, an article for distribution includes a container that contains the pharmaceutical composition in an appropriate form. Tablets are typically packed in an appropriate primary package for easy handling, distribution and storage and for assurance of proper stability of the composition at prolonged contact with the environment during storage. Primary containers for tablets may be bottles or blister packs.

A suitable bottle, e.g. for a pharmaceutical composition or combination comprising a DPP-4 inhibitor according to embodiment A of the invention, may be made from glass or polymer (preferably polypropylene (PP) or high density polyethylene (HD-PE)) and sealed with a screw cap. The screw cap may be provided with a child resistant safety closure (e.g. press-and-twist closure) for preventing or hampering access to the contents by children. If required (e.g. in regions with high humidity), by the additional use of a desiccant (such as e.g. bentonite clay, molecular sieves, or, preferably, silica gel) the shelf life of the packaged composition can be prolonged.

A suitable blister pack, e.g. for a pharmaceutical composition or combination comprising a DPP-4 inhibitor according to embodiment A of the invention, comprises or is formed of a top foil (which is breachable by the tablets) and a bottom part (which contains pockets for the tablets). The top foil may contain a metallic foil, particularly an aluminium or aluminium alloy foil (e.g. having a thickness of 20 µm to 45 µm, preferably 20 µm to 25 µm) that is coated with a heat-sealing polymer layer on its inner side (sealing side). The bottom part may contain a multi-layer polymer foil (such as e.g. poly(vinyl chloride) (PVC) coated with poly(vinylidene chloride) (PVDC); or a PVC foil laminated with poly(chlorotriflouroethylene) (PCTFE)) or a multi-layer polymer-metal-polymer foil (such as e.g. a cold-formable laminated PVC/aluminium/polyamide composition).

The article may further comprise a label or package insert, which refer to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described herein.

The pharmaceutical compositions and methods according to this invention show advantageous effects in the treatment and prevention of those diseases and conditions as described hereinbefore. The dual combinations show advantageous effects compared with monotherapy with an active ingredient. The triple combinations show advantageous effects compared with dual therapy with one or two of the three active ingredients. Advantageous effects may be seen for example with respect to efficacy, dosage strength, dosage frequency, pharmacodynamic properties, pharmacokinetic properties, fewer adverse effects, convenience, compliance, etc.

With respect to linagliptin, the methods of synthesis are known to the skilled person and as described in the literature, in particular as described in WO 2002/068420, WO 2004/018468, or WO 2006/048427, the disclosures of which are incorporated herein. Polymorphous crystal modifications and formulations of particular DPP-4 inhibitors are disclosed in WO 2007/128721 and WO 2007/128724, respectively, the disclosures of which are incorporated herein in their entireties. Formulations of particular DPP-4 inhibitors with metformin or other combination partners are described in WO 2009/121945, the disclosure of which is incorporated herein in its entirety.

The methods of synthesis for the further DPP-4 inhibitors are described in the scientific literature and/or in published patent documents, particularly in those cited hereinbefore.

The active ingredients, in particular the DPP-4 inhibitor and/or the second and/or the third antidiabetic agent, may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The active ingredients or a pharmaceutically acceptable salt thereof may be present in the form of a solvate such as a hydrate or alcohol adduct.

As different metabolic functional disorders often occur simultaneously, it is quite often indicated to combine a number of different active principles with one another. Thus, depending on the functional disorders diagnosed, improved treatment outcomes may be obtained if a DPP-4 inhibitor is combined with active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The DPP-4 inhibitors mentioned above—besides their use in mono-therapy—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as rivoglitazone, mitoglitazone, INT-131 or balaglitazone; PPAR-gamma antagonists; PPAR-gamma/alpha modulators such as tesaglitazar, muraglitazar, aleglitazar, indeglitazar and KRP297; PPAR-gamma/alpha/delta modulators such as e.g. lobeglitazone; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119, such as the GPR119 agonists 5-ethyl-2-{4-[4-(4-tetrazol-1-yl-phenoxymethyl)-thiazol-2-yl]-piperidin-1-yl}-pyrimidine or 5-[1-(3-isopropyl-[1,2,4]oxadiazol-5-yl)-piperidin-4-ylmethoxy]-2-(4-methanesulfonyl-phenyl)-pyridine; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin degludec, insulin tregopil, insulin zinc suspension and insulin glargin; Gastric inhibitory Peptide (GIP); amylin and amylin analogues (e.g. pramlintide or davalintide); GLP-1 and GLP-1 analogues such as Exendin-4, e.g. exenatide, exenatide LAR, liraglutide, taspoglutide, lixisenatide (AVE-0010), LY-2428757, dulaglutide (LY-2189265), semaglutide or albiglutide; SGLT2-inhibitors such as e.g. dapagliflozin, sergliflozin (KGT-1251), atigliflozin, canagliflozin, ipragliflozin or tofogliflozin; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976) or of serine/threonine kinases; glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors, such as e.g. dapagliflozin, sergliflozin, atigliflozin, canagliflozin or (1S)-1,5-anhydro-1-[3-(1-benzothiophen-2-ylmethyl)-4-fluorophenyl]-D-glucitol; KV 1.3 channel inhibitors; GPR40 modulators such as e.g. [(3S)-6-({2',6'-dimethyl-4'-[3-(methylsulfonyl)propoxy]biphenyl-3-yl}methoxy)-2,3-dihydro-1-benzofuran-3-yl]acetic acid; SCD-1 inhibitors; CCR-2 antagonists; dopamine receptor agonists (bromocriptine mesylate [Cycloset]); 4-(3-(2,6-dimethylbenzyloxy)phenyl)-4-oxobutanoic acid; sirtuin stimulants; and other DPP IV inhibitors.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

A dual combination of glibenclamide/metformin is usually given in doses from 1.25/250 once daily to 10/1000 mg twice daily. (typical dosage strengths are 1.25/250, 2.5/500 and 5/500 mg).

A dual combination of glipizide/metformin is usually given in doses from 2.5/250 to 10/1000 mg twice daily (typical dosage strengths are 2.5/250, 2.5/500 and 5/500 mg).

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily (typical dosage strengths are 4/1, 4/2, 4/4, 8/2 and 8/4 mg).

A dual combination of pioglitazone/glimepiride is usually given in doses from 30/2 to 30/4 mg once daily (typical dosage strengths are 30/4 and 45/4 mg).

A dual combination of rosiglitazone/metformin is usually given in doses from 1/500 to 4/1000 mg twice daily (typical dosage strengths are 1/500, 2/500, 4/500, 2/1000 and 4/1000 mg).

A dual combination of pioglitazone/metformin is usually given in doses from 15/500 once or twice daily to 15/850 mg thrice daily (typical dosage strengths are 15/500 and 15/850 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Acarbose is usually given in doses from 25 to 100 mg with meals. Miglitol is usually given in doses from 25 to 100 mg with meals.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib); LDL receptor modulators; MTP inhibitors (e.g. lomitapide); and ApoB100 antisense RNA.

A dosage of atorvastatin is usually from 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan, azilsartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme (cetilistat); dexfenfluramine; axokine; cannabinoid receptor 1 antagonists such as the CB1 antagonist rimonobant; MCH-1 receptor antagonists; MC4 receptor agonists; NPY5 as well as NPY2 antagonists (e.g. velneperit); beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/metreleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Example 1: BI 1356, a Potent and Selective DPP-4 Inhibitor, is Safe and Efficacious in Patients with Inadequately Controlled Type 2 Diabetes Despite Metformin Therapy Efficacy and safety of BI 1356 (1, 5, or 10 mg qd), a potent and selective dipeptidyl peptidase-4 (DPP-4) inhibitor, was examined in inadequately controlled, metformin-treated (MET, ≥1 g daily) type 2 diabetic patients (T2DM; HbA1c at baseline 7.5-10.0%). Effects were compared to add-on of placebo (PBO) or of open label glimepiride (GLIM; 1 to 3 mg qd) in a 12-week randomized, double-blind study. Antidiabetic medication other than metformin was washed out for 6 weeks (34.7% of the patients).

The primary endpoint was change from baseline in HbA1c, adjusted for prior antidiabetic medication. 333 patients (mean baseline HbA1c 8.3%; fasting plasma glucose [FPG] 185 mg/dL) were randomized to BI 1356, PBO or open-label GLIM. After 12 weeks, BI 1356 treatment resulted in significant placebo corrected mean reductions in HbA1c (BI 1356 1 mg, n=65, −0.39%; 5 mg, n=66, −0.75%; 10 mg, n=66, −0.73%). Patients receiving GLIM demonstrated a slightly greater mean PBO corrected reduction in HbA1c at Week 12 (n=64, −0.90%). Reductions in FPG from baseline to Week 12 with BI 1356 were statistically significant (1 mg, −19 mg/dL; 5 mg, −35 mg/dL; 10 mg, −30 mg/dL). Hence, a dose-response relationship was demonstrated for HbA1c and FPG, reaching an effect plateau at 5 mg of BI 1356. For this dose, >80% DPP-4 inhibition at trough in >80% of the patients at week 12 was achieved.

In total, 106 patients (43.1%) experienced adverse events (AEs) with similar incidences across all treatments. Most frequently reported episodes were nasopharyngitis (7.5%), diarrhoea (3.3%), and nausea (3.0%). Drug-related hypoglycaemia did not occur with BI 1356 or PBO but in 3 patients receiving GLIM. Ten patients (3.7%) experienced serious AEs but none of these events were considered drug-related.

The addition of BI 1356 to MET in patients with T2DM inadequately controlled on MET alone achieved clinically relevant and statistically significant reductions in HbA1c. Combination treatment with BI 1356 1, 5, and 10 mg and MET was well tolerated and no case of hypoglycaemia was reported. The incidence of AEs was comparable with BI 1356 and PBO.

Example 2

The usability of a DPP-4 inhibitor or combination according to this invention for the purpose of the present invention (e.g. the beneficial effect on glycemic control) can be tested using clinical trials.

For example, in a randomised, double-blind, placebo-controlled, parallel group trial, the safety and efficacy of a DPP-4 inhibitor according to the invention (e.g. 5 mg of linagliptin administered orally once daily) is tested in patients with type 2 diabetes with insufficient glycemic control (HbA1c from 7.0% to 10% or from 7.5% to 10% or from 7.5% to 11%) despite a therapy with one or two conventional antihyperglycemic agents, e.g. selected from metformin, thiazolidindiones (e.g. pioglitazone), sulfonylureas, glinides, inhibitors of alpha-glucosidase, GLP-1 or GLP-1 analogues, and insulin or insulin analogues.

In the study with the sulphonylurea drug the efficacy and safety of a DPP-4 inhibitor according to this invention versus placebo added to a background therapy of a sulphonylurea is investigated (2 week placebo run-in phase; 18 weeks double-blind treatment followed by 1 week follow up after study medication termination; background therapy with a sulphonylurea drug is administered throughout the entire trial duration, including placebo run-in phase, in an unchanged dosage).

The success of the treatment is tested by determining the HbA1c value, by comparison with the initial value and/or with the value of the placebo group. A significant change in the HbA1c value compared with the initial value and/or the placebo value demonstrates the efficacy of the DPP-4 inhibitor for the treatment. The success of the treatment can be also tested by determining the fasting plasma glucose values, by comparison with the initial values and/or with the values of the placebo group. A significant drop in the fasting glucose levels demonstrates the efficacy of the treatment. Also, the occurrence of a treat to target response (i.e. an HbA1c under treatment <7%) demonstrates the efficacy of the treatment.

The safety and tolerability of the treatment is investigated by assessing patient's condition and relevant changes from baseline, e.g. incidence and intensity of adverse events (such as e.g. hypoglycaemic episodes or the like) or weight gain.

Example 3: Treatment of Pre-Diabetes

The efficacy of a pharmaceutical composition or combination according to the invention in the treatment of pre-diabetes characterised by pathological fasting glucose and/or impaired glucose tolerance can be tested using clinical studies. In studies over a shorter period (e.g. 2-4 weeks) the success of the treatment is examined by determining the fasting glucose values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose levels demonstrates the efficacy of the treatment. In studies over a longer period (12 weeks or more) the success of the treatment is tested by determining the HbA1c value, by comparison with the initial value and/or with the value of the placebo group. A significant change in the HbA1c value compared with the initial value and/or the placebo value demonstrates the efficacy of the DPP-4 inhibitors or combinations according to the present invention for treating pre-diabetes.

Example 4: Preventing Manifest Type 2 Diabetes

Treating patients with pathological fasting glucose and/or impaired glucose tolerance (pre-diabetes) is also in pursuit of the goal of preventing the transition to manifest type 2 diabetes. The efficacy of a treatment can be investigated in a comparative clinical study in which pre-diabetes patients are treated over a lengthy period (e.g. 1-5 years) with either a pharmaceutical composition or combination according to this invention or with placebo or with a non-drug therapy or other medicaments. During and at the end of the therapy, by determining the fasting glucose and/or a loading test (e.g. oGTT), a check is made to determine how many patients exhibit manifest type 2 diabetes, i.e. a fasting glucose level of >125 mg/dl and/or a 2 h value according to oGTT of >199 mg/dl. A significant reduction in the number of patients who exhibit manifest type 2 diabetes when treated with a DPP-4 inhibitor or combination according to the present invention as compared to one of the other forms of treatment, demonstrates the efficacy in preventing a transition from pre-diabetes to manifest diabetes.

Example 5: Treatment of Type 2 Diabetes

Treating patients with type 2 diabetes with the pharmaceutical composition or combination according to the invention, in addition to producing an acute improvement in the glucose metabolic situation, prevents a deterioration in the metabolic situation in the long term. This can be observed is patients are treated for a longer period, e.g. 3 months to 1 year or even 1 to 6 years, with the pharmaceutical composition or combination according to the invention and are compared with patients who have been treated with other antidiabetic medicaments. There is evidence of therapeutic success compared with patients treated with other antidiabetic medicaments if no or only a slight increase in the fasting glucose and/or HbA1c value is observed. Further evidence of therapeutic success is obtained if a significantly smaller percentage of the patients treated with a pharmaceutical composition or combination according to the invention, compared with patients who have been treated with other medicaments, undergo a deterioration in the glucose metabolic position (e.g. an increase in the HbA1c value to >6.5% or >7%) to the point where treatment with an additional oral antidiabetic medicament or with insulin or with an insulin analogue is indicated.

Example 6: Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of a DPP-4 inhibitor, pharmaceutical composition or combination according to the present invention according to the invention in the treatment of insulin resistance.

Example 7: Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of a DPP-4 inhibitor, pharmaceutical composition or combination according to the present invention according to the invention in the treatment of hyperglycaemia.

Example 8: Prevention of Micro- or Macrovascular Complications

The treatment of type 2 diabetes or pre-diabetes patients with a DPP-4 inhibitor, pharmaceutical composition or combination according to the invention prevents or reduces or reduces the risk of developing microvascular complications (e.g. diabetic neuropathy, diabetic retinopathy, diabetic nephropathy, diabetic foot, diabetic ulcer) or macrovascular complications (e.g. myocardial infarct, acute coronary syndrome, unstable angina pectoris, stable angina pectoris, stroke, peripheral arterial occlusive disease, cardiomyopathy, heart failure, heart rhythm disorders, vascular restenosis). Type 2 diabetes or patients with pre-diabetes are treated long-term, e.g. for 1-6 years, with a pharmaceutical composition or combination according to the invention and compared with patients who have been treated with other antidiabetic medicaments or with placebo. Evidence of the therapeutic success compared with patients who have been treated with other antidiabetic medicaments or with placebo can be found in the smaller number of single or multiple complications. In the case of macrovascular events, diabetic foot and/or diabetic ulcer, the numbers are counted by anamnesis and various test methods. In the case of diabetic retinopathy the success of the treatment is determined by computer-controlled illumination and evaluation of the background to the eye or other ophthalmic methods. In the case of diabetic neuropathy, in addition to anamnesis and clinical examination, the nerve conduction rate can be measured using a calibrated tuning fork, for example. With regard to diabetic nephropathy the following parameters may be investigated before the start, during and at the end of the study: secretion of albumin, creatinine clearance, serum creatinin values, time taken for the serum creatinine values to double, time taken until dialysis becomes necessary.

Example 9: Treatment of Metabolic Syndrome

The efficacy of a DPP-4 inhibitor, pharmaceutical composition or combination according to the present invention according to the invention can be tested in clinical studies with varying run times (e.g. 12 weeks to 6 years) by determining the fasting glucose or non-fasting glucose (e.g. after a meal or a loading test with oGTT or a defined meal) or the HbA1c value. A significant fall in these glucose values or HbA1c values during or at the end of the study, compared with the initial value or compared with a placebo group, or a group given a different therapy, proves the efficacy of an active substance or combination of active substances in the treatment of Metabolic Syndrome. Examples of this are a reduction in systolic and/or diastolic blood pressure, a lowering of the plasma triglycerides, a reduction in total or LDL cholesterol, an increase in HDL cholesterol or a reduction in weight, either compared with the starting value at the beginning of the study or in comparison with a group of patients treated with placebo or a different therapy.

Example 10: Therapeutic Response to DPP-4 Inhibitor Treatment

Genomic DNA samples from individual patients enrolled in a clinical trial (e.g. a clinical study as described herein) for a DPP-4 inhibitor (e.g. linagliptin, e.g. in a daily oral amount of 5 mg, optionally in combination with one or more other antidiabetic agents) are obtained and genotyped for variation(s) (e.g. polymorphisms) in one or more candidate genes selected from TCF7L2, KCNJ11, PPARG and GLP1R, particularly for a TCF7L2 risk genotype as described herein, and evaluated relative to each patients response in the clinical trial (cf., e.g., Example 21). The association between the likelihood (e.g., increased, decreased, or no likelihood) of a favorable DPP-4 inhibitor therapy response (e.g. favorable change in HbA1c value) and genetic variations (e.g. TCF7L2 risk genotypes) or references can be investigated by applying statistical analysis to the results of genotyping.

The probability of the likelihood of a favorable response of an individual resulting from treating said individual with the DPP-4 inhibitor may be thus determined by such genotyping a nucleic acid sample of the individual, for example by detecting one or more single nucleotide polymorphisms within the TCF7L2 gene, for example one SNP selected from rs7903146, rs12255372 and rs10885406, or by detecting the respective wild-type genotype (cf., e.g., Example 21).

Methods for genotyping, i.e. determining genetic variations (e.g. polymorphisms, particularly those described herein) from patients' nucleic acid samples are known in the art. For example, molecular genetic methods to detect single nucleotide polymorphisms, e.g. within the TCF7L2 gene, may be based on genetic sequencing, microarray or PCR analysis.

Example 11: Linagliptin Monotherapy Improves Glycemic Control and Measures of β-Cell Function in Type 2 Diabetes In a multi-center, 24 week, randomized, double-blind, placebo-controlled, parallel group study, the effects of linagliptin (LI) monotherapy (5 mg qd) are compared with placebo (PBO) in drug naïve or previously treated patients (pts) with type 2 diabetes mellitus (T2DM) (baseline HbA1c 4.9-10.6%). Randomization to LI (n=336) or PBO (n=167) follows a 2-week PBO run-in (previously treated pts go without medication for 4 wks prior to this). Mean baseline demographics (HbA1c, 8.0% [SD 0.87]; fasting plasma glucose (FPG), 166.0 mg/dL [41.1]; body mass index (BMI), 29.05 kg/m2 [4.81]; age, 55.7 yrs [10.2]) are similar in both groups. The primary endpoint is the change from baseline in HbA1c after 24 wks of treatment. LI shows a PBO-adjusted change in HbA1c from baseline of −0.69% (p<0.0001) with a continuous HbA1c reduction over time of −0.46% at 6 weeks to −0.69% at 24 weeks (both p<0.0001). LI patients are >4-fold more likely to achieve a reduction in HbA1c of ≥0.5% at 24 weeks than PBO (47.1% vs 19.0%; p<0.0001). For patients with baseline HbA1c ≥7.0% a significant greater number of LI-treated compared to PBO-treated patients achieve a target reduction of HbA1c to <7.0% at 24 weeks (25.2% vs. 11.6%; odds ratio of 2.9, p=0.0006). Patients with baseline HbA1c levels of ≥9.0% show the greatest reduction in HbA1c (−0.86%) from baseline. FPG improves by −23.3 mg/dL (p<0.0001) vs. PBO. In a meal tolerance test, the LI patients show a greater reduction in the adjusted mean change from baseline at week 24 for 2-hr postprandial glucose (PPG) (−58.4 mg/dL; p<0.0001) vs. PBO. LI improves insulin secretion (p<0.05), as shown by changes in HOMA-% B index (LI, 5.02 vs PBO, −17.2 [(mU/L)/(mmol/L)]), proinsulin/insulin ratio (LI, −0.015 vs PBO, 0.024) and the disposition index (LI, 3.05 vs PBO, −0.68). The proportion of patients reporting at least one adverse event (AE) is similar for both groups (52.4% LI; 58.7% PBO). Hypoglycemia is rare, occurring in 1 patients in each of the groups. Serious AEs are reported in both groups (LI, 3.0%; PBO, 4.2%) but are not considered drug-related. Linagliptin trough levels in patients with mild and moderate renal impairment are comparable to patients with normal renal function.

Conclusion: Linagliptin monotherapy shows a significant, clinically meaningful and sustained improvement in glycemic control reflected in changes in FPG and HbA1c, and accompanied by β-cell function improvements. Linagliptin is safe and well tolerated with no clinically significant changes in body weight or waist circumference. Linagliptin trough levels in patients with mild and moderate renal impairment are comparable to patients with normal renal function, supporting that no dose adjustment is required in renally impaired patients.

Example 12: Efficacy and Safety of Linagliptin in Type 2 Diabetes Inadequately Controlled on Metformin Monotherapy A multi-center, 24-week, randomized, placebo-controlled, double-blind, parallel group study examines the efficacy and safety of linagliptin (LI) administered as add-on therapy to metformin (MET) in type 2 diabetes mellitus (T2DM) hyperglycemic patients with insufficient glycemic control (HbA1c≥7 to ≤10.0% for patients previously treated only with metformin, or ≥6.5 to ≤9.0% for patients previously treated with additional oral antihyperglycemic drugs). Subjects who enter the screening period discontinue previous antidiabetic medication other than MET (≥1500 mg/day) for 6 weeks (including a placebo (PBO) run-in period during the last 2 weeks) prior to randomization to LI (n=524) or PBO (n=177). Mean baseline characteristics and demographics (HbA1c, 8.1%; fasting plasma glucose [FPG], 168.8 mg/dL; age, 56.5 yrs; BMI, 29.9 kg/m2) are similar between groups. The primary endpoint is the change from baseline HbA1c after 24 weeks of treatment, evaluated with an analysis of covariance (ANCOVA) adjusted for baseline HbA1c and prior antidiabetic medication. After 24 weeks of treatment, the adjusted mean treatment difference between LI+MET and PBO+MET is −0.64% (p<0.0001) in favor of LI+MET for change in HbA1c (%). Patients with a baseline HbA1c of ≥7.0% who receive LI+MET are more likely to achieve an HbA1c ≤7.0% relative to those receiving placebo+MET (26.2% vs. 9.2%, respectively; odds ratio, 4.4; p=0.0001). At week 24 LI+MET is superior to PBO+MET in reducing the mean fasting plasma glucose (FPG) from baseline (−21.1 mg/dL; p<0.0001). At study-end, 2 hr postprandial glucose (PPG) analyzed in meal tolerance tests shows a significantly greater (p<0.0001) mean reduction from baseline for the LI+MET treated (−67.1 mg/dL) versus the PBO+MET group. The proportion of patients reporting at least one adverse event (AE) is comparable within the LI+MET and PBO+MET groups (52.8% and 55.4%, respectively). Hypoglycemia is rare, occurring in 5 PBO+MET patients (2.8%) and 3 LI+MET patients (0.6%), all episodes being of mild intensity. The change in the body weight from baseline to 24 weeks is similar between the 2 treatment groups (−0.5 kg PBO+MET; −0.4 kg LI+MET). Conclusion, linagliptin 5 mg qd as add-on therapy in patients with T2DM inadequately controlled on metformin is well tolerated and produces significant and clinically meaningful improvements in glycemic control (reductions in HbA1c, FPG and 2 h PPG without weight gain). Linagliptin as add-on therapy to metformin in patients with T2DM and insufficient glycemic control is well tolerated with the incidence of adverse events comparable to placebo.

Example 13: Linagliptin Improves Glycemic Control in Type 2 Diabetes Patients Inadequately Controlled by Metformin and Sulfonylurea without Weight Gain or Hypoglycemia A multi-center, 24-week, randomized, double-blind, placebo-controlled, parallel group study examines the efficacy and safety of the DPP-4 inhibitor linagliptin (LI; 5 mg qd) in type 2 diabetes (T2DM) patients (pts) with insufficient glycemic control (HbA1c 7.0-10.0%) on the combination of metformin (MET) plus a sulfonylurea (SU). Effects of LI as add-on are compared with placebo (PBO). All pts have a 2-wk PBO run-in before being randomized to LI+MET+SU (n=793) or PBO+MET+SU (n=265). Mean baseline characteristics are: HbA1c, 8.14% (SD 0.8); fasting plasma glucose (FPG), 160.1 mg/dL (36.6); age, 58.1 yrs (9.8); BMI, 28.3 kg/m2 (4.7). Most of the pts (73.3%) have T2DM for >5 years before enrollment. The primary endpoint is the change from baseline in HbA1c after 24 weeks of treatment, adjusted for baseline HbA1c. After 24 weeks of treatment, the mean HbA1c for LI+MET+SU is −0.62% lower (p<0.0001) relative to PBO+MET+SU. The maximum mean HbA1c reduction with LI+MET+SU is seen at week 12 (−0.84%). Patients with baseline HbA1c ≥7.0% are >5-fold more likely to achieve a target HbA1c of <7.0% when treated with LI+MET+SU (29.2%) compared with PBO+MET+SU (8.1%, odds ratio 5.5, p<0.0001) at 24 weeks. For the change in FPG, a statistically significant (p<0.0001) adjusted mean difference of −12.7 mg/dL is observed between Li+MET+SU and BPBO+MET+SU from baseline at week 24. Measures relating to β-cell function (fasting plasma insulin and HOMA-% B) along with HOMA-IR are significantly (p≤0.05) improved with LI+MET+SU compared with PBO+MET+SU. The proportion of patients that reported a severe adverse event (AE) is low for both LI+MET+SU and PBO+MET+SU groups (2.4% vs. 1.5%, respectively). The most frequent AE reported more commonly in the LI+MET+SU group than in the PBO+MET+SU group is hypoglycemia (22.7% vs. 14.8%, respectively). This is expected due to the combination with SU. No significant changes in weight are noted for either treatment group. Conclusion: Therapy with linagliptin added to the combination of metformin and a sulfonylurea is efficacious and safe in producing significant and clinically meaningful improvements in glycemic control in T2DM patients. Linagliptin may provide an additional option prior to insulin therapy in many patients for whom glycemia is insufficiently controlled with metformin plus a sulfonylurea agent. Linagliptin is shown to have a favorable safety and tolerablility profile. However, when linagliptin is added on pre-existing sulfonylurea therapy, hypoglycemia may occur.

Example 14: Efficacy and Safety of Initial Combination Therapy with Linagliptin and Pioglitazone in Patients with Inadequately Controlled Type 2 Diabetes A multi-center, 24-week, randomized, double-blind, placebo-controlled, parallel group study investigates the efficacy and safety of initial combination therapy with the DPP-4 inhibitor linagliptin (LI) and pioglitazone (PIO). Patients (pts) with type 2 diabetes mellitus (T2DM) and insufficient glycemic control (HbA1c 7.5-11.0%) who are drug naïve or previously treated with any oral antihyperglycemic drug (OAD), are randomized to receive 5 mg LI plus 30 mg PIO qd (n=259) or 30 mg PIO plus placebo (PBO) qd (n=130). Patients do not take any OAD for at least 6 weeks before randomization. Mean baseline characteristics (HbA1c 8.6%; fasting plasma glucose [FPG] 190 mg/dL; age 57.5 yrs; BMI 29.0 kg/m2) are similar between the groups. The primary endpoint is the change from baseline in HbA1c after 24 weeks of treatment, adjusted for baseline HbA1c and prior antidiabetic medication. After 24 weeks of treatment, the adjusted mean change in HbA1c for the patients in the LI+PIO group (full analysis set, last observation carried forward) is −1.06% (standard error (SE) ±0.06). The difference in the adjusted mean HbA1c for the LI+PIO group compared with PBO+PIO is −0.51% (p<0.0001; 95% confidence interval (CI), −0.71, −0.30). Reductions in FPG are also significantly greater for the LI+PIO group compared with PBO+PIO with a treatment difference of −14.2 mg/dL (p<0.0001; 95% confidence interval (CI), −21.1, −7.3) at 24 weeks. Patients in the LI+PIO group are more likely to achieve a target HbA1c of <7% vs. those on PBO+PIO (42.9% vs. 30.5%, respectively, odds ratio 2.1; p=0.0051), as well as a reduction in HbA1c of ≥0.5% (75% vs. 50.8%, respectively, odds ratio 3.8; p<0.001). The proportion of patients that experienced at least one adverse event (AE) is similar for both LI+PIO and PBO+PIO groups (136, 52.5% vs. 53.1%, respectively). Hypoglycemia is rare, occurring in 3 patients (1.2%) in the LI+PIO group and none in the PBO+PIO group. All hypoglycemic events are of mild intensity.

Conclusion: Initial combination therapy with linagliptin and pioglitazone shows significant and clinically meaningful improvements in FPG and HbA1c levels compared with PIO alone, along with a greater improvement in beta-cell function. Co-administration of linagliptin with pioglitazone is shown to be safe and well tolerated. Combination therapy with linagliptin and pioglitazone may provide an important synergistic initial treatment option for T2DM patients with inadequate glycemic control or those with renal impairment for whom metformin is contraindicated.

Example 15: Linagliptin Monotherapy Improves Glycemic Control in Japanese Patients with Type 2 Diabetes Mellitus Over 12 Weeks A multi-center, 12-week, randomized, double-blind, placebo-controlled, parallel group study investigates the efficacy and safety of the DPP-4 inhibitor linagliptin (LI). Effects of LI monotherapy (5 mg qd and 10 mg qd) are compared to placebo (PBO) in drug naïve or previously treated Japanese patients (pts) with type 2 diabetes mellitus (T2DM) (baseline HbA1c 7.0-10.0%, if drug naïve; 7.0-9.0%, if previously treated). Before being randomized to LI 5 (n=159) or 10 mg (n=160), or PBO (n=80), all patients have a 2-week PBO run-in (patients on an oral antihyperglycemic drug have no medication for 2 weeks prior to run-in). Mean [SD] baseline characteristics and demographics (HbA1c, 8.0% [0.68]; fasting plasma glucose (FPG), 163.5 mg/dL [32.4]; BMI, 24.97 kg/m2 [3.86]; age, 60.0 yrs [9.7]) are similar in all groups. The primary endpoint is the change from baseline in HbA1c after 12 weeks. The differences of adjusted mean changes from baseline in HbA1c at week 12 are −0.87% for LI 5 mg vs. PBO (p<0.0001) and −0.88% for LI 10 mg vs. PBO (p<0.0001). Proportions of patients achieving HbA1c<7.0% after 12 wks are 26.4% for LI 5 mg and 35.7% for LI 10 mg vs. 10.0% for PBO. Proportions of patients whose HbA1c levels lower by at least 0.5% are 57.2% with LI 5 mg, 59.9% with LI 10 mg, and 8.8% with PBO. Both LI 5 mg and 10 mg show statistically significant difference compared with PBO (p<0.0001). FPG is significantly improved with both LI 5 and 10 mg compared to PBO: after 12 weeks, the differences of adjusted mean changes from baseline are −19.7 mg/dL for LI 5 mg vs. PBO (p<0.0001) and −20.4 mg/dL for LI 10 mg vs. PBO (p<0.0001). As indicated by changes in the proinsulin/insulin ratio (LI 5 mg, p=0.0065; LI 10 mg, p=0.0004), LI also significantly improves insulin secretion. The proportion of patients experiencing at least one adverse event (AE) is comparable among the three groups (56.0% LI 5 mg, 53.1% LI 10 mg and 56.3% PBO). Of those; 9.4%, 8.8% and 10.0%, respectively, are assessed as being drug-related. There are no investigator-defined hypoglycemic episodes. Body weight is unchanged with both LI 5 mg and 10 mg, −0.39 and −0.06 kg, respectively, which is not significantly different vs. PBO (−0.04 kg).

Conclusion: Linagliptin demonstrates a significant and clinically meaningful improvement in glycemic control, reflected in changes in HbA1c and FPG in Japanese patients with T2DM. Both linagliptin 5 and 10 mg doses have similar efficacy in lowering HbA1c and are well tolerated within this population. 5 mg linagliptin is the therapeutic dose in Japanese patients, which is identical to the therapeutic dose in Caucasians.

Example 16: Linagliptin Provides Superior Glycemic Control Compared to Voglibose as Monotherapy in Japanese Patients with Type 2 Diabetes A multi-center, 26-week, randomized, double-blind, active-controlled, parallel group Study compares the efficacy and safety of the DPP-4 inhibitor linagliptin (LI) vs. the α-glucosidase inhibitor voglibose (VB) in drug naïve or previously treated Japanese patients (pts) with Type 2 diabetes mellitus (T2DM) (baseline HbA1c 7.0-10.0% if drug naïve, 7.0-9.0% if previously treated with an oral antihyperglycemic drug (OAD)).

Following a 2-week PBO run-in, patients are randomized to LI 5 (n=159) or 10 mg qd (n=160), or VB (0.2 mg tid; n=162). Any previous OAD treatment is stopped 2 weeks prior to run-in. Mean baseline [SD] characteristics and demographics (HbA1c, 8.01% [0.68]; fasting plasma glucose (FPG), 163.5 mg/dL [32.4]; BMI, 24.97 kg/m2 [3.86]; age, 60.0 yrs [9.7]) are similar across groups. The primary endpoint is the change from baseline in HbA1c after 26 weeks. The differences of adjusted mean changes from baseline in HbA1c at week 26 are −0.32% for LI 5 mg vs. VB (p=0.0003) and −0.39% for LI 10 mg vs. VB (p<0.0001). Proportions of patients achieving HbA1c<7.0% after 26 weeks are 30.2% for LI 5 mg and 34.4% for LI 10 mg vs. 22.2% for VB. Proportions of patients whose HbA1c level lowered by ≥0.5% are 57.2% and 53.5% for LI 5 and 10 mg, vs. 37.7% for VB. FPG is significantly improved with both LI 5 and 10 mg compared to VB: the differences of adjusted mean changes from baseline are −6.9 mg/dL for LI 5 mg vs. VB (p=0.02) and −9.8 mg/dL for LI 10 mg vs. VB (p=0.0015). Both LI 5 mg and 10 mg show a significant decrease of HbA1c in patients previously treated with 1 OAD compared with VB (p=0.003 and p=0.0011, respectively). The occurrence of ≥1 adverse event (AE) is comparable between groups (72.3% LI 5 mg, 77.5% LI 10 mg and 71.6% VB). Of the AEs, 11.3%, 10.6% and 18.5%, respectively, are assessed as drug related. Drug-related gastrointestinal disorders are more common in the VB (14.2%) than LI (8.2% 5 mg; 8.1% 10 mg) groups. In the VB group, 1 hypoglycemic episode is reported vs. none in the LI groups.

Conclusion: Linagliptin monotherapy demonstrates greater efficacy than VB for improving glycemic control in Japanese patients with T2DM. Both linagliptin 5 mg and linagliptin 10 mg have comparable efficacy and show statistically significant decreases in HbA1c and FPG from baseline compared with VB after 26 weeks. Linagliptin is well tolerated in Japanese patients with T2DM compared to VB, with less gastrointestinal AEs, and may provide a valuable addition to the therapies available to this population. 5 mg linagliptin is the therapeutic dose in Japanese patients, which is identical to the therapeutic dose in Caucasians.

Example 17: Linagliptin Restores β-Cell Function and Survival in Human Isolated Islets Studies in diabetic animal models show that dipeptidyl peptidase-4 (DPP-4) inhibitors reverse hyperglycemia and increase β-cell mass. Here, the role of linagliptin, a DPP-4 inhibitor on human β-cell function is investigated: Human isolated islets are exposed to increased glucose concentrations (5.5-33.3 mM), 0.5 mM palmitic acid, the mixture of 2 ng/mL IL-1β or 1,000 U/mL IFN-γ for 4 days or 50 µM H2O2 for 8 h. Islets are pre-treated with 500 ng/mL Interleukin-1 Receptor Antagonist (IL-1 Ra, which has been shown to restore β-cell function), 100 nM linagliptin or solvent for 1 h before exposure to the diabetic stimuli and during the whole 4-day treatment period. At control conditions, islets secrete 3.8-fold more insulin at 16.7 mM than at 2.8 mM glucose. In contrast, stimulatory index is 1.9- and 2.4-fold decreased when islets are exposed to 11.1 mM and 33.3 mM glucose (P<0.05). Exposure of the islets to palmitate, cytokine mixture or H2O2 results in a 2.1-, 2.2- and 1.9-fold reduction of glucose stimulated insulin secretion (GSIS), respectively (P<0.05). Linagliptin significantly restores β-cell function at all conditions (1.9-, 2.5-, 3.3-, 1.9- and 3.7-fold increase in GSIS at 11.1 or 33.3 mM glucose, palmitic acid, cytokines or H2O2, P<0.05). IL-1 Ra is similarly effective in restoring β-cell function at conditions of high glucose, palmitic acid and cytokines, but IL-1 Ra fails to restore β-cell function at oxidative stress conditions induced by H2O2 treatment. Since loss of function is mediated by oxidative stress, the nitrotyrosine concentration is measured in islet lysates. Nitrotyrosine levels are highly elevated in human islets under all diabetic conditions (13-, 14-, 6-, 14- and 8-fold increased at 11.1 or 33.3 mM glucose, palmitic acid, cytokines or H2O2, P<0.05), while no elevated nitrotyrosine production is observed in islets treated with linagliptin.

In summary, it is shown that the DPP-4 inhibitor linagliptin has comparable protective effects on gluco-, lipo- and cytokinetoxicity as IL-1 Ra and, in addition, could improve β-cell function under oxidative stress conditions and blocks apoptosis (induced by H2O2 treatment). The study provides evidence of a direct protective effect of linagliptin on β-cell survival and insulin secretion.

Example 18: Chronic Renal Disease does not Change the Pharmacokinetics of Linagliptin but Increases Exposure of Sitagliptin and Alogliptin in Rats Renal impairment is a frequent complication of T2DM. The effect of chronic renal disease on the pharmacokinetics of dipeptidyl peptidase-4 inhibitors (linagliptin, sitagliptin, alogliptin) in a rat model of chronic renal insufficiency (5/6 nephrectomy, 5/6N) is investigated: Eight weeks after surgery rats are treated orally with inhibitors for 4 days. 5/6N causes a highly significantly (P<0.001) decrease of glomerular filtration rate measured by creatinin clearance (sham: 2510±210 mL/24 h; 5/6N: 1665±104.3 mL/24 h) and increases cystatin C levels (sham: 700±35.7 ng/mL; 5/6N: 1434±77.6 ng/mL). Tubular function is significantly (P<0.001) impaired as evidenced by plasma neutrophil gelatinase-associated lipocalin (NGAL), (sham: 286±23 ng/ml; 5/6N: 680±56.3 ng/ml) and β2 microglobulin (sham: 20.4±2.4 µg/mL; 5/6N: 33.3±1.34 µg/mL). DPP-4 activity is comparable among groups.

Administration of linagliptin (0.5 and 7 µmol/kg) to 5/6N rats shows no significant change in AUC(0-∞): sham: 316±54.7 nmol*h/L; 5/6N: 257±21.54 nmol*h/L; P=0.771 and sham: 1252±372 nmol*h/L; 5/6N: 748±74.5 nmol*h/L; P=0.284, respectively. In contrast, both sitagliptin and alogliptin (7 µmol/kg) have significantly (P=0.0001 and P=0.039) higher (41% and 28%) AUC(0-∞): sitagliptin sham: 3690±103 nmol*h/L; 5/6N: 6238±423 nmol*h/L and alogliptin sham: 1772±225 nmol*h/L; 5/6N: 2445±166 nmol*h/L). Furthermore, no correlation of markers of tubular and glomerular functions with linagliptin AUC is observed. In contrast, sitagliptin significantly correlate with creatinin clearance (r2=0.374, P<0.05), cystatin C (r2=0.499, P<0.01), NGAL (r2=0.604, P<0.01) and β2 microglobulin (r2=0.543, P<0.01). Alogliptin correlates less significantly with cystatin C (r2=0.376, P<0.05) and β2 microglobulin (r2=0.391, P<0.05) but not with creatinin clearance and NGAL.

These results demonstrate that renal impairment does not affect the pharmacokinetics of linagliptin whereas it increases the exposure of sitagliptin and alogliptin. Therefore, in contrast to sitagliptin and alogliptin, linagliptin may not have to be dose-adjusted in patients with T2DM and renal impairment or diabetic nephropathy.

Further, linagliptin significantly inhibits mRNA expression of profibrotic factors, such as TGF-β1, T1MP-1 and collagen (Col3alpha1) in the heart of uremic rats, which factors are tissue fibrosis markers of cardiac fibrosis and are increased in uremic heart. Characteristic cardiomyopathy with intestinal expansion and fibrosis develops often in uremia. Thus, these antifibrotic properties of DPP-4 inhibitors may be used for the treatment of cardiac and renal injury, uremic heart, cardiac fibrosis and/or cardiomyopathy with intestinal expansion and fibrosis associated with uremia in patients with type 2 diabetes. The antifibrotic action of linagliptin can be an additional benefit for patients with chronic kidney and/or heart diseases that often accompany type 2 diabetes.

Example 19: Linagliptin Improves Hepatic Steatosis in Rodent Models

Hepatic steatosis is a hallmark of patients with Type 2 diabetes and non-alcoholic fatty liver disease (NAFLD). Linagliptin is a selective and non-renal excreted inhibitor of dipeptidyl peptidase-4 (DPP-4).

In a model of diet-induced obesity (D10, fed for 2 and 3 months), the effect of 4 weeks therapy with linagliptin (3 and 30 mg/kg/day, n=10) is investigated. Liver lipid content is detected by magnetic resonance spectroscopy (MRS) in vivo and by analysis of liver triglycerides ex vivo. Linagliptin inhibits DPP-4 activity significantly (P<0.001) by 67% to 80% and 79% to 89% (3 and 30 mg/kg/day, respectively)

compared to controls. Blood glucose levels following an OGTT (AUC) are significantly (P<0.01) decreased ranging from 16% to 20% (3 mg/kg/day) and 20% to 26% (30 mg/kg/day). Likewise, liver fat content (MRS detection) is significantly reduced. Changes in liver fat content are visible as early as 2 weeks on treatment. The correlation between liver lipid content as measured by MRS and hepatic triglyceride levels as measured ex vivo is r2=0.565 (P<0.0001). Furthermore, ob/ob mice are analyzed after 14 days of linagliptin treatment (3 mg/kg/day or control) and blinded histological scoring is performed (severity and grade of fat content, markers of inflammation). DPP-4 activity is inhibited by 80% and blood glucose AUC reduction is 25% (P<0.05). The histological score reveals less hepatic steatosis and inflammation in the linagliptin group (2.2±0.13, n=9, P<0.01) versus control (3±0.18, n=10).

In conclusion, linagliptin significantly reduces liver fat content and histological NAFLD in a high fat diet model. Linagliptin reverses liver triglyceride content and hepatic steatosis (with greater therapeutic impact when hepatic steatosis is more pronounced), The reversal of hepatic steatosis supports the use of linagliptin in patients with Type 2 diabetes as well as liver-associated diseases (NAFLD).

Example 20: Linagliptin Functionally Counteracts a Dysregulation in DPP-4 Expression in Diabetes-Impaired Wounds Impaired wound healing is a major complication of diabetes mellitus. The dipeptidyl peptidase-4 (DPP-4) inhibitor linagliptin improves wound healing (as shown in ob/ob mice). The impact of linagliptin on inflammatory markers in wounded skin is examined and a rationale for the beneficial action of linagliptin on wound healing is provided:

Wounds of linagliptin (3 mg/kg/day) and mock-treated ob/ob mice for the inflammatory markers COX-2 and MIP by RNase protection assays are investigated with no significant differences. Furthermore, linagliptin does not increase the number of apoptotic infiltrating F4/80-positive macrophages. Therefore, the expression of DPP-4 in the skin of diabetic and non-diabetic animals is assessed. Immunohistochemistry (IHC) and immunoblots reveal a strong expression of DPP-4 in skin from healthy and diabetic (ob/ob) mice and keratinocytes as the major cellular source of the enzyme. In line, the localization of DPP-4 protein in the skin nicely correlates with whole body autoradiography obtained after [3H]-labelled linagliptin treatment. Analyzing DPP-4 expression in mice upon full-thickness excisional wounding it is found that in healthy mice, DPP-4 protein expression declines over 3 days after injury and the enzyme remains absent in the late phase of repair. Interestingly, skin injury leads to a strong down-regulation of DPP-4 expression in proliferating wound margin keratinocytes (IHC). In contrast, in acute wounds of diabetic mice any DPP-4 expression can not be observed. DPP-4 protein, however, is expressed in the late phase of wound repair. The inverse regulation of DPP-4 protein in diabetic versus non-diabetic skin provides a functional basis of the positive action of linagliptin in wound healing processes. Thus, improvement of the wound healing process mediated by a suitable DPP-4 inhibitor, such as linagliptin, depends on the compensation (inhibition) of a dysregulated DPP-4 in diabetic wounds rather than on the anti-glycemic or immunomodulatory effects thereof. Thus, a DPP-4 inhibitor being suitable for improving wound healing is such a DPP-4 inhibitor which can effectively bind to DPP-4 in the skin, e.g. to dysregulated DPP-4 in diabetic wounds, preferably in its therapeutic dose level.

Furthermore in this context, a DPP-4 inhibitor being suitable for improving wound healing, particularly in a type 2 diabetes patient, is such a DPP-4 inhibitor which can be applied topically to wounds, e.g. comprised in wound dressings or patches or creams or ointments. Thus, the present invention further provides topical devices for wounds, such as e.g. wound dressings or patches, comprising linagliptin and, optionally, one or more pharmaceutically acceptable carriers and/or excipients.

Example 21: Association Study (Genotyping TCF7L2, Treatment Response)

The polymorphisms and variants of the gene TCF7L2 as depicted in the Table i can be analyzed as described in the following procedure:

TABLE i

Gene, variant nucleotides and rs numbers.

| Gene | variant nucleotide | rs number |
|---|---|---|
| TCF7L2 | c.382-41435 C > T | rs7903146 |
|  | c.483 + 9017 G > T, | rs12255372 |
|  | c.382-22060 A > G | rs10885406 |
|  | c.1102 C > G | rs731788 |

Samples

Patients' DNA samples (conc.: 50 ng/µl) in 96-well-plates are used for the analytical methods applied.

Genotyping by Direct Sanger Sequencing

Using gDNA as a template, locus specific DNA fragments are amplified by polymerase chain reaction (PCR).

PCR is carried out using an ABI BioRad® Tetrad PCR System. Quality of the PCR products is analyzed by agarose gel electrophoresis The purified PCR-products are used as templates in sequencing reactions According to the chain terminating methodology of Sanger et al. (1977), the analysis of DNA sequence is based on the termination of a growing DNA strand due to incorporation of a dye-labeled 2', 3'-Dideoxyribonucleotidetriphosphate (ddNTP) by the DNA polymerase. Purified sequencing products are analyzed using an ABI PRISM® 3730 Genetic Analyzer.

Sequencing data are generated using the original ABI Software. The subsequent KB-basecalling as well as the assembly is performed using the Staden Software Package. KB-basecalling assigns quality values to all called bases of automated sequencer traces using KB-basecaller error probabilities. These quality values are used during assembling the single reads and are the basic requirement for calculating the sequence accuracy (Applied Biosystems, 3730/3730xI/ DNA Analyzer Sequencing Analysis Software Training).

A quality value (q) of 20 corresponds to an error probability (ep) of 1/100, a value of 30 to an ep of 1/1000 and so on. In the assembly phase those values are set against each other. In general sequencing is continued until each consensus base has a quality value (q) of 50 or more. This corresponds to an error probability (ep) of 1/100000. Due to the fact that most of the consensus bases have an even higher quality score than the minimal one, the calculated cumulative error probability for the finished sequence is again significantly lower. Sequencing data are uploaded and analyzed using the software seqpatient from jsi-medical systems (version Seq Pilot 3.3.2, JSI medical systems GmbH. Friedhofstr. 5, 77971 Kippenheim, Germany).

Only traces that fulfill internal quality aspects are processed for further genotype analyses. Genotyping is carried out through the analysis of single polymorphisms rather than the analysis of the entire gene. Therefore genotyping results refer only to the variant positions depicted in Table i.

Genotyping by TaqMan PCR

The TaqMan® technology comprises amplification of a PCR fragment with simultaneous detection of the degradation of a labelled probe. Probes are labelled at both ends with an allele-specific dye and a quencher. During the amplification reaction, the specifically hybridized probe is displaced by the DNA polymerase. This displacement occurs either as degradation through the 5' exonuclease activity of the polymerase in the case of a perfect match with the probe, or without degradation in the case of a mismatch. Upon degradation, the quencher and dye are separated and the fluorescence signal increased. An increase in the fluorescence signal is indicative for the presence of the respective allele. Fluorescence signals are recorded with the ABI PRISM 7700 system (Applied Biosystems).

In detail, a master mix is prepared containing all components for PCR reaction and aliquoted in the appropriate number of wells. Subsequently, DNA is added to each well according to the plate layout; except for no-template control (NTC).

AB assay ID (rs7903146) C_29347861_10
SNP context sequence:

(SEQ ID NO: 1)
TAGAGAGCTAAGCACTTTTTAGATA[C/T]TATATAATTTAATTGCCGTA

TGAGG

The mastermix per sample contains:

| Nuclease-free water | 0.25 µl |
| 2x PCR MasterMix | 2.5 µl |
| 20x Primer/Probe Mix | 0.25 µl |
| DNA [10 ng/µl] | 2 µl |
| In total: | 5 µl |

The cycling conditions are:

| 95° C. | 10 min. | |
| 95° C. | 15 sec. | } 50 cycles |
| 60° C. | 90 sec. | |

The TaqMan® pre- and post-reads of the AD are performed on the TaqMan® 7900HT Fast Real System. The SDS software V2.3 calculates the fluorescence measurements made during the plate read and plots Rn values based on the signals from each well. Using the software, it is determined which SNP alleles are present in each sample. NTC should be given as not determined.

Statistical Analyses

To assess the homogeneity of the treatment effect on the change from baseline of HbA1c after 24 weeks in the genotype subgroups defined by TCF7L2 SNP rs7903146 genotypes an analysis of covariance (ANCOVA) model including the treatment interaction with the covariate genotype is applied for pooled data over four studies. The statistical model includes 'Treatment', 'Genotype', 'Study', Wash-Out-Period for prior oral antidiabetic drugs (yes/no)', 'Race', as well as the interaction term 'Treatment*Genotype' as fixed effects and 'HbA1c baseline' as a linear covariate. The ANCOVA model provides estimates for the mean change from baseline in HbA1c after 24 weeks of therapy for the different genotypes taking baseline clinical and demographic information into account.

Model based pair-wise comparisons between wild-type homozygous (genotype CC) and heterozygous (genotype CT) or rare homozygous (genotype TT) individuals on linagliptin or combination treatment (linagliptin+pioglitazone, linagliptin+metformin, linagliptin+metformin+a sulphonylurea) are performed.

Additionally the results of the corresponding ANCOVA models without 'Genotype' and 'Treatment*Genotype' fixed effects are given for the whole patient population of the studies (full analysis set, FAS) as well as for the subpopulation for which genetic analyses are performed (full analysis set for pharmacogenetic analyses, FASG) to demonstrate comparability of the observed effects.

The statistical evaluation is prepared using the software packages SAS Version 9.2 (SAS Institute Inc., Cary, N.C., USA) and S-PLUS® 8.0 (Insightful Corp., Seattle, Wash., USA).

FIG. 1 shows mean values and 95% confidence intervals for baseline HbA1c values for the whole patient population of the studies (full analysis set, FAS), for the subpopulation for which genetic analyses are performed (full analysis set for pharmacogenetic analyses, FASG), as well as for the subgroups defined by genotype (CC, CT, TT) of this subpopulation. The numbers of patients for placebo control and linagliptin treatment are given in braces.

Figure 2:
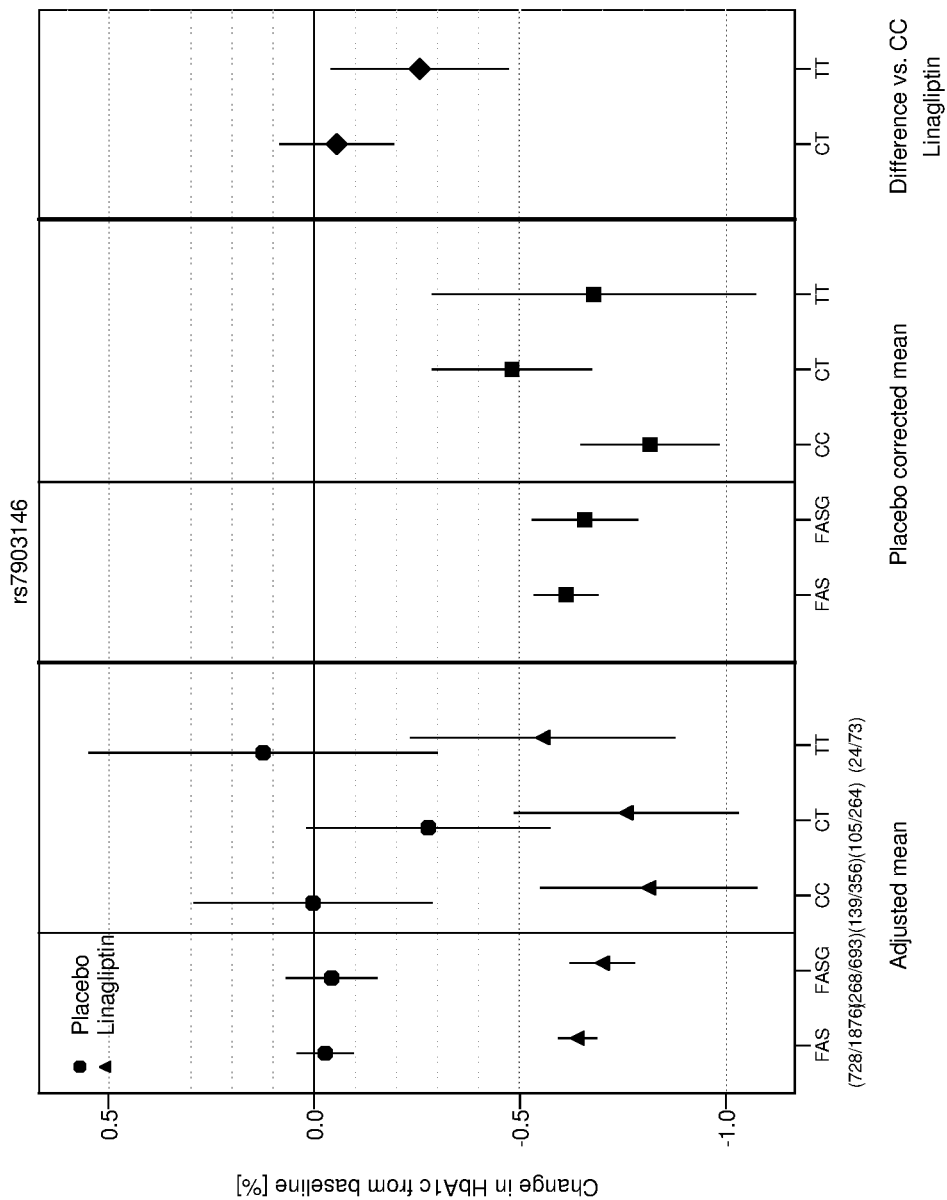
FIG. 2 shows the association of SNP rs7903146 in TCF7L2 with linagliptin response.

FIG. 2 shows a statistical association between TCF7L2 SNP rs7903146 genotypes with a likelihood of a favorable response in CC/CT genotype carriers to the administration of a therapeutically-effective amount of linagliptin or linagliptin in combination with other oral antidiabetic therapy.

Results are shown as point estimates and 95% confidence intervals for the mean change in HbA1c from baseline [%] after 24 weeks as estimated by ANCOVA models. The results are given for the whole patient population of the studies (full analysis set, FAS), for the subpopulation for which genetic analyses are performed (full analysis set for pharmacogenetic analyses, FASG), as well as for the subgroups defined by genotype (CC, CT, TT) of this subpopulation. The numbers of patients for placebo control and linagliptin treatment are given in braces.

Point estimates and 95% confidence intervals for the differences in changes in HbA1c from baseline [%] for the comparison of between wild-type homozygous (genotype CC) and heterozygous (genotype CT) or rare homozygous (genotype TT) individuals on linagliptin treatment or combination treatment (linagliptin+pioglitazone, linagliptin+metformin, linagliptin+metformin+a sulphonylurea) are shown as well. They result in a statistically significant difference between TT and CC (p value=0.0192). (Other pairwise comparisons: CT vs. CC: p=0.4359; CT vs. TT: p=0.0712).

This indicates a significant association between the wild-type homozygous genotype and lower HbA1c on treatment.

EXAMPLES OF FORMULATIONS

The following examples of formulations, which may be obtained analogously to methods known in the art, serve to illustrate the present invention more fully without restricting it to the contents of these examples. The term "active substance" denotes one or more compounds according to the invention, i.e. denotes a DPP-4 inhibitor or a second or third antidiabetic compound according to this invention or a combination of two or three of said active ingredients, for example selected from the combinations as listed in the Table 1 or 2. Additional suitable formulations for the DPP-4 inhibitor linagliptin may be those formulations disclosed in the application WO 2007/128724, the disclosure of which is incorporated herein in its entirety. Additional suitable formulations for the other DPP-4 inhibitors may be those formulations which are available on the market, or formulations described in the patent applications cited above in paragraph "background of the invention", or those described in the literature, for example as disclosed in current issues of "Rote Liste®" (Germany) or of "Physician's Desk Reference".

Example 1: Dry Ampoule Containing 75 mg of Active Substance Per 10 ml

Composition:

| Active substance | 75.0 mg |
|---|---|
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

Example 2: Dry Ampoule Containing 35 mg of Active Substance Per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

Example 3: Tablet Containing 50 mg of Active Substance

Composition:

| (1) Active substance | 50.0 mg |
|---|---|
| (2) Mannitol | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example 4: Tablet Containing 350 mg of Active Substance

Preparation:

| (1) Active substance | 350.0 mg |
|---|---|
| (2) Mannitol | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example 5: Capsules Containing 50 mg of Active Substance

Composition:

| (1) Active substance | 50.0 mg |
|---|---|
| (2) Dried maize starch | 58.0 mg |
| (3) Mannitol | 50.0 mg |
| (4) Magnesium stearate | 2.0 mg |
| | 160.0 mg |

Preparation:

(1) is triturated with (3). This trituration is added to the mixture of (2) and (4) with vigorous mixing. This powder mixture is packed into size 3 hard gelatin capsules in a capsule filling machine.

Example 6: Capsules Containing 350 mg of Active Substance

Composition:

| (1) Active substance | 350.0 mg |
|---|---|
| (2) Dried maize starch | 46.0 mg |
| (3) Mannitol | 30.0 mg |
| (4) Magnesium stearate | 4.0 mg |
| | 430.0 mg |

Preparation:

(1) is triturated with (3). This trituration is added to the mixture of (2) and (4) with vigorous mixing. This powder mixture is packed into size 0 hard gelatin capsules in a capsule filling machine.

The invention claimed is:

1. A method for treating type 2 diabetes mellitus in a patient in need thereof, wherein the patient has type 2 diabetes and has at least one T allele in the single nucleotide polymorphism (SNP) rs7903146 in the gene coding for TCF7L2, said method comprising testing whether the type 2 diabetes patient has at least one T allele in the single nucleotide polymorphism (SNP) rs7903146 in the gene coding for TCF7L2, and administering a DPP-4 inhibitor selected from linagliptin, sitagliptin, vildagliptin, alogliptin, saxagliptin, teneligliptin and dutogliptin, and, optionally, a second antidiabetic agent selected from biguanides, thiazolidindiones, sulfonylureas, glinides, inhibitors of alpha-glucosidase, GLP-1 or GLP-1 analogues, and insulin or insulin analogues, and, optionally, a third antidiabetic agent selected from biguanides, thiazolidindiones, sulfonylureas, glinides, inhibitors of alpha-glucosidase, GLP-1 or GLP-1 analogues, and insulin or insulin analogues, to the patient, optionally in combination, including in alternation.

2. The method according to claim 1 wherein the patient has insufficient glycemic control despite diet and exercise, or despite monotherapy with the second or the third antidiabetic agent.

3. The method according to claim 1 wherein the patient has insufficient glycemic control despite diet and exercise, or despite dual therapy with the second and the third antidiabetic agent.

4. The method according to claim 1 wherein the patient has insufficient glycemic control despite diet and exercise, or despite monotherapy with either the DPP-4 inhibitor or the second or third antidiabetic agent, or despite dual therapy with the second and the third antidiabetic agent.

5. The method according to claim 1 wherein the patient has insufficient glycemic control despite diet and exercise, or despite monotherapy with either the DPP-4 inhibitor, the second or the third antidiabetic agent, or despite combination therapy with two agents selected from the group of the DPP-4 inhibitor, the second and the third antidiabetic agent.

6. The method according to claim 1 wherein the patient is diagnosed for, has been diagnosed with, or carries two T alleles of SNP rs7903146 of TCF7L2.

7. The method according to claim 1 wherein the patient is diagnosed for, has been diagnosed with, or carries one T allele of SNP rs7903146 of TCF7L2.

8. The method according to claim 1 wherein the DPP-4 inhibitor is linagliptin.

9. The method according to claim 1 wherein the DPP-4 inhibitor is linagliptin, and the second antidiabetic agent is metformin or pioglitazone.

* * * * *

SEQUENCE LISTING

<160> NUMBER OF SEQ ID NOS: 1

<210> SEQ ID NO 1
<211> LENGTH: 51
<212> TYPE: DNA
<213> ORGANISM: Homo sapiens

<400> SEQUENCE: 1
tagagagcta agcacttttt agataytata taatttaatt gccgtatgag g        51